US012383566B2

(12) United States Patent
Burridge et al.

(10) Patent No.: US 12,383,566 B2
(45) Date of Patent: Aug. 12, 2025

(54) INHIBITION OF SLC TRANSPORTER ACTIVITY OR EXPRESSION TO ATTENUATE ANTHRACYCLINE-INDUCED CARDIOTOXICITY

(71) Applicant: Northwestern University, Evanston, IL (US)

(72) Inventors: Paul W. Burridge, Chicago, IL (US); Tarek Magdy Shehata Mohamed, Chicago, IL (US)

(73) Assignee: Northwestern University, Evanston, IL (US)

( * ) Notice: Subject to any disclaimer, the term of this patent is extended or adjusted under 35 U.S.C. 154(b) by 206 days.

(21) Appl. No.: 18/051,386

(22) Filed: Oct. 31, 2022

(65) Prior Publication Data

US 2023/0190773 A1 Jun. 22, 2023

Related U.S. Application Data

(60) Provisional application No. 63/273,668, filed on Oct. 29, 2021.

(51) Int. Cl.
| | | |
|---|---|---|
| *A61K 31/65* | (2006.01) | |
| *A61K 31/55* | (2006.01) | |
| *A61K 45/06* | (2006.01) | |
| *A61P 9/00* | (2006.01) | |

(52) U.S. Cl.
CPC .............. *A61K 31/65* (2013.01); *A61K 31/55* (2013.01); *A61K 45/06* (2013.01); *A61P 9/00* (2018.01)

(58) Field of Classification Search
CPC ................................ A61K 31/122; A61P 1/00
See application file for complete search history.

(56) References Cited

U.S. PATENT DOCUMENTS 6,194,454 B1 * 2/2001 Dow .................. A61P 9/10
558/417

FOREIGN PATENT DOCUMENTS

WO WO-2006017185 A1 * 2/2006 ......... A61K 31/4172

OTHER PUBLICATIONS

Megías-Vericat et al., "Pharmacogenetics of Metabolic Genes of Anthracyclines in Acute Myeloid Leukemia", Current Drug Metabolism, vol. 9, No. 1, pp. 55-74 (2018).*
Malan D, Zhang M, Stallmeyer B, Müller J, Fleischmann BK, Schulze-Bahr E, Sasse P and Greber B. Human iPS cell model of type 3 long QT syndrome recapitulates drug-based phenotype correction. Basic Res Cardiol. 2016; 111.
Maurano MT, Humbert R, Rynes E, Thurman RE, Haugen E, Wang H, Reynolds AP, Sandstrom R, Qu H, Brody J, et al. Systematic localization of common disease-associated variation in regulatory DNA. Science. 2012;337:1190-5.
Minematsu T and Giacomini KM. Interactions of tyrosine kinase inhibitors with organic cation transporters and multidrug and toxic compound extrusion proteins. Mol Cancer Ther. 2011;10:531-9.
Narasimhan V, Danecek P, Scally A, Xue Y, Tyler-Smith C and Durbin R. BCFtools/RoH: a hidden Markov model approach for detecting autozygosity from next-generation sequencing data. Bioinformatics. 2016;32:1749-51.
Nelson MR, Tipney H, Painter JL, Shen J, Nicoletti P, Shen Y, Floratos A, Sham PC, Li MJ, Wang J, et al. The support of human genetic evidence for approved drug indications. Nat Genet. 2015;47:856-60.
Nozawa T, Tamai I, Sai Y, Nezu J and Tsuji A. Contribution of organic anion transporting polypeptide OATP-C to hepatic elimination of the opioid pentapeptide analogue [D-Ala2, D-Leu5]-enkephalin. J Pharm Pharmacol. 2003;55:1013-20.
Oceguera-Yanez F, Kim SI, Matsumoto T, Tan GW, Xiang L, Hatani T, Kondo T, Ikeya M, Yoshida Y, Inoue H, et al. Engineering the AAVS1 locus for consistent and scalable transgene expression in human iPSCs and their differentiated derivatives. Methods. 2016;101:43-55.
Ohashi R, Tamai I, Yabuuchi H, Nezu JI, Oku A, Sai Y, Shimane M and Tsuji A. Na(+)-dependent carnitine transport by organic cation transporter (OCTN2): its pharmacological and toxicological relevance. J Pharmacol Exp Ther. 1999;291:778-84.
Oostendorp RL, van de Steeg E, van der Kruijssen CM, Beijnen JH, Kenworthy KE, Schinkel AH and Schellens JH. Organic anion-transporting polypeptide 1B1 mediates transport of Gimatecan and BNP1350 and can be inhibited by several classic ATP-binding cassette (Abc) B1 and/or ABCG2 inhibitors. Drug Metab Dispos. 2009;37:917-23.
Oulianova N, Falk S and Berteloot A. Two-step mechanism of phlorizin binding to the SGLT1 protein in the kidney. The Journal of membrane biology. 2001;179:223-42.
Pahwa S, Alam K, Crowe A, Farasyn T, Neuhoff S, Hatley O, Ding K and Yue W. Pretreatment With Rifampicin and Tyrosine Kinase Inhibitor Dasatinib Potentiates the Inhibitory Effects Toward OATP1B1- and OATP1B3-Mediated Transport. J Pharm Sci. 2017;106:2123-2135.
Radchenko M, Symersky J, Nie R and Lu M. Structural basis for the blockade of MATE multidrug efflux pumps. Nat Commun. 2015;6:7995.
Ramirez F, Ryan DP, Gruning B, Bhardwaj V, Kilpert F, Richter AS, Heyne S, Dundar F and Manke T. deepTools2: a next generation web server for deep-sequencing data analysis. Nucleic Acids Res. 2016;44:W160-5.
Ran FA, Hsu PD, Wright J, Agarwala V, Scott DA and Zhang F. Genome engineering using the CRISPR-Cas9 system. Nat Protoc. 2013;8:2281-308.
Ritz C, Baty F, Streibig JC and Gerhard D. Dose-Response Analysis Using R. PLoS ONE. 2015;10:e0146021.

(Continued)

*Primary Examiner* — Kevin E Weddington
(74) *Attorney, Agent, or Firm* — Quarles & Brady LLP

(57) ABSTRACT

Disclosed are methods, pharmaceutical compositions, kits, and systems for treating or preventing cardiotoxicity in a subject undergoing treatment with an anthracycline chemotherapeutic agent. The methods, pharmaceutical compositions, kits, and systems typically include or utilize a therapeutic agent that inhibits the activity or expression of the solute transporter SLC28A3.

14 Claims, 42 Drawing Sheets
(38 of 42 Drawing Sheet(s) Filed in Color)
Specification includes a Sequence Listing.

(56) References Cited

OTHER PUBLICATIONS

Schaub MA, Boyle AP, Kundaje A, Batzoglou S and Snyder M. Linking disease associations with regulatory information in the human genome. Genome Res. 2012;22:1748-59.

Schmittgen TD and Livak KJ. Analyzing real-time PCR data by the comparative C(T) method. Nat Protoc. 2008;3:1101-8.

Schroeder A, Eckhardt U, Stieger B, Tynes R, Schteingart CD, Hofmann AF, Meier PJ and Hagenbuch B. Substrate specificity of the rat liver Na(+)-bile salt cotransporter in Xenopus laevis oocytes and in CHO cells. The American journal of physiology. 1998;274:G370-5.

Sekine T, Cha SH, Tsuda M, Apiwattanakul N, Nakajima N, Kanai Y and Endou H. Identification of multispecific organic anion transporter 2 expressed predominantly in the liver. FEBS letters. 1998;429:179-82.

Shen H, Yang Z, Zhao W, Zhang Y and Rodrigues AD. Assessment of vandetanib as an inhibitor of various human renal transporters: inhibition of multidrug and toxin extrusion as a possible mechanism leading to decreased cisplatin and creatinine clearance. Drug Metab Dispos. 2013;41:2095-103.

Shitara Y, Itoh T, Sato H, Li AP and Sugiyama Y. Inhibition of transporter-mediated hepatic uptake as a mechanism for drug-drug interaction between cerivastatin and cyclosporin A. J Pharmacol Exp Ther. 2003;304:610-6.

Shitara Y, Takeuchi K, Nagamatsu Y, Wada S, Sugiyama Y and Horie T. Long-lasting inhibitory effects of cyclosporin A, but not tacrolimus, on OATP1B1- and OATP1B3-mediated uptake. Drug Metab Pharmacokinet. 2012;27:368-78.

Sun N, Yazawa M, Liu J, Han L, Sanchez-Freire V, Abilez OJ, Navarrete EG, Hu S, Wang L, Lee A, et al. Patient-specific induced pluripotent stem cells as a model for familial dilated cardiomyopathy. Sci Transl Med. 2012;4:130ra47.

Swain SM, Whaley FS and Ewer MS. Congestive heart failure in patients treated with doxorubicin: A retrospective analysis of three trials. Cancer. 2003;97:2869-2879.

Taguchi T, Masuo Y, Kogi T, Nakamichi N and Kato Y. Characterization of Long-Lasting Oatp Inhibition by Typical Inhibitor Cyclosporine A and In Vitro-In Vivo Discrepancy in Its Drug Interaction Potential in Rats. J Pharm Sci. 2016;105:2231-9.

Taguchi T, Masuo Y, Sakai Y and Kato Y. Short-lasting inhibition of hepatic uptake transporter OATP1B1 by tyrosine kinase inhibitor pazopanib. Drug Metab Pharmacokinet. 2019;34:372-379.

Takeda M, Khamdang S, Narikawa S, Kimura H, Hosoyamada M, Cha SH, Sekine T and Endou H. Characterization of methotrexate transport and its drug interactions with human organic anion transporters. J Pharmacol Exp Ther. 2002;302:666-71.

Tan LL and Lyon AR. Role of Biomarkers in Prediction of Cardiotoxicity During Cancer Treatment. Curr Treat Options Cardiovasc Med. 2018;20:55.

Tsuda M, Terada T, Ueba M, Sato T, Masuda S, Katsura T and Inui K. Involvement of human multidrug and toxin extrusion 1 in the drug interaction between cimetidine and metformin in renal epithelial cells. J Pharmacol Exp Ther. 2009;329:185-91.

Urakami Y, Akazawa M, Saito H, Okuda M and Inui K. cDNA cloning, functional characterization, and tissue distribution of an alternatively spliced variant of organic cation transporter hOCT2 predominantly expressed in the human kidney. Journal of the American Society of Nephrology : JASN. 2002;13:1703-10.

Van Montfoort JE, Müller M, Groothuis GM, Meijer DK, Koepsell H and Meier PJ. Comparison of "type I" and "type II" organic cation transport by organic cation transporters and organic anion-transporting polypeptides. J Pharmacol Exp Ther. 2001;298:110-5.

Vavricka SR, Van Montfoort J, Ha HR, Meier PJ and Fattinger K. Interactions of rifamycin SV and rifampicin with organic anion uptake systems of human liver. Hepatology (Baltimore, Md). 2002;36:164-72.

Visscher H, Ross CJD, Rassekh SR, Barhdadi A, Dubé M-P, Al-Saloos H, Sandor GS, Caron HN, van Dalen EC, Kremer LC, et al. Pharmacogenomic prediction of anthracycline-induced cardiotoxicity in children. J Clin Oncol. 2012;30:1422-1428.

Visscher H, Ross CJD, Rassekh SR, Sandor GSS, Caron HN, van Dalen EC, Kremer LC, van der Pal HJ, Rogers PC, Rieder MJ, et al. Validation of variants in SLC28A3 and UGT1A6 as genetic markers predictive of anthracycline-induced cardiotoxicity in children. Pediatr Blood Cancer. 2013;60:1375-1381.

Wang G, McCain ML, Yang L, He A, Pasqualini FS, Agarwal A, Yuan H, Jiang D, Zhang D, Zangi L, et al. Modeling the mitochondrial cardiomyopathy of Barth syndrome with induced pluripotent stem cell and heart-on-chip technologies. Nat Med. 2014;20:616-623.

Weisheit I, Kroeger JA, Malik R, Klimmt J, Crusius D, Dannert A, Dichgans M and Paquet D. Detection of Deleterious On-Target Effects after HDR-Mediated CRISPR Editing. Cell Rep. 2020;31:107689.

Wick RR, Judd LM, Gorrie CL and Holt KE. Completing bacterial genome assemblies with multiplex MinION sequencing. Microbial genomics. 2017;3:e000132.

Wu X, George RL, Huang W, Wang H, Conway SJ, Leibach FH and Ganapathy V. Structural and functional characteristics and tissue distribution pattern of rat OCTN1, an organic cation transporter, cloned from placenta. Biochim Biophys Acta. 2000; 1466:315-27.

Wu X, Huang W, Ganapathy ME, Wang H, Kekuda R, Conway SJ, Leibach FH and Ganapathy V. Structure, function, and regional distribution of the organic cation transporter OCT3 in the kidney. American journal of physiology Renal physiology. 2000;279:F449-58.

Wu X, Huang W, Prasad PD, Seth P, Rajan DP, Leibach FH, Chen J, Conway SJ and Ganapathy V. Functional characteristics and tissue distribution pattern of organic cation transporter 2 (OCTN2), an organic cation/carnitine transporter. J Pharmacol Exp Ther. 1999;290:1482-92.

Xu Q, Wang C, Meng Q, Liu Q, Sun H, Peng J, Ma X, Kaku T and Liu K. OAT1 and OAT3: targets of drug-drug interaction between entecavir and JBP485. European journal of pharmaceutical sciences : official journal of the European Federation for Pharmaceutical Sciences. 2013;48:650-7.

Yabuuchi H, Tamai I, Nezu J, Sakamoto K, Oku A, Shimane M, Sai Y and Tsuji A. Novel membrane transporter OCTN1 mediates multispecific, bidirectional, and pH-dependent transport of organic cations. J Pharmacol Exp Ther. 1999;289:768-73.

Yazawa M, Hsueh B, Jia X, Pasca AM, Bernstein JA, Hallmayer J and Dolmetsch RE. Using iPS cells to investigate cardiac phenotypes in patients with Timothy Syndrome. Nature. 2011;471:230-234.

Yin J, Duan H and Wang J. Impact of Substrate-Dependent Inhibition on Renal Organic Cation Transporters hOCT2 and hMATE 1/2-K-Mediated Drug Transport and Intracellular Accumulation. J Pharmacol Exp Ther. 2016;359:401-410.

Zhang L, Schaner ME and Giacomini KM. Functional characterization of an organic cation transporter (hOCT1) in a transiently transfected human cell line (HeLa). J Pharmacol Exp Ther. 1998;286:354-61.

Zhou J and Troyanskaya OG. Predicting effects of noncoding variants with deep learning-based sequence model. Nat Methods. 2015;12:931-4.

Magdy et al. Circulation. 2022; 145:279-294.

Aminkeng F, Bhavsar AP, Visscher H, Rassekh SR, Li Y, Lee JW, Brunham LR, Caron HN, van Dalen EC, Kremer LC, et al. A coding variant in RARG confers susceptibility to anthracycline-induced cardiotoxicity in childhood cancer. Nat Genet. 2015;47:1079-84.

Aminkeng F, Ross CJD, Rassekh SR, Hwang S, Rieder MJ, Bhavsar AP, Smith A, Sanatani S, Gelmon KA, Bernstein D, et al. Recommendations for genetic testing to reduce the incidence of anthracycline-induced cardiotoxicity. Br J Clin Pharmacol. 2016;82:683-695.

Aminkeng F, Ross CJD, Rassekh SR, Rieder MJ, Bhavsar AP, Sanatani S, Bernstein D, Hayden MR, Amstutz U and Carleton BC. Pharmacogenomic screening for anthracycline-induced cardiotoxicity in childhood cancer. Br J Clin Pharmacol. 2017;83:1143-1145.

Andersen J, Kristensen AS, Bang-Andersen B and Stromgaard K. Recent advances in the understanding of the interaction of antidepressant drugs with serotonin and norepinephrine transporters. Chem Commun (Camb). 2009:3677-92.

(56) References Cited

OTHER PUBLICATIONS

Arrowsmith J and Miller P. Trial watch: phase II and phase III attrition rates 2011-2012. Nat Rev Drug Discov. 2013;12:569.
Avila MS, Ayub-Ferreira SM, de Barros Wanderley MR, Jr., das Dores Cruz F, Goncalves Brandao SM, Rigaud VOC, Higuchi-Dos-Santos MH, Hajjar LA, Kalil Filho R, Hoff PM, et al. Carvedilol for Prevention of Chemotherapy-Related Cardiotoxicity: The CECCY Trial. J Am Coll Cardiol. 2018;71:2281-2290.
Bednarczyk D, Ekins S, Wikel JH and Wright SH. Influence of molecular structure on substrate binding to the human organic cation transporter, hOCT1. Mol Pharmacol. 2003;63:489-98.
Braun D and Schweizer U. Authentic bosutinib inhibits triiodothyronine transport by monocarboxylate transporter 8. Thyroid. 2014;24:926-7.
Braun D, Kim TD, le Coutre P, Köhrle J, Hershman JM and Schweizer U. Tyrosine kinase inhibitors noncompetitively inhibit MCT8-mediated iodothyronine transport. The Journal of clinical endocrinology and metabolism. 2012;97:E100-5.
Burridge PW, Holmstrom A and Wu JC. Chemically Defined Culture and Cardiomyocyte Differentiation of Human Pluripotent Stem Cells. Curr Protoc Hum Genet. 2015;87:21 3 1-15.
Burridge PW, Matsa E, Shukla P, Lin ZC, Churko JM, Ebert AD, Lan F, Diecke S, Huber B, Mordwinkin NM, et al. Chemically defined generation of human cardiomyocytes. Nat Methods. 2014; 11:855-60.
Cardinale D, Colombo A, Bacchiani G, Tedeschi I, Meroni CA, Veglia F, Civelli M, Lamantia G, Colombo N, Curigliano G, et al. Early detection of anthracycline cardiotoxicity and improvement with heart failure therapy. Circulation. 2015; 131:1981-8.
Carvajal-Vergara X, Sevilla A, D'Souza SL, Ang Y-S, Schaniel C, Lee D-F, Yang L, Kaplan AD, Adler ED, Rozov R, et al. Patient-specific induced pluripotent stem cell derived models of LEOPARD syndrome. Nature. 2010;465:808-812.
Cha SH, Sekine T, Fukushima JI, Kanai Y, Kobayashi Y, Goya T and Endou H. Identification and characterization of human organic anion transporter 3 expressing predominantly in the kidney. Mol Pharmacol. 2001;59:1277-86.
Cho SK, Kim CO, Park ES and Chung JY. Verapamil decreases the glucose-lowering effect of metformin in healthy volunteers. Br J Clin Pharmacol. 2014;78:1426-32.
Chou BK, Gu H, Gao Y, Dowey SN, Wang Y, Shi J, Li Y, Ye Z, Cheng T and Cheng L. A facile method to establish human induced pluripotent stem cells from adult blood cells under feeder-free and xeno-free culture conditions: a clinically compliant approach. Stem Cells Transl Med. 2015;4:320-32.
Churko JM, Burridge PW and Wu JC. Generation of human iPSCs from human peripheral blood mononuclear cells using non-integrative Sendai virus in chemically defined conditions. Methods Mol Biol. 2013;1036:81-8.
Cingolani P, Patel VM, Coon M, Nguyen T, Land SJ, Ruden DM and Lu X. Using *Drosophila melanogaster* as a Model for Genotoxic Chemical Mutational Studies with a New Program, SnpSift. Front Genet. 2012;3:35.
Craddock AL, Love MW, Daniel RW, Kirby LC, Walters HC, Wong MH and Dawson PA. Expression and transport properties of the human ileal and renal sodium-dependent bile acid transporter. The American journal of physiology. 1998;274:G157-69.
Cui Y, König J, Leier I, Buchholz U and Keppler D. Hepatic uptake of bilirubin and its conjugates by the human organic anion transporter SLC21A6. J Biol Chem. 2001;276:9626-30.
Cvetkovic M, Leake B, Fromm MF, Wilkinson GR and Kim RB. OATP and P-glycoprotein transporters mediate the cellular uptake and excretion of fexofenadine. Drug Metab Dispos. 1999;27:866-71.
Damaraju VL, Weber D, Kuzma M, Cass CE and Sawyer MB. Selective Inhibition of Human Equilibrative and Concentrative Nucleoside Transporters by BCR-ABL Kinase Inhibitors: Identification of Key hENT1 Amino Acid Residues for Interaction With BCR-ABL Kinase Inhibitors. J Biol Chem. 2016;291:18809-17.
Dandage R, Despres PC, Yachie N and Landry CR. beditor: A Computational Workflow for Designing Libraries of Guide RNAs for CRISPR-Mediated Base Editing. Genetics. 2019.
Danecek P, Auton A, Abecasis G, Albers CA, Banks E, DePristo MA, Handsaker RE, Lunter G, Marth GT, Sherry ST, et al. The variant call format and VCFtools. Bioinformatics. 2011;27:2156-8.
David-Silva A, Esteves JV, Morais M, Freitas HS, Zorn TM, Correa-Giannella ML and Machado UF. Dual SGLT1/SGLT2 Inhibitor Phlorizin Ameliorates Non-Alcoholic Fatty Liver Disease and Hepatic Glucose Production in Type 2 Diabetic Mice. Diabetes, metabolic syndrome and obesity : targets and therapy. 2020;13:739-751.
De Coster W, D'Hert S, Schultz DT, Cruts M and Van Broeckhoven C. NanoPack: visualizing and processing long-read sequencing data. Bioinformatics. 2018;34:2666-2669.
Diecke S, Lu J, Lee J, Termglinchan V, Kooreman NG, Burridge PW, Ebert AD, Churko JM, Sharma A, Kay MA, et al. Novel codon-optimized mini-intronic plasmid for efficient, inexpensive, and xeno-free induction of pluripotency. Sci Rep. 2015;5:8081.
Drawnel FM, Boccardo S, Prummer M, Delobel F, Graff A, Weber M, Gérard R, Badi L, Kam-Thong T, Bu L, et al. Disease modeling and phenotypic drug screening for diabetic cardiomyopathy using human induced pluripotent stem cells. Cell Rep. 2014;9:810-821.
Durinck S, Spellman PT, Birney E and Huber W. Mapping identifiers for the integration of genomic datasets with the R/Bioconductor package biomaRt. Nat Protoc. 2009;4:1184-1191.
Fattinger K, Cattori V, Hagenbuch B, Meier PJ and Stieger B. Rifamycin SV and rifampicin exhibit differential inhibition of the hepatic rat organic anion transporting polypeptides, Oatp1 and Oatp2. Hepatology (Baltimore, Md). 2000;32:82-6.
Fusaki N, Ban H, Nishiyama A, Saeki K and Hasegawa M. Efficient induction of transgene-free human pluripotent stem cells using a vector based on Sendai virus, an RNA virus that does not integrate into the host genome. Proc Jpn Acad Ser B Phys Biol Sci. 2009;85:348-62.
Giacomini KM, Huang SM, Tweedie DJ, Benet LZ, Brouwer KL, Chu X, Dahlin A, Evers R, Fischer V, Hillgren KM, et al. Membrane transporters in drug development. Nat Rev Drug Discov. 2010;9:215-36.
Gorboulev V, Ulzheimer JC, Akhoundova A, Ulzheimer-Teuber I, Karbach U, Quester S, Baumann C, Lang F, Busch AE and Koepsell H. Cloning and characterization of two human polyspecific organic cation transporters. DNA and cell biology. 1997;16:871-81.
Hirano M, Maeda K, Shitara Y and Sugiyama Y. Drug-drug interaction between pitavastatin and various drugs via OATP1B1. Drug Metab Dispos. 2006;34:1229-36.
Hu S, Mathijssen RH, de Bruijn P, Baker SD and Sparreboom A. Inhibition of OATP1B1 by tyrosine kinase inhibitors: in vitro-in vivo correlations. Br J Cancer. 2014;110:894-8.
Itzhaki I, Maizels L, Huber I, Zwi-Dantsis L, Caspi O, Winterstern A, Feldman O, Gepstein A, Arbel G, Hammerman H, et al. Modelling the long QT syndrome with induced pluripotent stem cells. Nature. 2011;471:225-229.
Kim C, Wong J, Wen J, Wang S, Wang C, Spiering S, Kan NG, Forcales S, Puri PL, Leone TC, et al. Studying arrhythmogenic right ventricular dysplasia with patient-specific iPSCs. Nature. 2013;494:105-110.
Kim D, Paggi JM, Park C, Bennett C and Salzberg SL. Graph-based genome alignment and genotyping with HISAT2 and HISAT-genotype. Nat Biotechnol. 2019;37:907-915.
Kouzuki H, Suzuki H and Sugiyama Y. Pharmacokinetic study of the hepatobiliary transport of indomethacin. Pharmaceutical research. 2000;17:432-8.
Kundaje A, Meuleman W, Ernst J, Bilenky M, Yen A, Heravi-Moussavi A, Kheradpour P, Zhang Z, Wang J, Ziller MJ, et al. Integrative analysis of 111 reference human epigenomes. Nature. 2015;518:317-30.
Kuo HH, Gao X, DeKeyser JM, Fetterman KA, Pinheiro EA, Weddle CJ, Fonoudi H, Orman MV, Romero-Tejeda M, Jouni M, et al. Negligible-Cost and Weekend-Free Chemically Defined Human iPSC Culture. Stem Cell Reports. 2020;14:256-270.

(56) References Cited

OTHER PUBLICATIONS

Li H, Handsaker B, Wysoker A, Fennell T, Ruan J, Homer N, Marth G, Abecasis G and Durbin R. The Sequence Alignment/Map format and SAMtools. Bioinformatics. 2009;25:2078-9.

Li H. Minimap2: pairwise alignment for nucleotide sequences. Bioinformatics. 2018;34:3094-3100.

Liao Y, Smyth GK and Shi W. The Subread aligner: fast, accurate and scalable read mapping by seed-and-vote. Nucleic Acids Res. 2013;41:e108.

Loman NJ, Quick J and Simpson JT. A complete bacterial genome assembled de novo using only nanopore sequencing data. Nat Methods. 2015;12:733-5.

Love MI, Huber W and Anders S. Moderated estimation of fold change and dispersion for RNA-seq data with DESeq2. Genome Biol. 2014;15:550.

Magdy T and Burridge PW. The future role of pharmacogenomics in anticancer agent-induced cardiovascular toxicity. Pharmacogenomics. 2018;19:79-82.

Magdy T and Burridge PW. Unraveling Difficult Answers: From Genotype to Phenotype in Coronary Artery Disease. Cell Stem Cell. 2019;24:203-205.

Magdy T, Burmeister BT and Burridge PW. Validating the pharmacogenomics of chemotherapy-induced cardiotoxicity: What is missing? Pharmacol Ther. 2016; 168:113-125.

Magdy T, Kuo HH and Burridge PW. Precise and Cost-Effective Nanopore Sequencing for Post-GWAS Fine-Mapping and Causal Variant Identification. iScience. 2020;23:100971.

\* cited by examiner

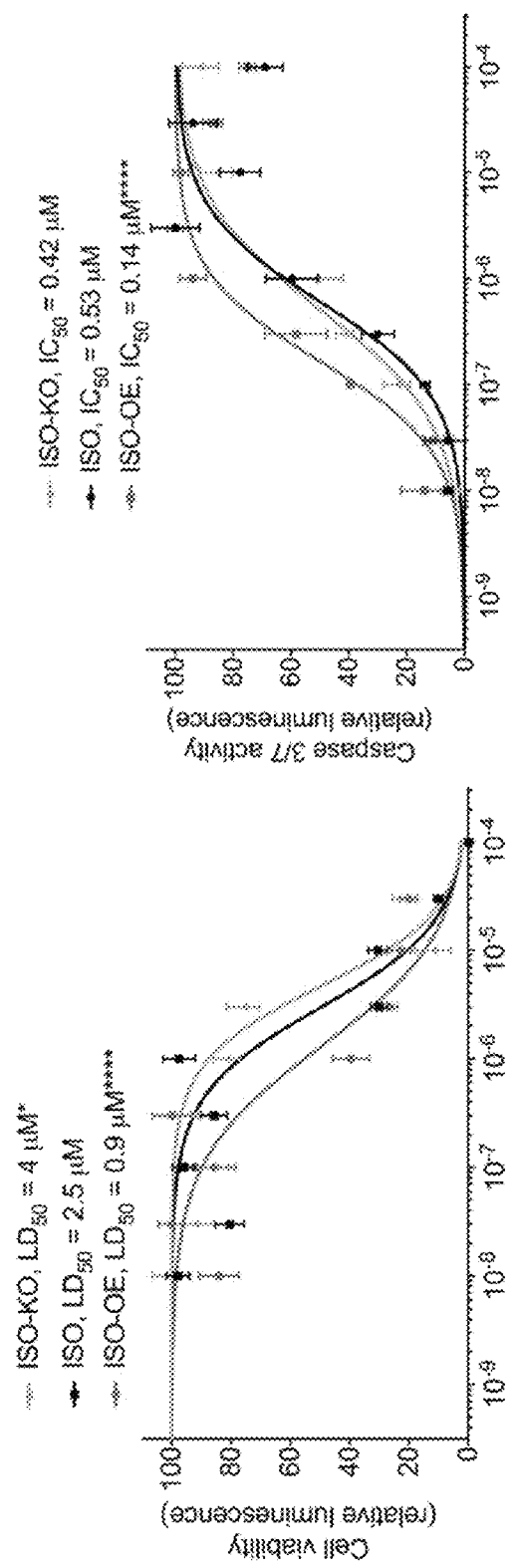
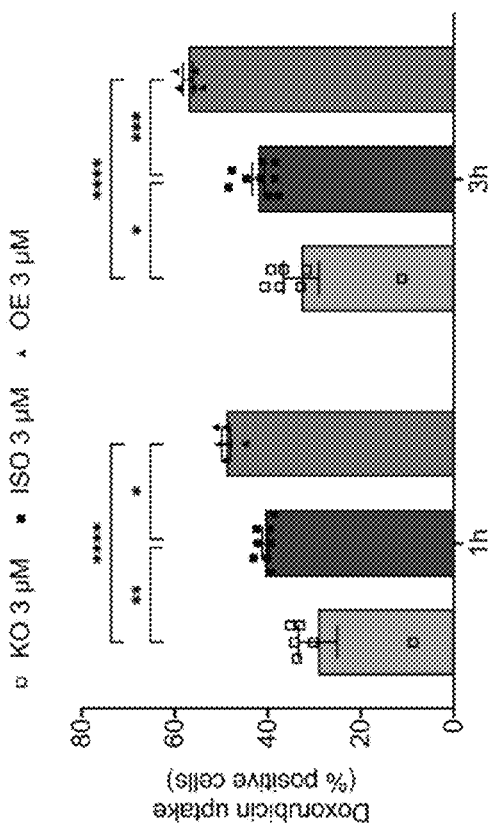
FIG. 2D, FIG. 2E, FIG. 2F

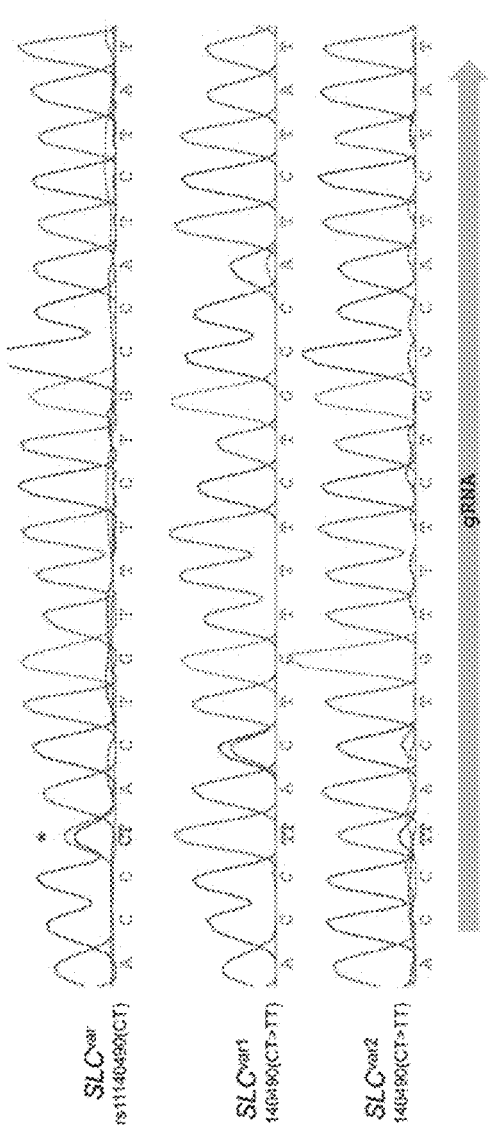
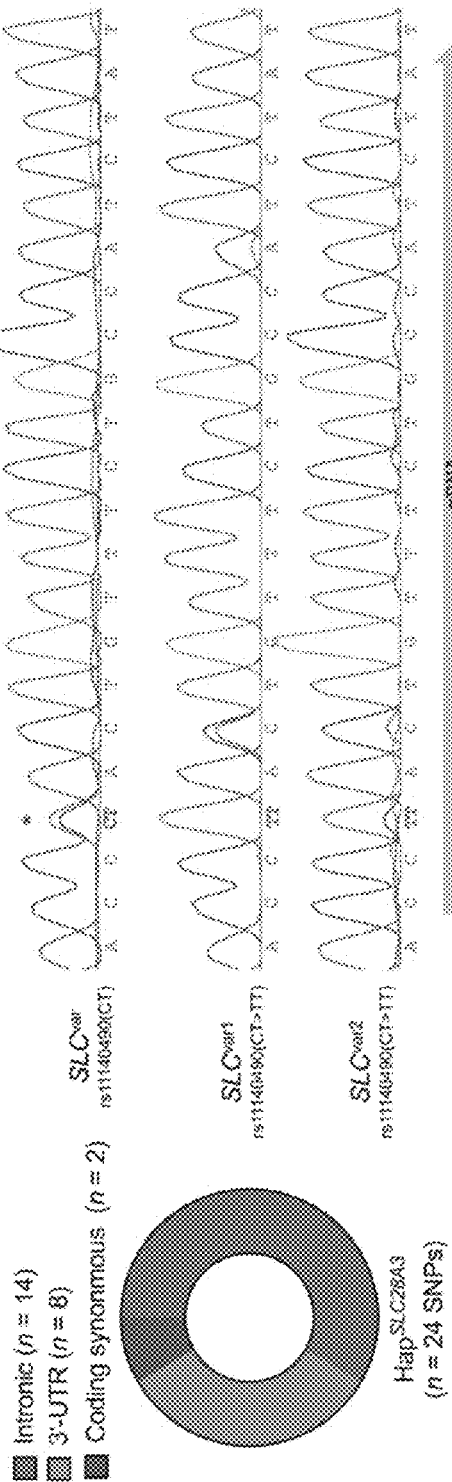
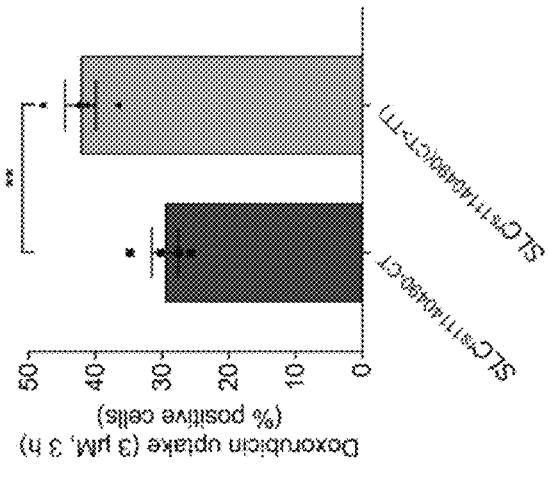
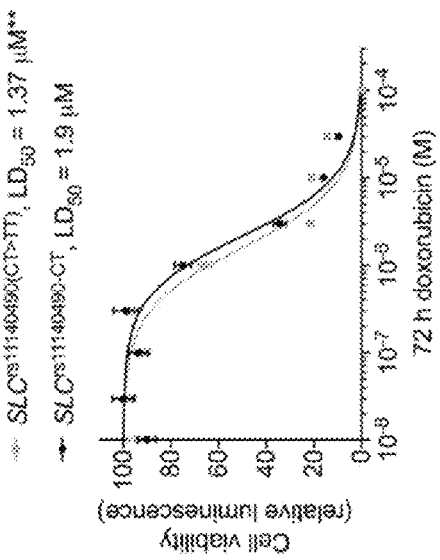
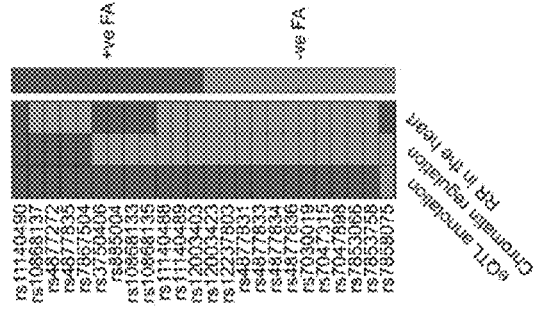

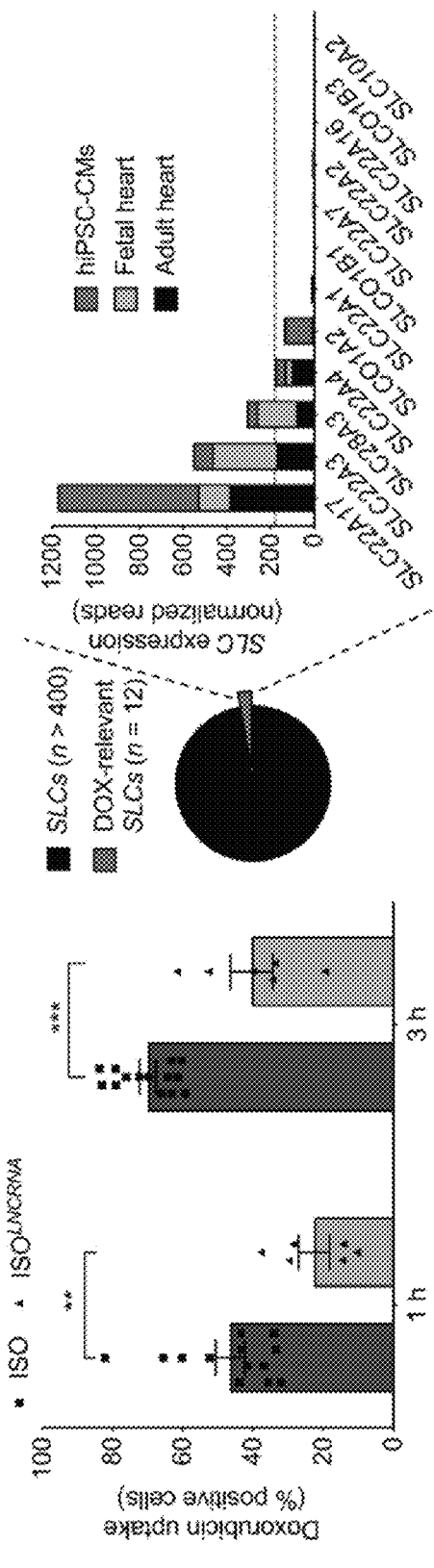
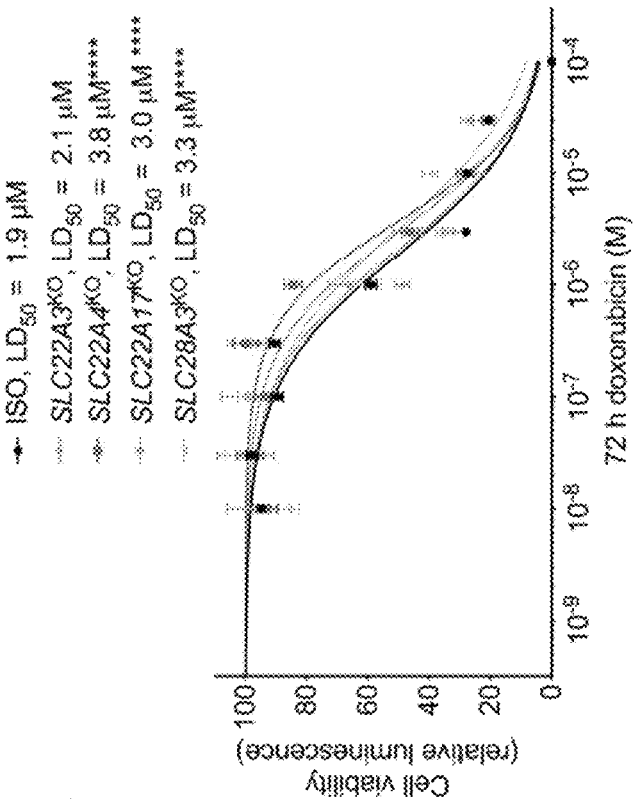
FIG. 4D
FIG. 4E
FIG. 4F
FIG. 4G

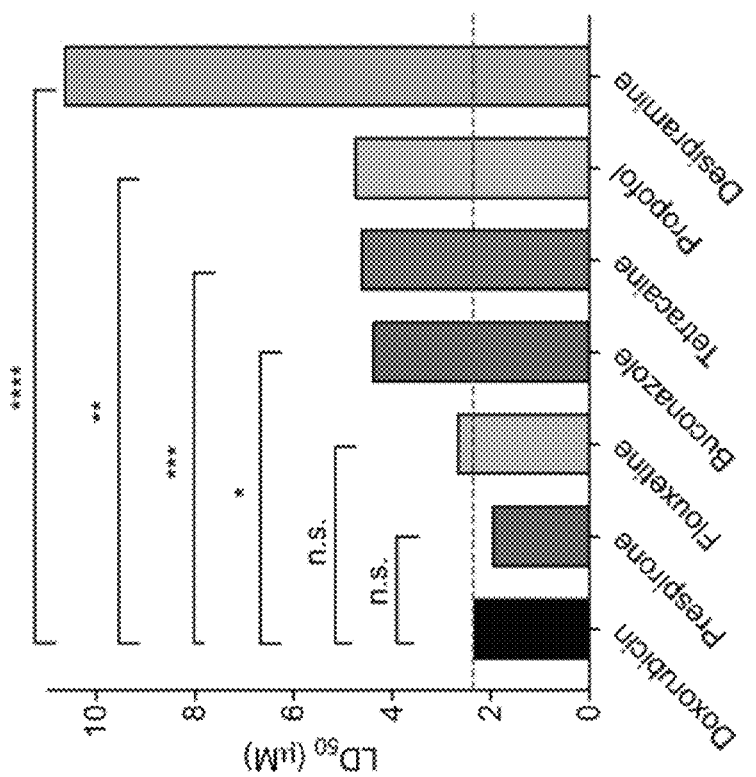
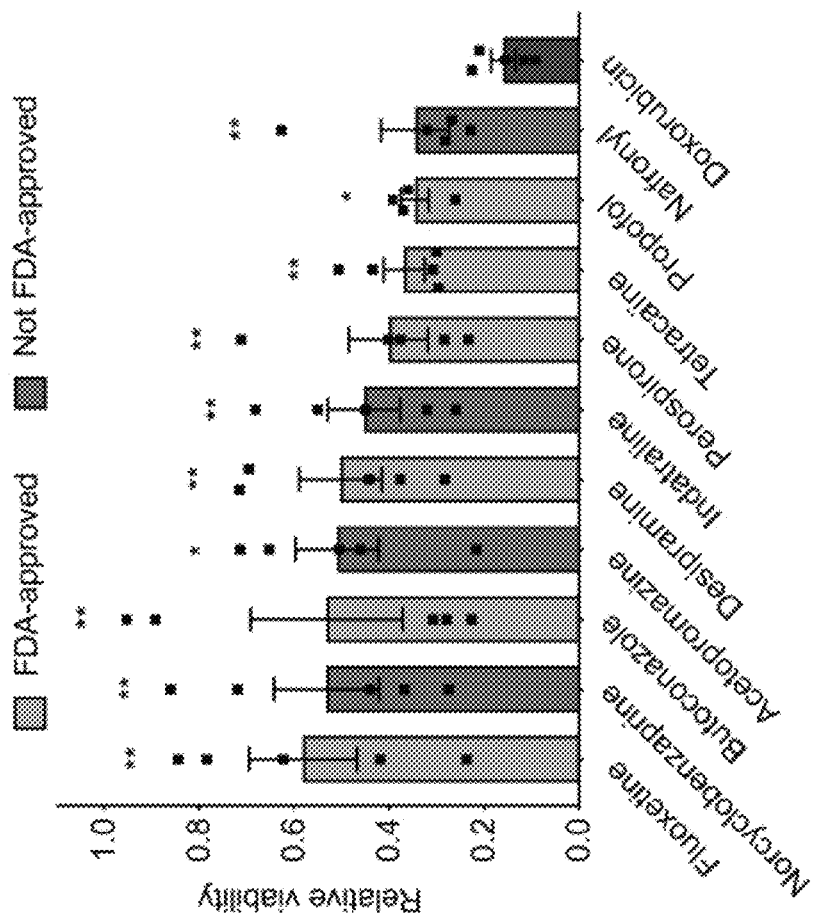

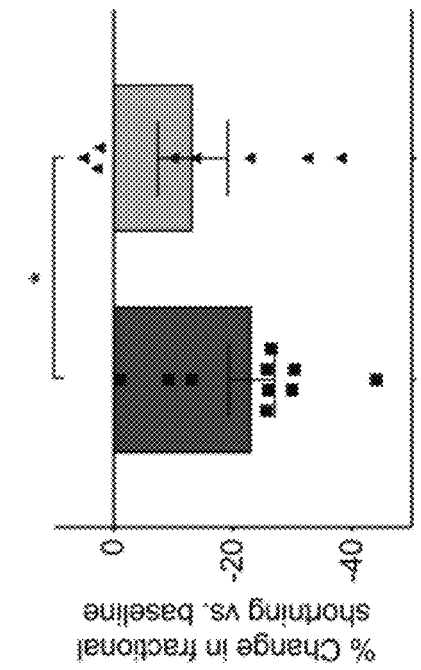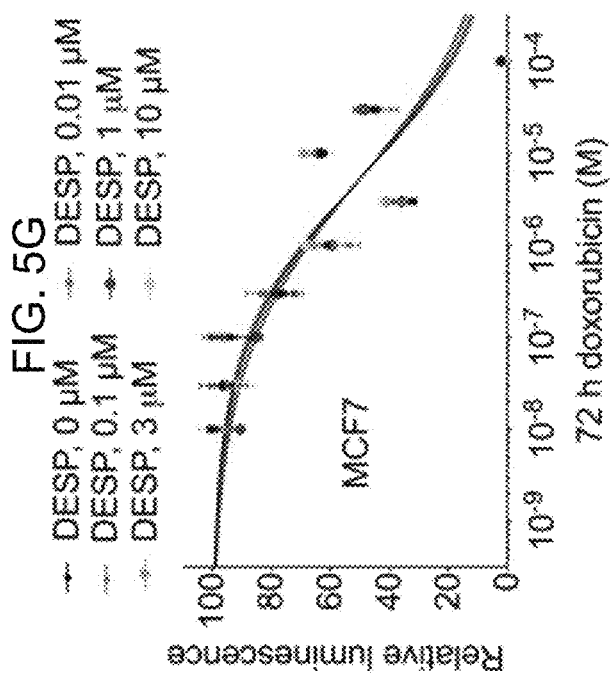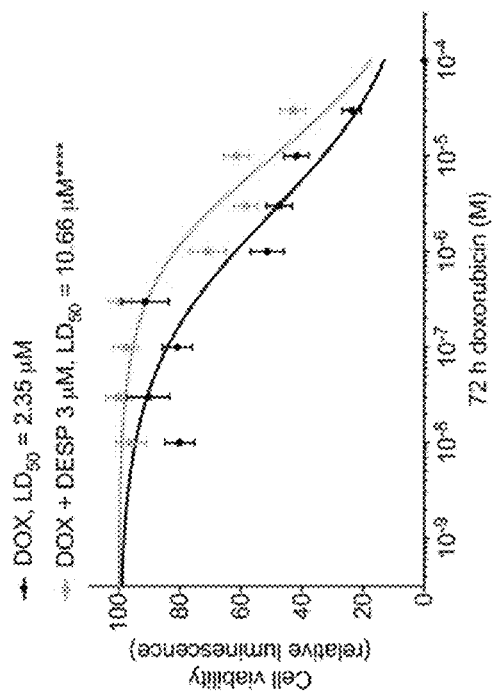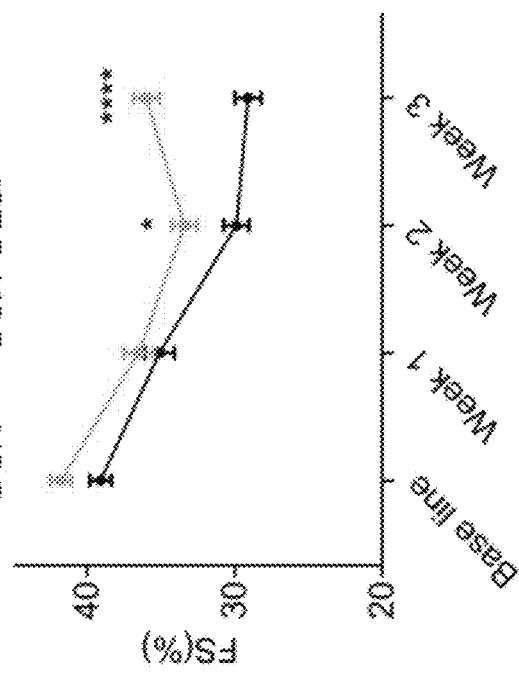

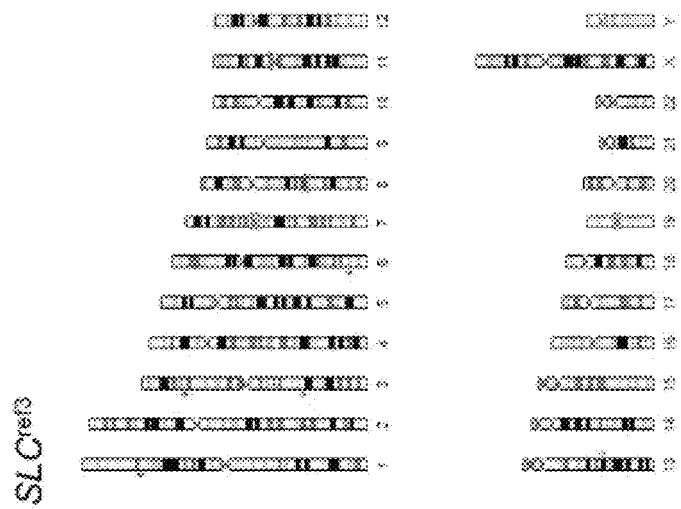
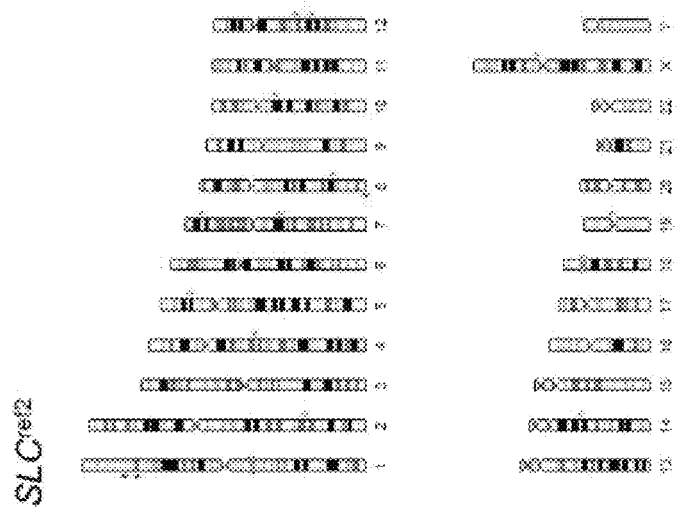
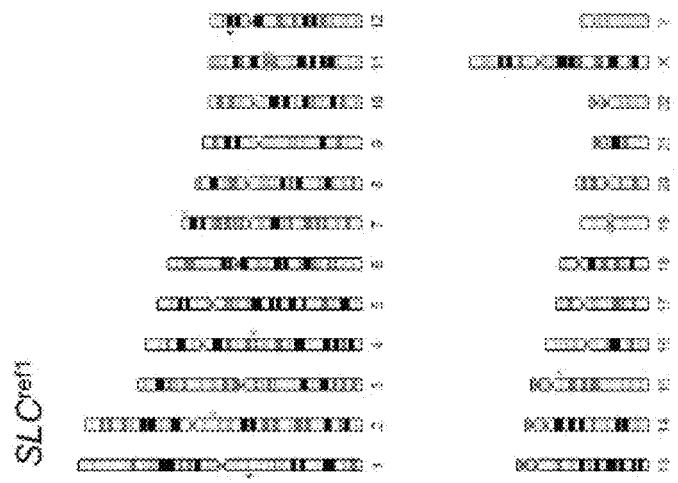
FIG. 7

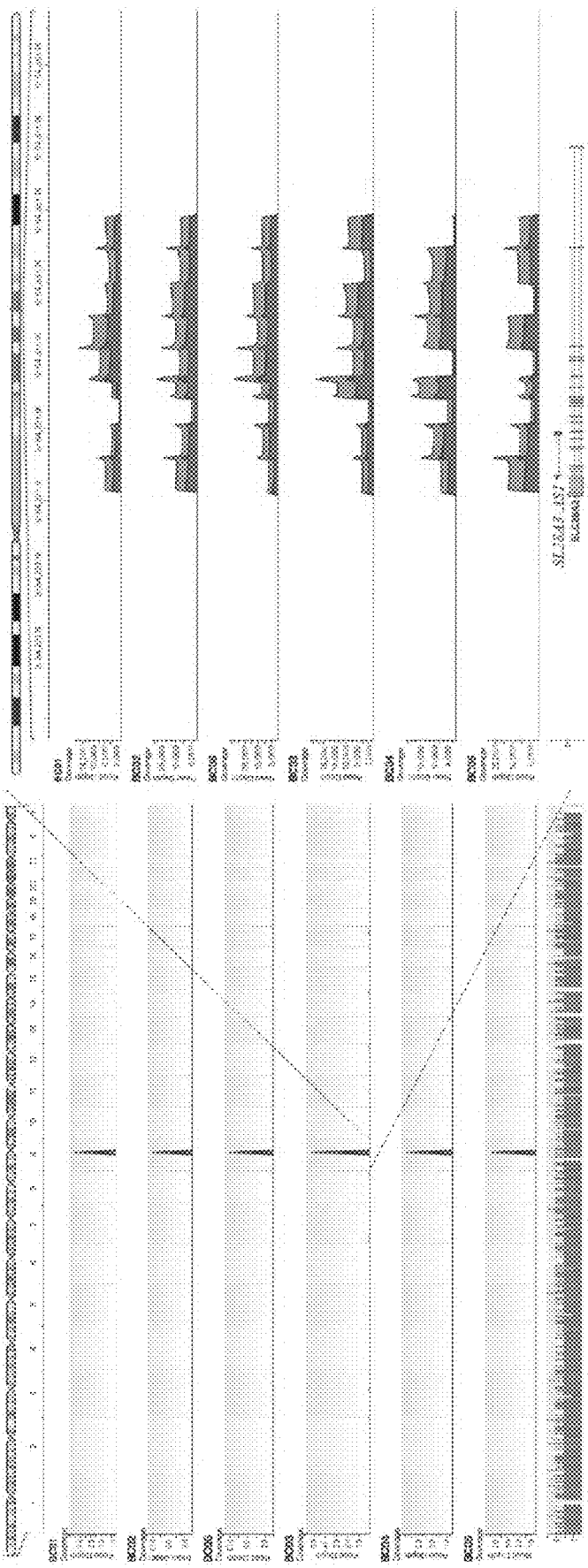

| Haplotype Id | rs11140490 (35, A>G) | rs10868135 (41, T>C) | rs4877831 (52, C>G) | rs4877833 (54, T>C) | rs7853066 (56, A>G) | rs7853758 (57, G>A) | rs7030019 (59, A>G) | Haplotype Frequency (%) |
|---|---|---|---|---|---|---|---|---|
| I | A | T | C | T | A | G | A | 71.7 |
| II | G | C | G | C | G | A | G | 17.7 |
| III | A | T | G | T | A | G | A | 7.1 |
| IV | G | C | G | C | G | G | A | 2 |
| V | G | C | C | C | G | G | A | 0.5 |
| VI | A | T | C | T | A | A | A | 0.5 |
| VII | G | C | C | T | A | A | G | 0.5 |

FIG. 10C

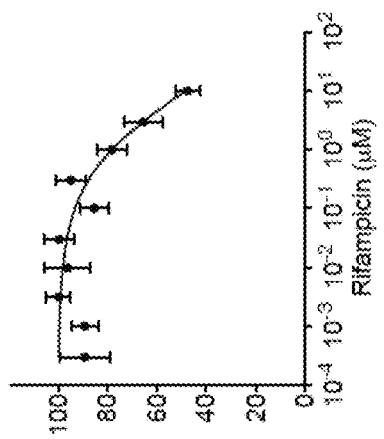
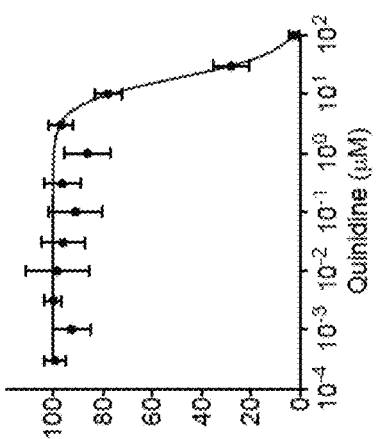
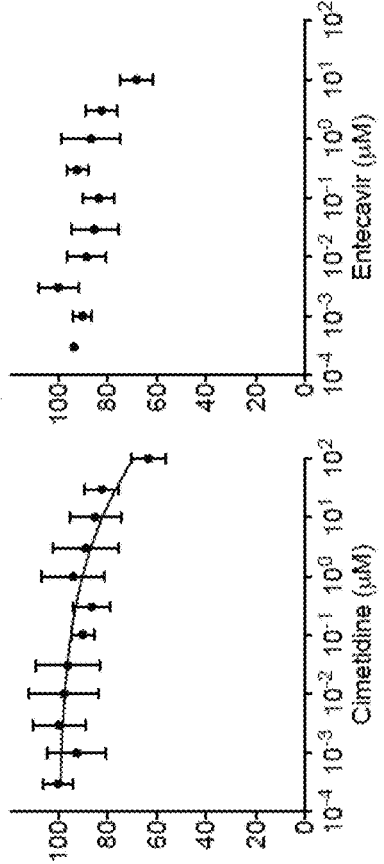
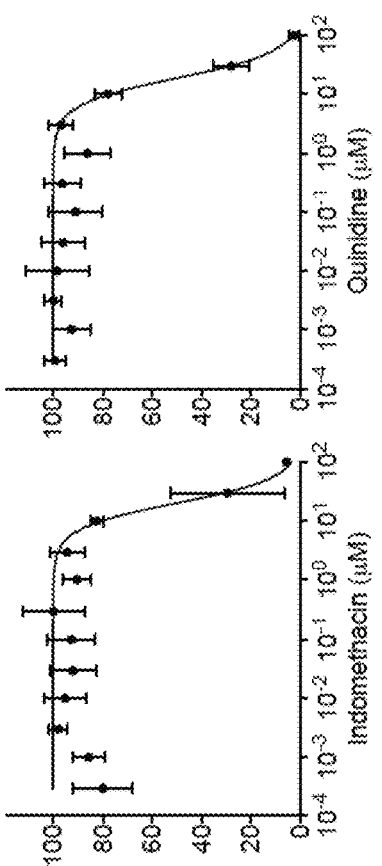
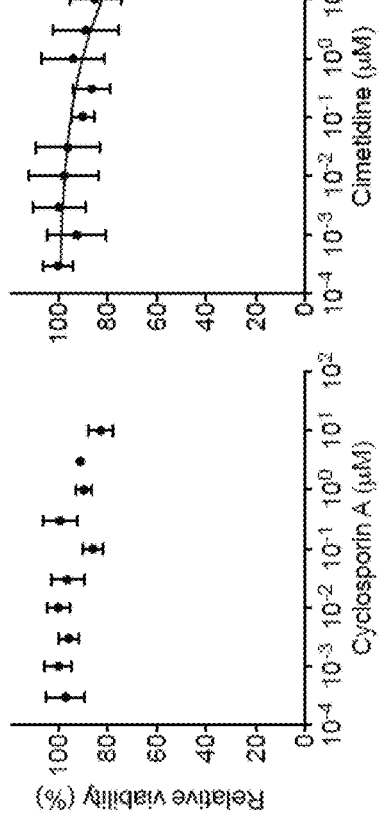
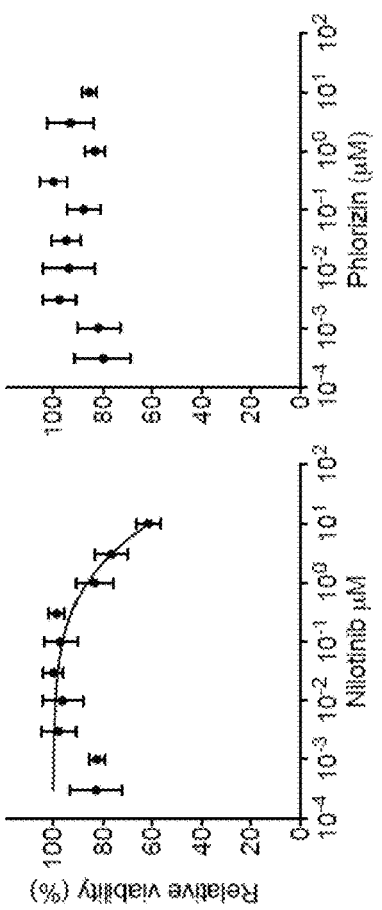

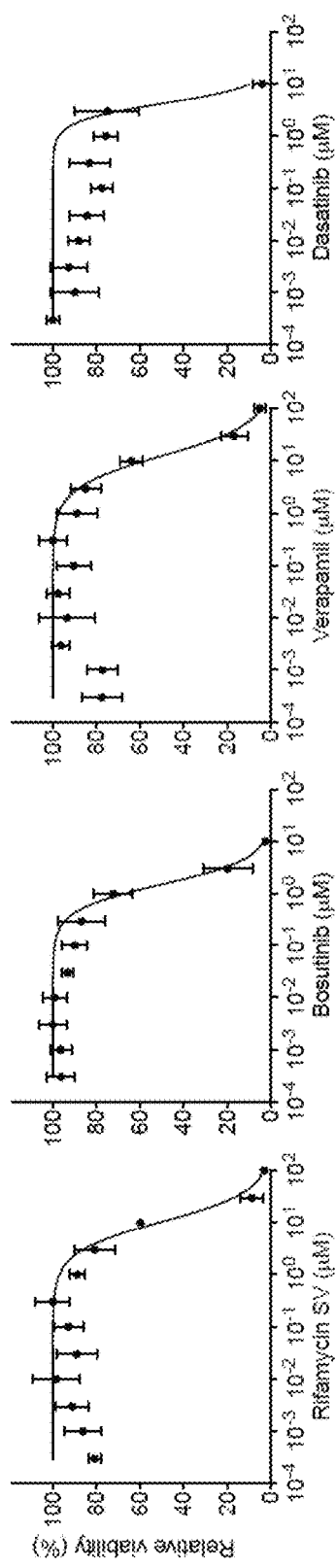
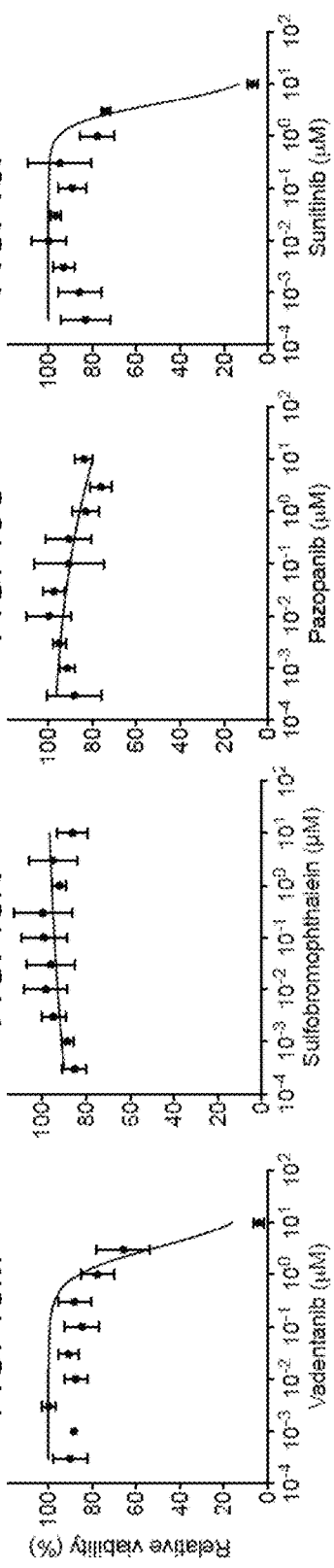
FIG. 13I  FIG. 13J  FIG. 13K  FIG. 13L
FIG. 13M  FIG. 13N  FIG. 13O  FIG. 13P
FIG. 13Q → 1 μM DESP   → 3 μM DESP   → 10 μM DESP
FIG. 15A  HEPG2
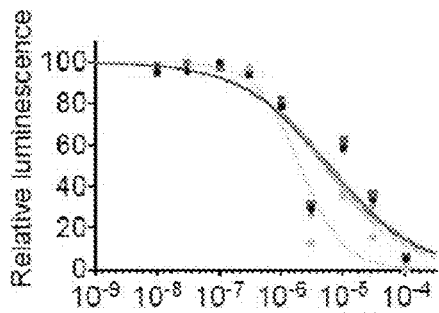
FIG. 15B  DLD1
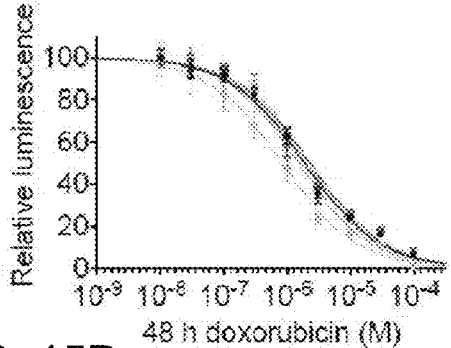
FIG. 15C  LNCAP
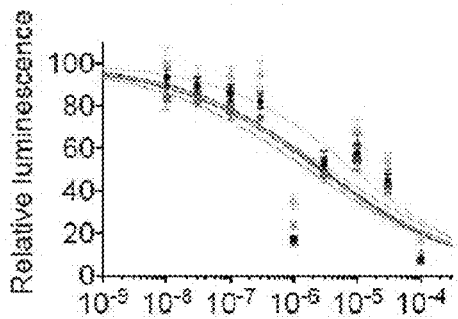
FIG. 15D  SK-UT-1
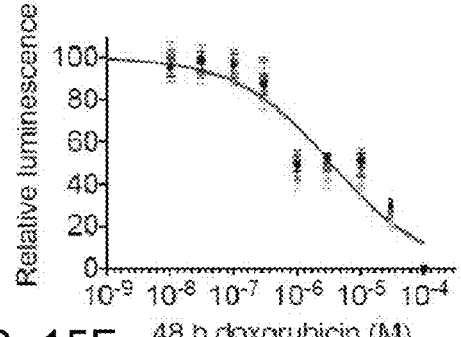
FIG. 15E  HELA
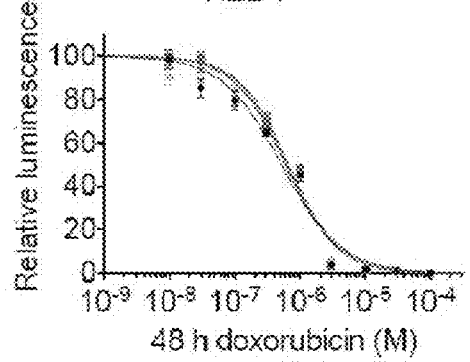
FIG. 15F  U2OS
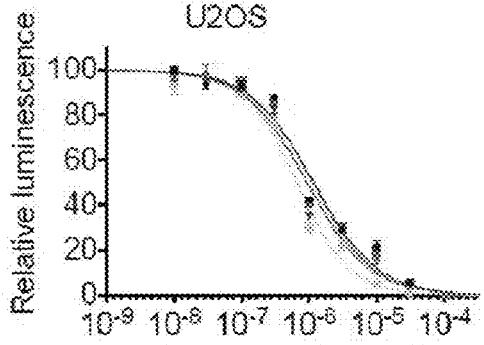
FIG. 15G  Hs578T
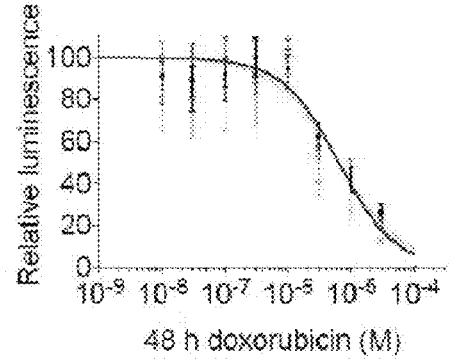
FIG. 15H  MDA-MB-231
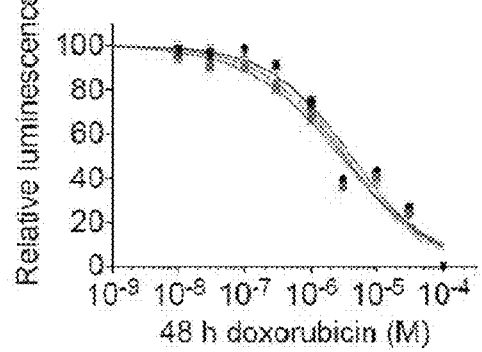

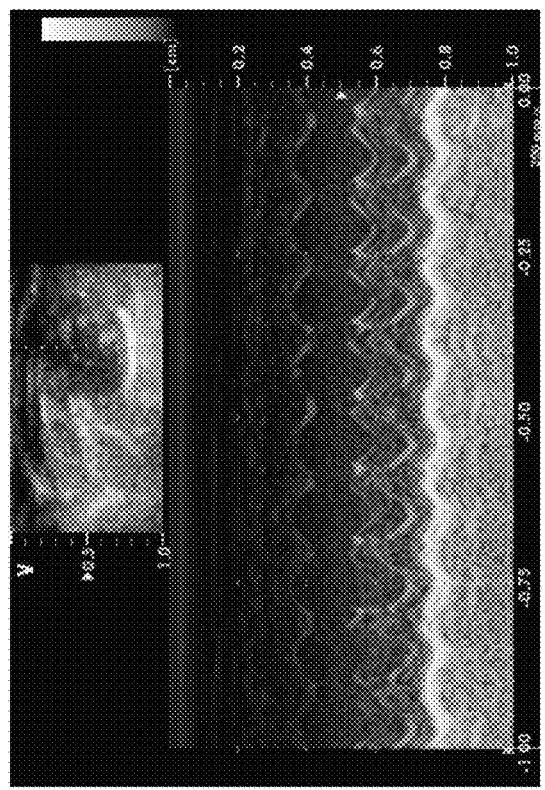
FIG. 17D  DOX + DESP
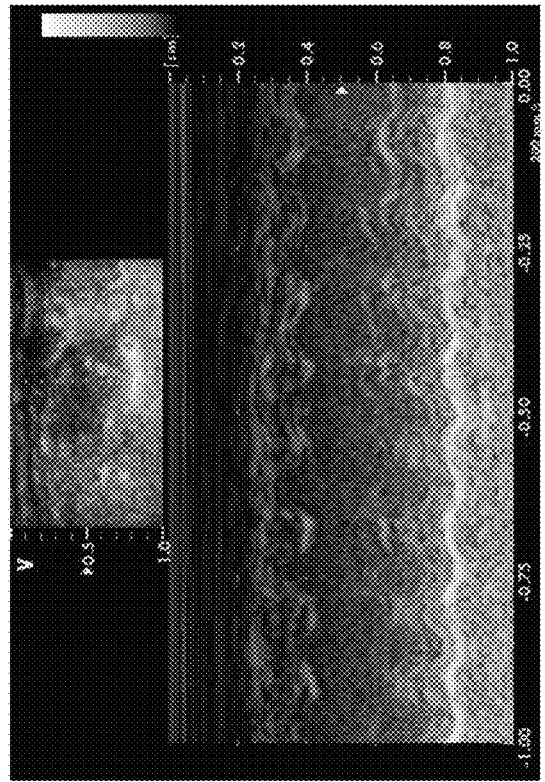
FIG. 17C  DOX

INHIBITION OF SLC TRANSPORTER ACTIVITY OR EXPRESSION TO ATTENUATE ANTHRACYCLINE-INDUCED CARDIOTOXICITY

CROSS-REFERENCE TO RELATED APPLICATIONS

The present application claims priority to U.S. Provisional Patent Application No. 63/273,668 that was filed Oct. 29, 2021, the entire contents of which are hereby incorporated by reference.

STATEMENT REGARDING FEDERALLY SPONSORED RESEARCH OR DEVELOPMENT

This invention was made with government support under HL121177 awarded by the National Institutes of Health. The government has certain rights in the invention.

SEQUENCE LISTING

A Sequence Listing accompanies this application and is submitted as an xml file of the sequence listing named "702581_02254.xml" which is 22,906 bytes in size and was created on Oct. 31, 2022. The sequence listing is electronically submitted via Patent Center and is incorporated herein by reference in its entirety.

FIELD OF THE INVENTION

The field of the invention relates to methods for inhibiting toxicity of anthracycline drugs. In particular, the field of the invention relates to methods for inhibiting cardiotoxicity by administering a therapeutic agent that inhibits the activity or expression of the solute transporter SLC28A3.

BACKGROUND

Multiple pharmacogenomic studies have identified the synonymous genomic variant rs7853758 (G>A, L461L) and the intronic variant rs885004 in SLC28A3 as statistically associated with a lower incidence of anthracycline-induced cardiotoxicity (AIC). However, the true causal variant(s), the cardioprotective mechanism of this locus, the role of SLC28A3 and other solute carrier (SLC) transporters in AIC, and the suitability of SLC transporters as targets for cardioprotective drugs has not been investigated.

Anthracycline chemotherapy agents are widely used for treating a broad range of malignancies. Commonly administered anthracycline agents include doxorubicin and daunorubicin among others. Unfortunately, anthracycline agents have a well-established dose-dependent cardiotoxicity that can lead to heart failure. At present, it is not possible to predict which patients will be affected by anthracycline-induced cardiotoxicity, including doxorubicin-induced cardiotoxicity (DIC). Only one drug to protect against doxorubicin-induced cardiotoxicity is currently approved by the Federal Drug Administration (Dexrazoxane™), which has a number of undesirable side-effects itself and concerns over efficacy. Therefore, there exists a need for compositions and methods to protect subjects being treated with anthracyclines from anthracycline-induced cardiotoxicity.

SUMMARY

Disclosed are methods, pharmaceutical compositions, kits, and systems for treating or preventing cardiotoxicity in a subject undergoing treatment with an anthracycline chemotherapeutic agent. The methods, pharmaceutical compositions, kits, and systems typically include or utilize a therapeutic agent that inhibits the activity or expression of the solute transporter SLC28A3.

In an aspect of the current disclosure, methods of treating a subject having a cell proliferative disease or disorder are provided. In some embodiments, the methods comprise administering to the subject: (i) an effective amount of an anthracycline for treating the cell proliferative disease or disorder; and (ii) an effective amount of a therapeutic agent that inhibits the activity or expression of the SLC28A3 transporter for inhibiting cardiotoxicity induced by the anthracycline. In some embodiments, the cell proliferative disease or disorder is cancer. In some embodiments, the cell proliferative disease or disorder is leukemia. In some embodiments, the anthracycline is selected from doxorubicin, daunorubicin, epirubicin, or idarubicin. In some embodiments, the anthracycline is doxorubicin. In some embodiments, an effective amount comprises a dose of the anthracycline that exceeds a recommended cumulative dose for the subject. In some embodiments, the therapeutic agent is an SLC28A3 inhibitor selected from the group consisting of butoconazole, tetracaine, propofol, and desipramine. In some embodiments, the SLC28A3 inhibitor is desipramine. In some embodiments, the subject has the polymorphic allele $SLC^{ref}$. In some embodiments, the therapeutic agent inhibits the expression of the SLC28A3 transporter. In some embodiments, the therapeutic agent comprises an interfering RNA that inhibits the expression of the SLC28A3 transporter.

In another aspect of the current disclosure, methods for treating a subject having a cell proliferative disorder, wherein the subject has a polymorphic allele $SLC^{ref}$ are provided In some embodiments, the methods comprise: (a) administering to the subject a cumulative dose of an anthracycline as follows: doxorubicin, wherein the cumulative dose is greater than about 400 mg/m$^2$; daunorubicin, wherein the cumulative dose is greater than about 600 mg/m$^2$; epirubicin, wherein the cumulative dose is greater than about 900 mg/m$^2$; idarubicin administered intravenously, wherein the cumulative dose is greater than about 150 mg/m$^2$; or idarubicin administered orally, wherein the cumulative dose is greater than about 150 mg/m$^2$; and (b) administering a therapeutic agent that inhibits the activity or expression of the SLC28A3 transporter. In some embodiments, the subject has at least one copy of the $SLC^{ref}$ allele. In some embodiments, the cell proliferative disease or disorder is cancer. In some embodiments, the cell proliferative disease or disorder is leukemia. In some embodiments, the therapeutic agent is an SLC28A3 inhibitor selected from the group consisting of butoconazole, tetracaine, propofol, and desipramine. In some embodiments, the SLC28A3 inhibitor is desipramine. In some embodiments, the therapeutic agent comprises an interfering RNA that inhibits the expression of the SLC28A3 transporter.

In another aspect of the current disclosure, kits or treatment systems are provided. In some embodiments, the kits or treatment systems comprise as components: (i) an anthracycline chemotherapeutic agent; and (ii) a therapeutic agent that inhibits the activity or expression of the SLC28A3 transporter. In some embodiments, the therapeutic agent that inhibits the activity or expression of the SLC28A3 transporter is an SLC28A3 inhibitor selected from the group consisting of butoconazole, tetracaine, propofol, and desipramine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A, 2B, 2C, 2D, 2E, and 2F. SLC28A3 expression affects the severity of DIC by regulating DOX uptake into cardiomyocytes. A, Validation of CRISPR/Cas9-mediated SLC28A3 knockout (KO) in an isogenic hiPSC line detected by Sanger sequencing, showing 8 bp deletion downstream of the transcription start site (TSS). PAM, protospacer adjacent motif. B, Demonstration that 91% of the cell population acquire the introduced deletion. C, Validation of KO and AAVS1-based SLC28A3 overexpression (OE) by western blot and RT-PCR. D, Effect of DOX (72 h) on viability in ISO (n=45), ISO-OE (n=14), and ISO-KO (n=6) hiPSC-CMs. E, Effect of doxorubicin (72 h) on apoptosis measured by activated caspase 3/7 in ISO (n=8), ISO-OE (n=10), and ISO-KO (n=6) hiPSC-CMs. F, Assessment of DOX uptake via measurement of DOX intrinsic fluorescence using flow cytometry-based assay (n=6-9). n=full independent experimental replicates, Error bars, s.e.m, *P≤0.05, P≤0.01, *P≤0.001, ****P≤0.0001 by unpaired two-tailed Student's t-test (f). For (d and e) log-logistic non-linear regression model was used to estimate the value of the four parameters, and t-statistic was used to test for significant difference in LD$_{50}$ between different groups.

FIGS. 3A, 3B, 3C, 3D, 3E, and 3F. Fine-mapping at the SLC28A3-SLC28A3-AS1 locus identifies rs11140490 as the potential causal cardioprotective variant. A, Location of the Hap$^{SLC28A3}$ comprising 24 SNPs that are co-inherited only in SLC$^{var}$ protected patients. SNP rs11140490 marked by red rectangle is located at the splice site of the first exon of an overlapping long non-coding RNA, SLC28A3-AS1 (adapted from Magdy et al.[29]). B, Consequence of co-inherited Hap$^{SLC28A3}$ SNPs (n=24). C, Overall prioritization of candidate causal SNPs based on functional annotation analyses including, eQTL annotation, chromatin regulatory analyses, and overlapping with regulatory regions (RR) in cardiac tissues. FA, functional annotation (adopted from Magdy et al.[29]). D, Editing of rs11140490 (CT>TT) in two patient-specific hiPSC lines using cytosine base editor (Target-AID-NG), rs11140490 is marked by red asterisk. E, Effect of DOX (72 h) on viability in SLC$^{var-rs11140490\ (CT)}$ (2 lines, n=31) and SLC$^{var-rs11140490(CT>TT\ edited)}$ (2 lines, n=75) hiPSC-CMs. F, Assessment of DOX uptake via measurement percentage of cells with DOX intrinsic fluorescence using flow cytometry-based assay in SLC$^{var-rs11140490\ (CT)}$ and SLC$^{var-rs11140490(CT>TT\ edited)}$ (n=4). n=full independent experimental replicates, Error bars, s.e.m, *P≤0.05, P≤0.01, *P≤0.001, ****P≤0.0001 by unpaired two-tailed Student's t-test (F). For (E) log-logistic non-linear regression model was used to estimate the value of the four parameters, and t-statistic was used to test for significant difference in LD$_{50}$ between different groups.

FIGS. 4A, 4B, 4C, 4D, 4E, 4F, and 4G. The cardioprotective role of SLC28A3-AS1. A, Relative Expression of SLC28A3-AS1 in ISO hiPSC compared to ISO transduced by viral plasmid encoding SLC28A3-AS1 cDNA to over-express SLC28A3-AS1 (ISO$^{SLC28A3-AS1}$) assessed by RNA-Seq (n=2). B, SLC28A3 relative expression in ISO and ISO$^{SLC28A3-AS1}$ hiPSC-CMs (n=5-11) assessed by real-time PCR. C, Effect of SLC28A3-AS1 overexpression on cell viability after DOX (72 h) treatment, ISO (n=17), ISO$^{SLC28A3-AS1}$ (n=12). D, Effect of SLC28A3-AS1 overexpression on DOX uptake 1 h and 3 h post DOX treatment (n=6-14). E, Relative human cardiomyocyte expression of SLC transporters (n=12) previously identified as transporting DOX or a DOX metabolite and/or by genetic associations with DOX clinical outcomes. Red dashed line denoted for the expression cutoff for SLC transporter selection. F, Effect of knocking out DOX-relevant SLC transporters on DOX uptake into patient-derived cardiomyocytes [SLC28A3$^{KO}$, SLC22A4$^{KO}$, SLC22A3$^{KO}$, and SLC22A17$^{KO}$ (n=5-13)]. G, Effect of knocking out potential cardiac-specific SLC transporters on cell viability after DOX treatment [SLC28A3$^{KO}$ (n=14), SLC22A4$^{KO}$ (n=58), SLC22A3$^{KO}$ (n=17), and SLC22A17$^{KO}$, (n=10), ISO (n=128)]. n=full independent experimental replicates, Error bars, s.e.m, *P≤0.05, P≤0.01, *P≤0.001, ****P≤0.0001 by unpaired two-tailed Student's t-test (B, D, and F). For (C and G) log-logistic non-linear regression model was used to estimate the value of the four parameters, and t-statistic was used to test for significant difference in LD$_{50}$ between different groups.

FIGS. 5A, 5B, 5C, 5D, 5E, 5F, and 5G. Multi-modality drug screening identifies desipramine as a novel effective cardioprotectant against DIC. A, Prestwick drug library screening (n=1219) in relation to DIC (n=5). All drugs were used at 3 μM. Red dashed line represents cell viability 72 h post DOX (10 μM) treatment; the top ten significant cardioprotective drugs based on cell viability are labeled. B, Bar plot showing top ten significant cardioprotective (based on P value) compared to DOX alone (72 h, 10 μM) treated cells. Non-FDA-approved drugs are represented by teal bars. C, Further validation of top FDA-approved drugs (identified from the Prestwick library screening) against 10 log-doses of doxorubicin. LD$_{50}$, median lethal dose. D, Effect of co-treatment of desipramine (3 μM) and doxorubicin (72 h) on hiPSC-CM viability [DOX (n=42), DOX+DESP (n=35)]. E, Percent change in ventricular fraction shortening (FS) normalized to baseline, after 3 weeks of doxorubicin treatment (3 mg/kg, ip, n=10) compared co-treatment (n=8) of desipramine (20 mg/kg/day, Alzet pump) and doxorubicin (3 mg/kg, ip) in mice. F, Ventricular fractional shortening at baseline, 1-, 2-, 3-weeks post treatment. G, Assessment of cell viability of MCF breast cancer cell line after 72 h of DOX and desipramine (DESP) cotreatment (n=12-20). f=full independent experimental replicates, Error bars, s.e.m, *P<0.05, P≤0.01, *P<0.001, ****P<0.0001 by unpaired two-tailed Student's t-test (A-C and E) and by ANOVA with post-hoc testing (F). For (D and G) log-logistic non-linear regression model was used to estimate the value of the four parameters, and t-statistic was used to test for significant difference in $LD_{50}$ between different groups.

Figure 6A:
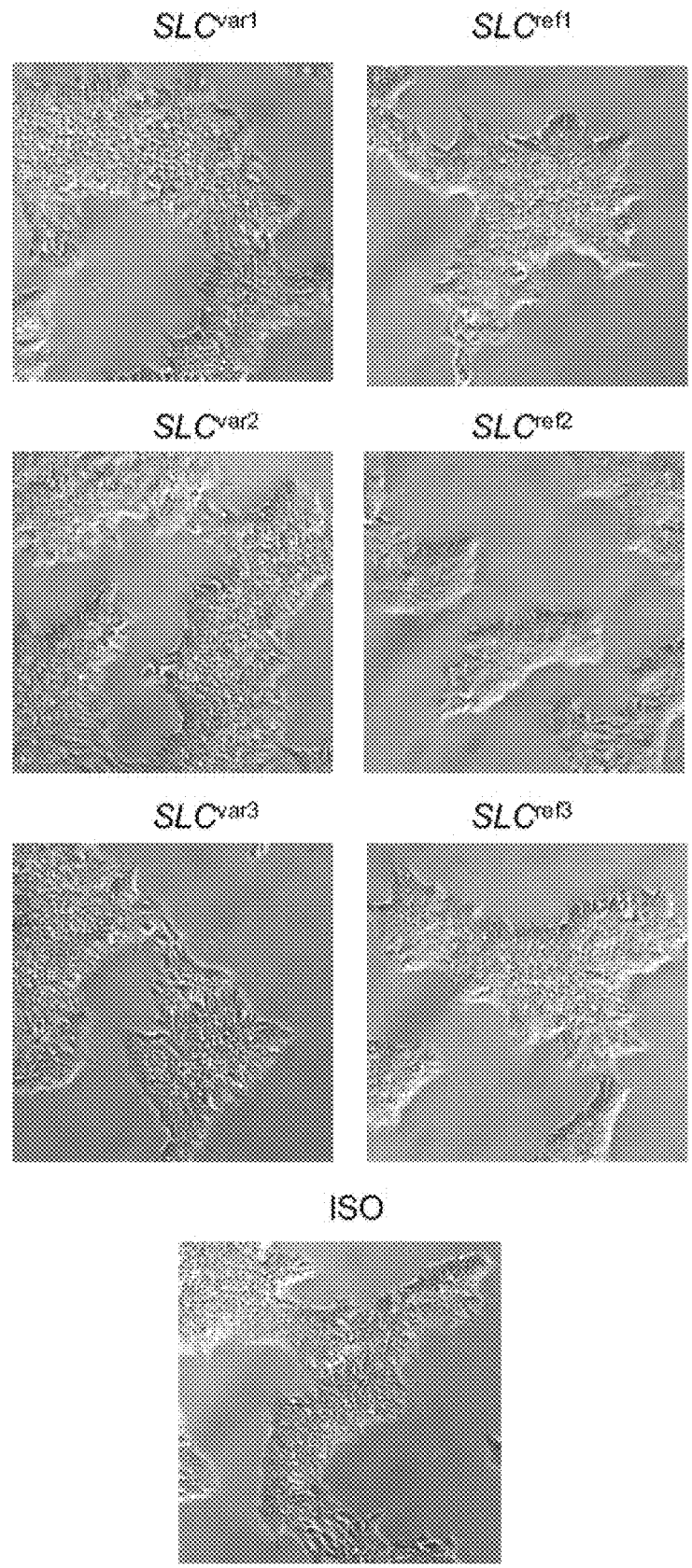
Figure 6B:
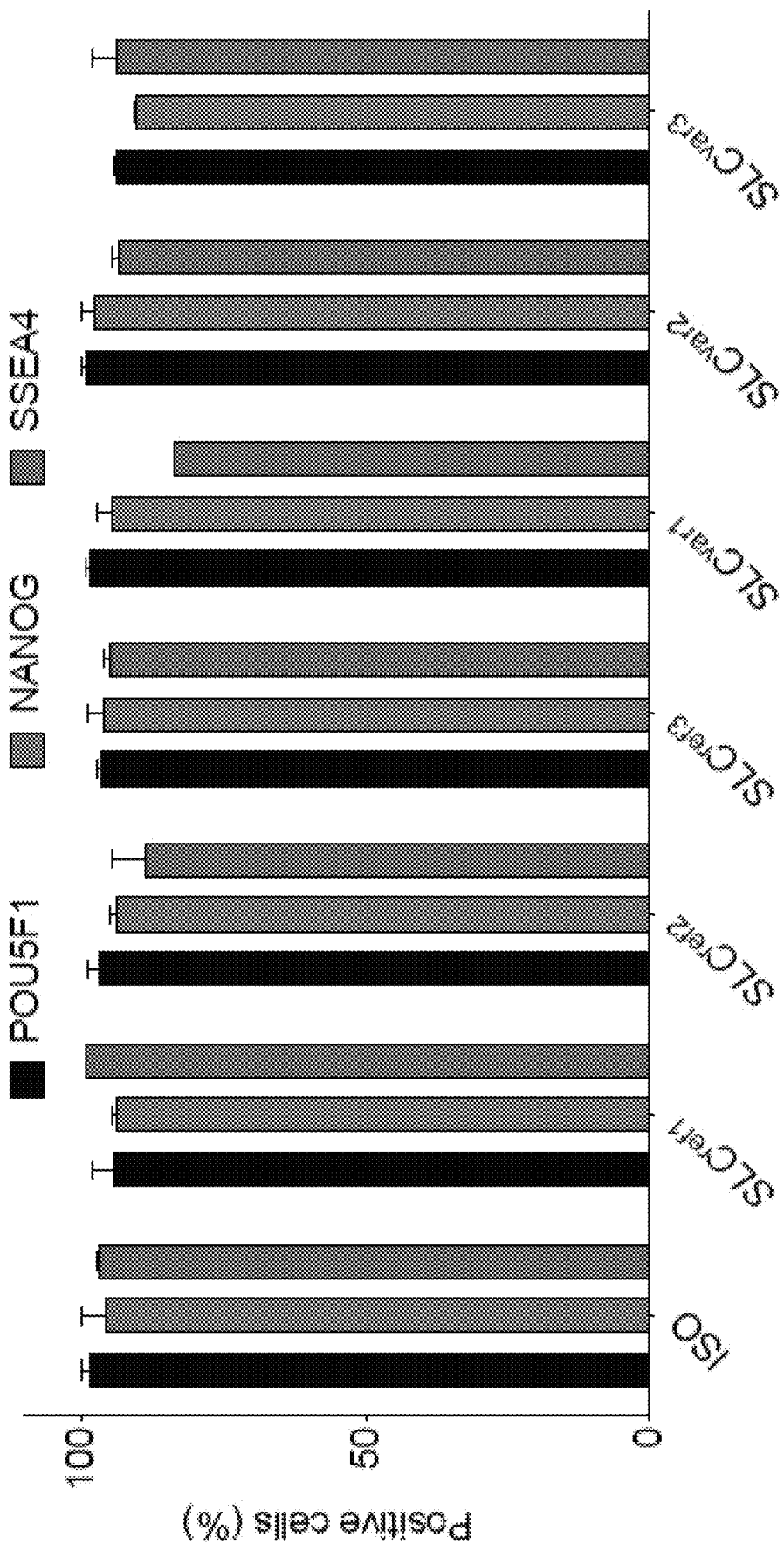
Figure 6C:
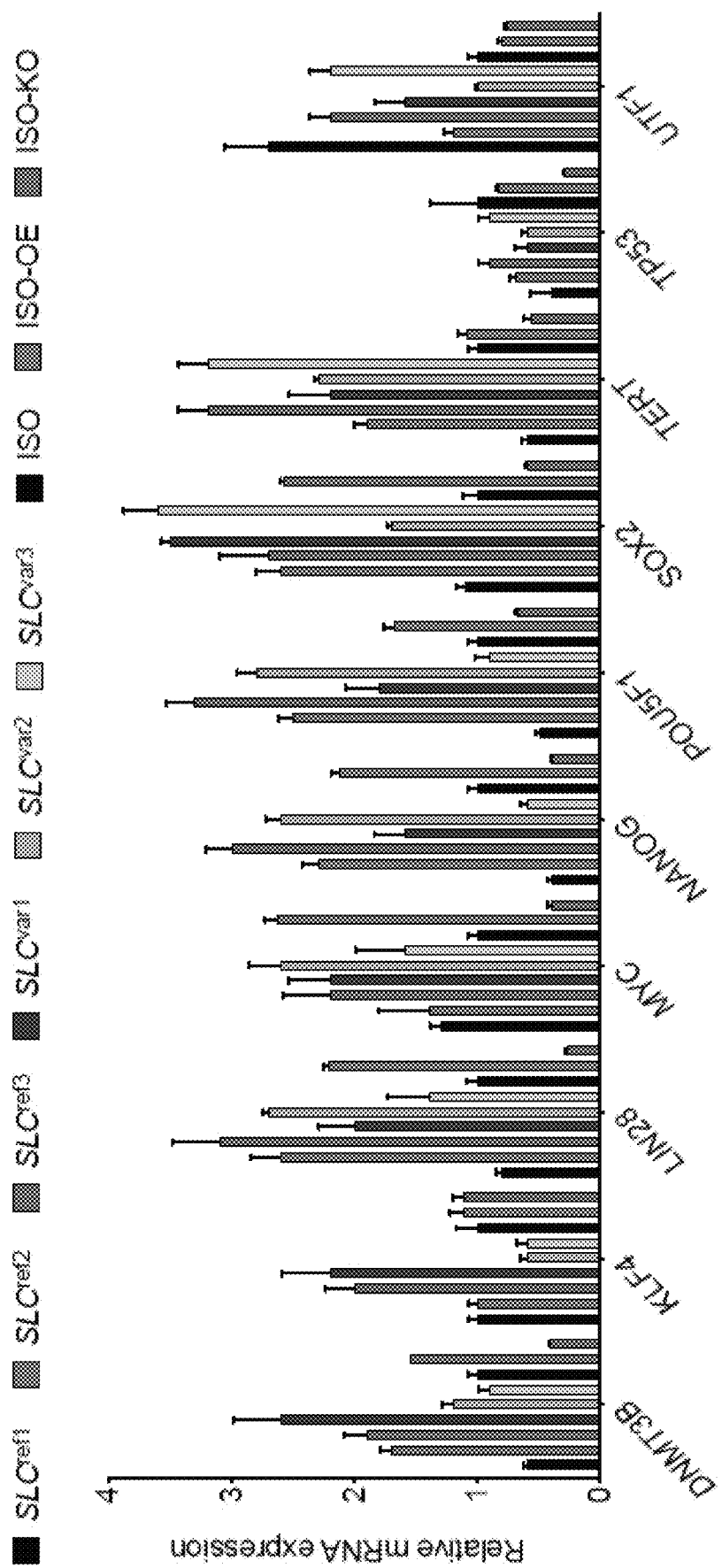

FIGS. 6A, 6B, and 6C. Generation and characterization of patient-specific hiPSCs. A, Phase contrast images of patient-specific hiPSC lines derived under chemically defined conditions. Scale bar, 100 μm. B, Flow cytometry analysis of markers of undifferentiated cells, POU5F1, NANOG, and SSEA4, in all hiPSC lines. C, Real-time PCR assessment of the expression levels of genes associated with the undifferentiated state in all hiPSC lines, relative to control isogenic hiPSC line. n=3 replicates for each hiPSC line. Error bars represent s.e.m. of experimental replicates.

Figure 7:
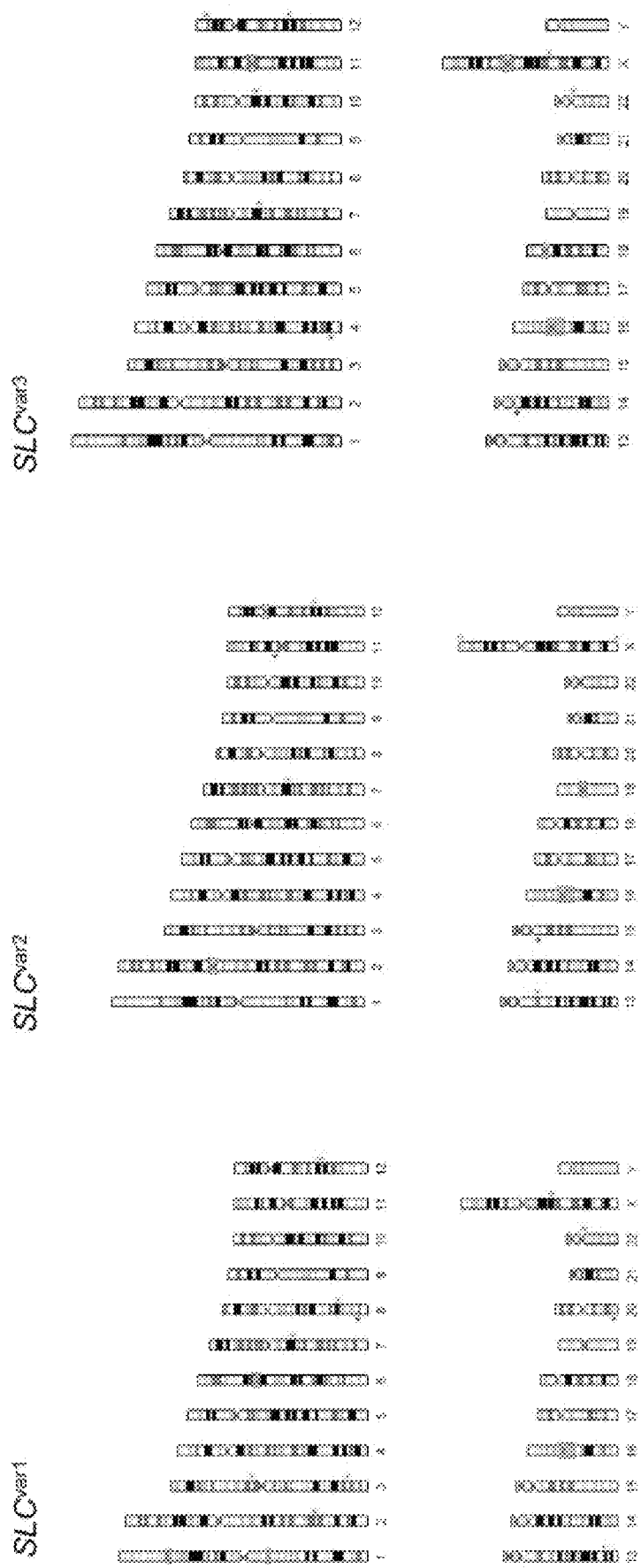
Figure 7:
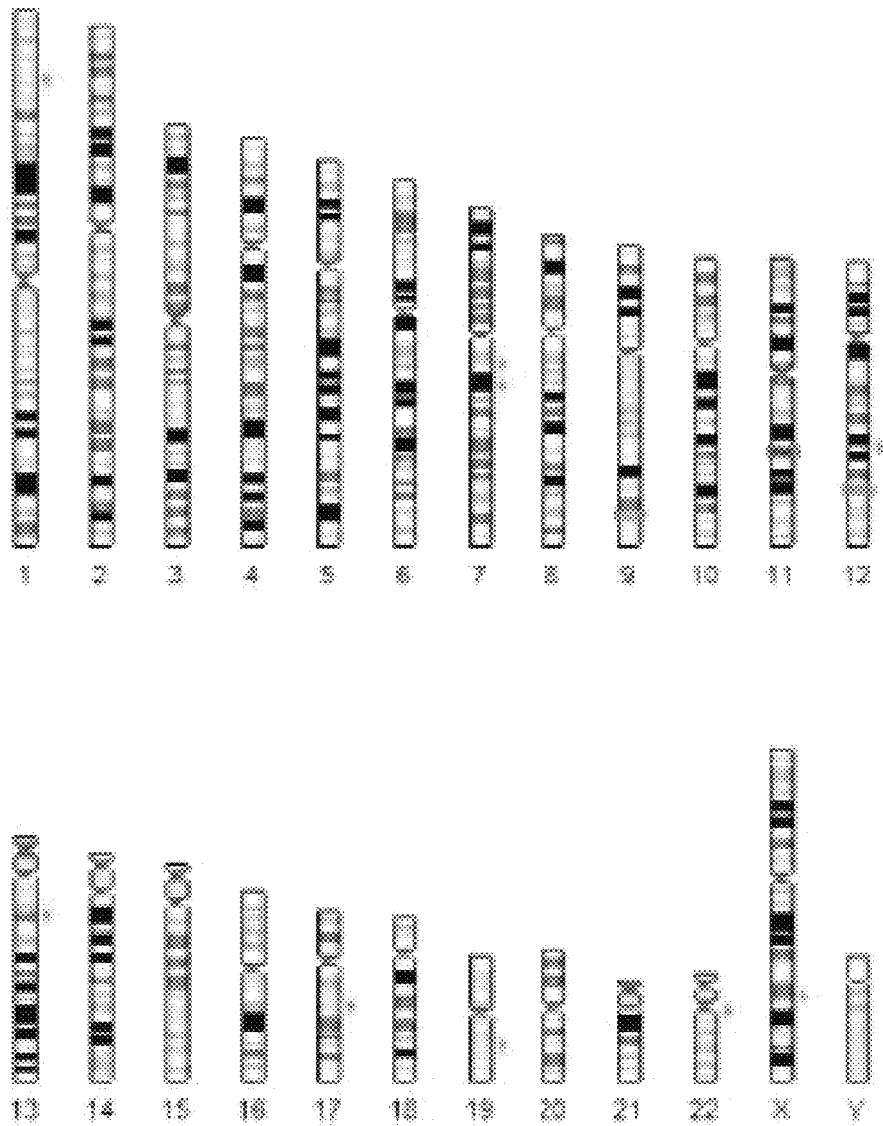
Figure 8A:
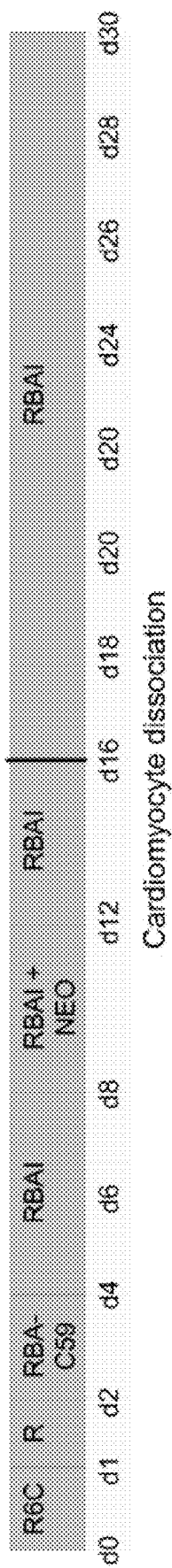
Figure 8C:
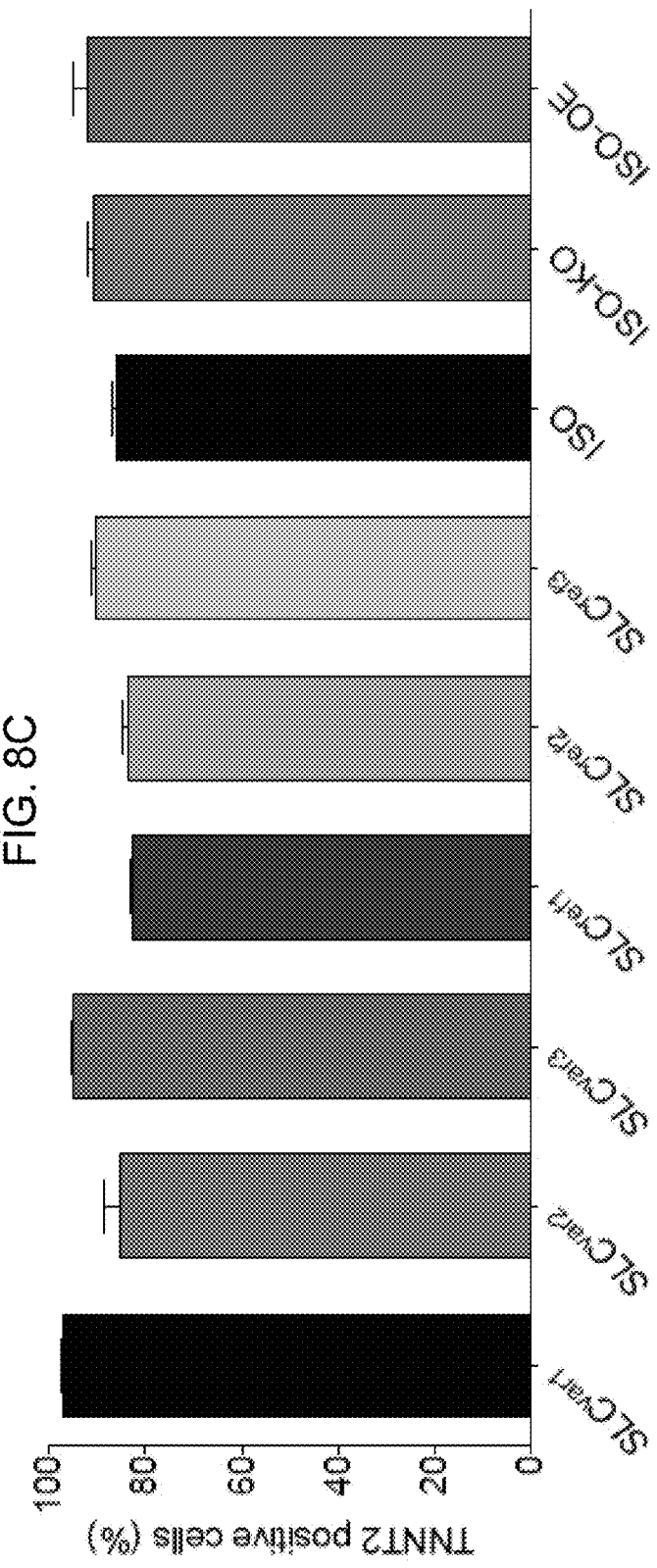
Figure 8B:
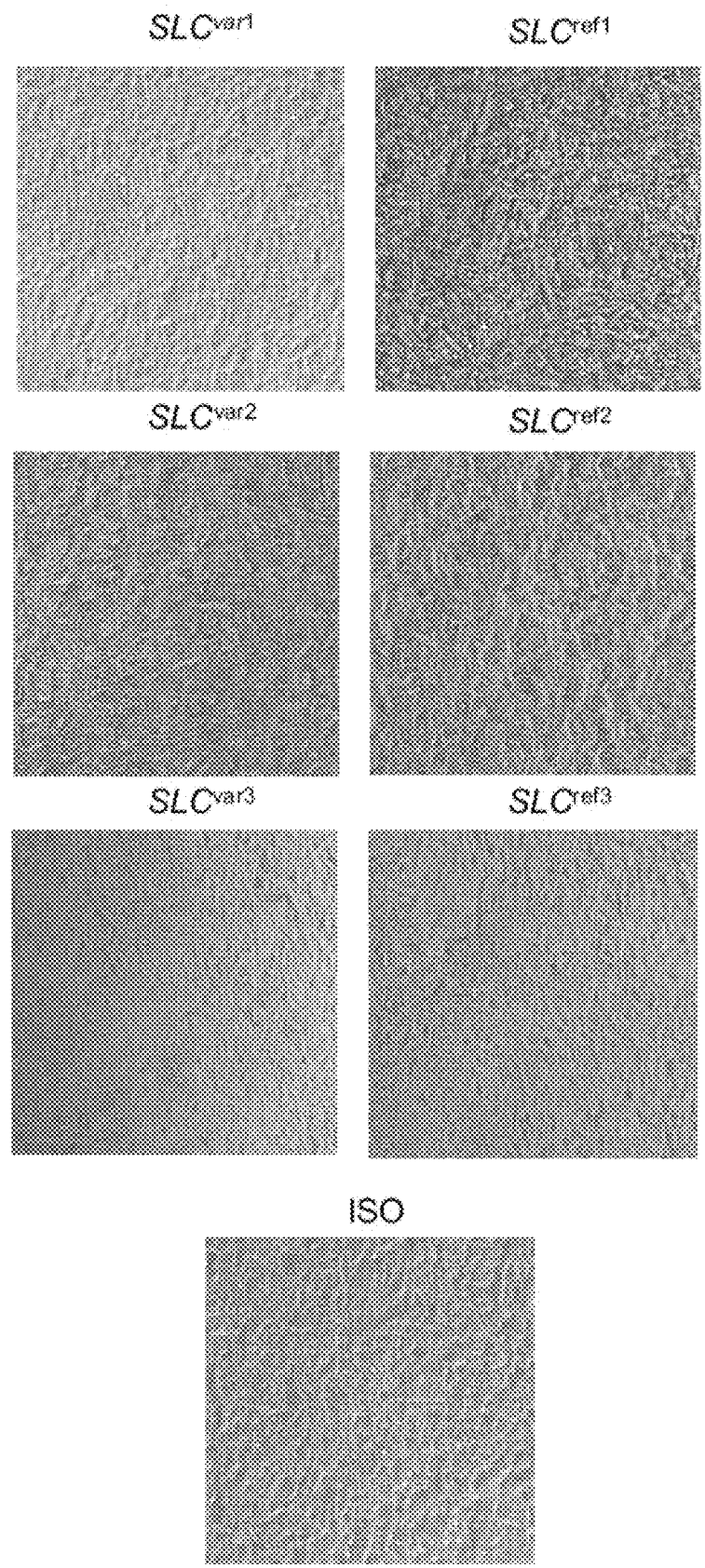
Figure 8D:

FIG. 7. Karyotype analysis of patient-specific hiPSC lines. SNP-based karyotype analysis of all patient-derived hiPSC lines (passage >20) demonstrating normal karyotype after reprogramming. Karyotyping was assessed using a whole-genome Infinium HumanCytoSNP-12 BeadChip Array (Illumina) covering 300,000 SNPs.

FIGS. 8A, 8B, 8C, and 8D. Generation and characterization of patient-specific hiPSC-CMs. A, Schematic of our cardiac differentiation protocol (details in Methods). B, Representative phase contrast images of day 30 cardiomyocyte monolayers differentiated from all hiPSC lines. Scale bar, 100 μm. C, Flow cytometry analysis for the percentage of the cardiac troponin T (TNNT2) positive cells derived from all hiPSC lines, n=3 replicates for each line. Error bars represent s.e.m. of experimental replicates. D, Representative immunofluorescent staining images for cardiac markers troponin T (TNNT2) and α-actinin (ACTN2). Scale bar, 25 μm.

FIGS. 9A, 9B, 9C, 9D, 9E, 9F, and 9G. SLC28A3 gene resequencing. A, Exemplary agarose gel picture for all nine overlapping SLC28A3 amplicons generated from one sample. L, ladder; 1-9, amplicons one to nine. B, Exemplary pre-nanopore sequencing amplicon validation by sanger sequencing for amplicon number four (Amp04). Top panel shows the first ~600 bp of generated amplicon four (AMP04) aligned to its reference sequence (AMP04 ref). Bottom panel shows a zoom-in view for the first ~100 bp of generated amplicon four perfectly matching its reference sequence. C, Long range PCR-based target enrichment for SLC28A3 amplicons aligned to reference human genome (GRCh38) showing depth of coverage peaks at chr9: 84,274,029-545 84,349,802. D, Zoom-in view at locus chr9: 84,274,029-84,349,802 encompassing SLC28A3. E, Consequence and location of identified SNPs (n=133). F, Functional chromatin regulatory analysis for the candidate SNPs showing the number of chromatin binding sites significantly altered by candidate SNPs. G, Effect of candidate SNPs, rs11140490, rs4877835, and rs7853758 on chromatin feature binding sites. Log 2 fold change measure the fold change in the probability of observing a binding site for relevant chromatin feature between reference and alternative allele for a particular SNP (adapted from Magdy et al.[23]).

Figure 10A:
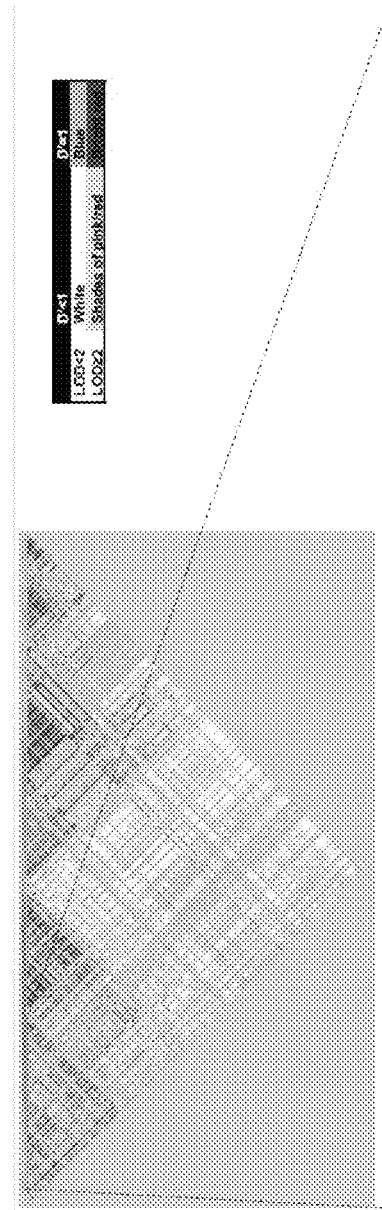
Figure 10B:
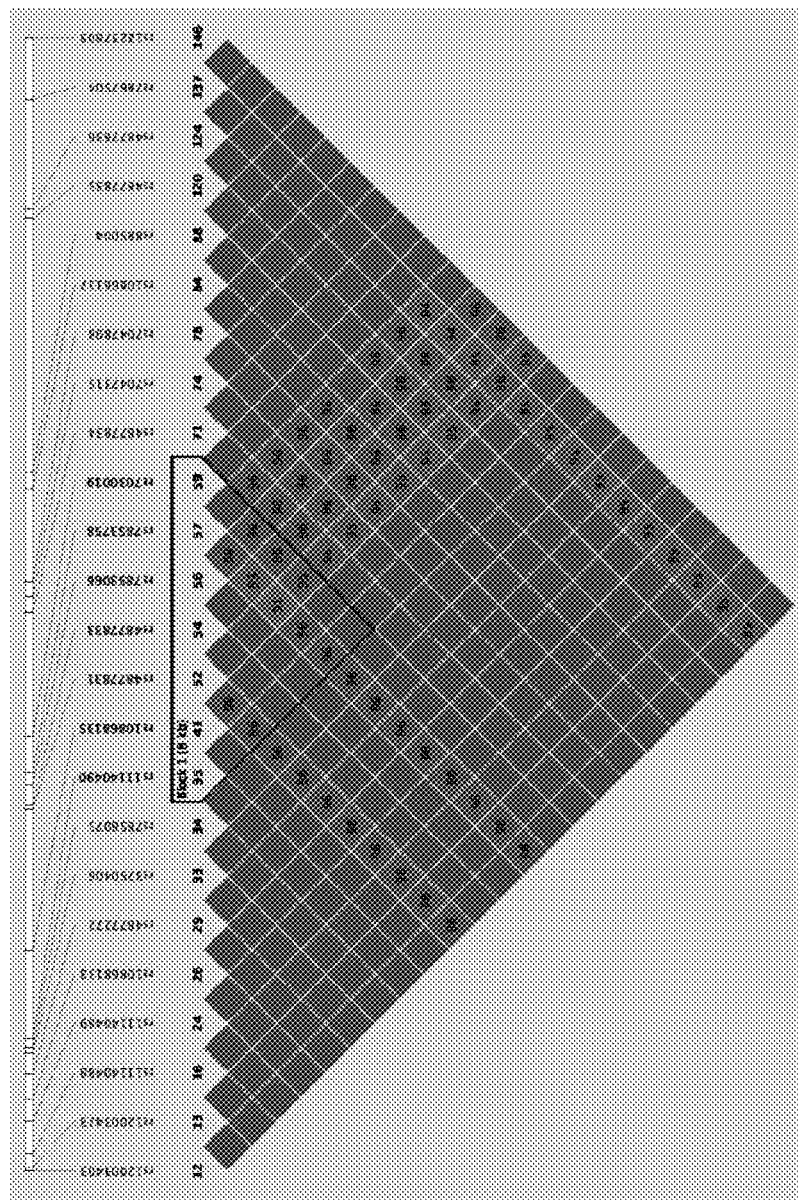

FIGS. 10A, 10B, and 10C. Haplotype structure at SLC28A3/SLC28A3-AS1 locus. A, Pairwise linkage disequilibrium (D') for all SNPs spread over ~100 kb encompassing SLC28A3 SL28A3-AS1 locus. The linkage disequilibrium (D') is indicated in the small boxes colored red or blue (a color legend is provided). LOD, log of the likelihood odds ratio. B, LD haplotype structure for HapSLC28A3 that is spread over 32 kb and comprising 24 SNPs that are co-inherited only in cardio protected patients. The reference SNP numbers (rs) are indicated on top. HapSL28A3-AS1 (outlined by black triangle) spread over 8 kb and is composed of seven SNPs that are located within a long non-coding RNA, SL28A3-AS that overlaps with SLC28A3. C, Haplotype structure and allelic frequency of HapSL28A3-AS1 showing seven haplotype structures, [Hap-ISL28A3-AS1 to Hap-VIISL28A3-AS1]. Each SNP is labeled as follow; rs id (SNP number on the LD block in FIG. b, reference allele>variant allele). SNP rs7853758 (in bold) is the primary GWAS hit. For each SNP, variant alleles are in red (adapted from Magdy et al.[23]).

Figure 11A:
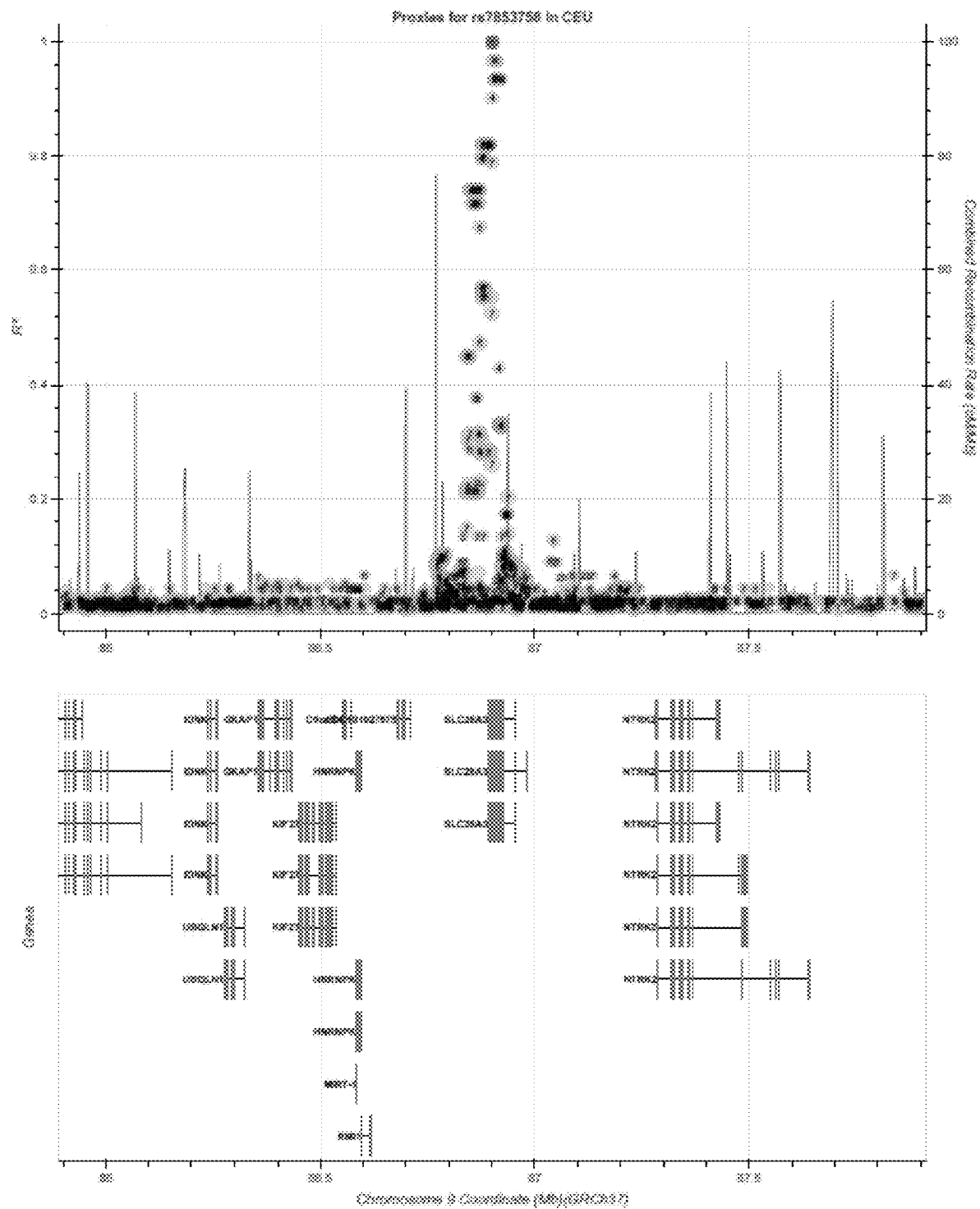
Figure 11B:
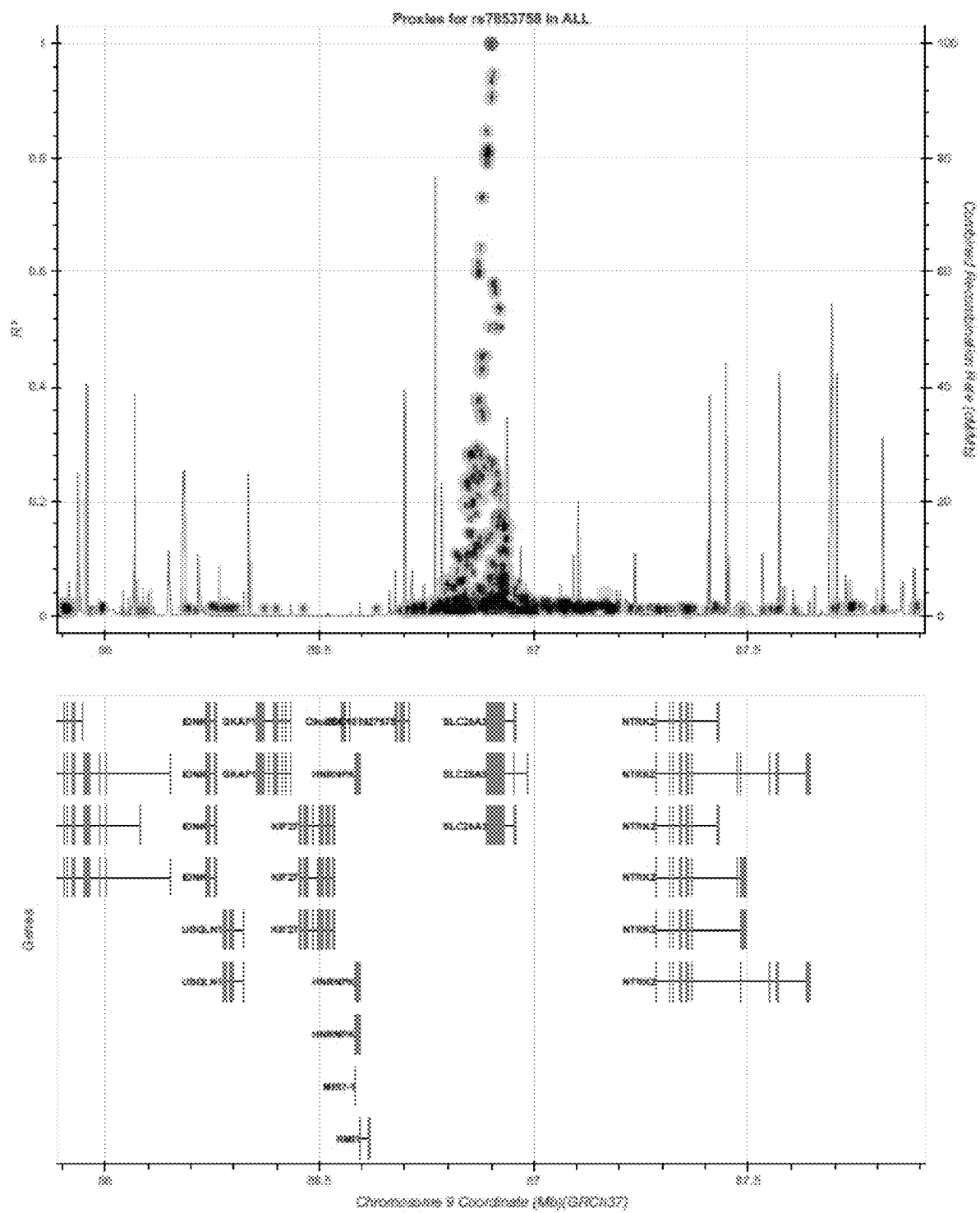

FIGS. 11A and 11B. Extended Linkage disequilibrium (LD) analysis over 2 Mb on chromosome 9. Linkage disequilibrium for variants located within 1 Mb up and downstream the SLC28A3/SLC28A3-AS1 locus in CEU/European population (A) and in All ethnicity population (B). For each plot the LD Co-efficient (R2) is represented on the left Y-axis and the genomic coordinates are represented on the x-axis. Each yellow circle denotes for a single SNP within the target locus. The original CGAS hit, rs7853758 is represented by a purple circle.

Figure 12A:
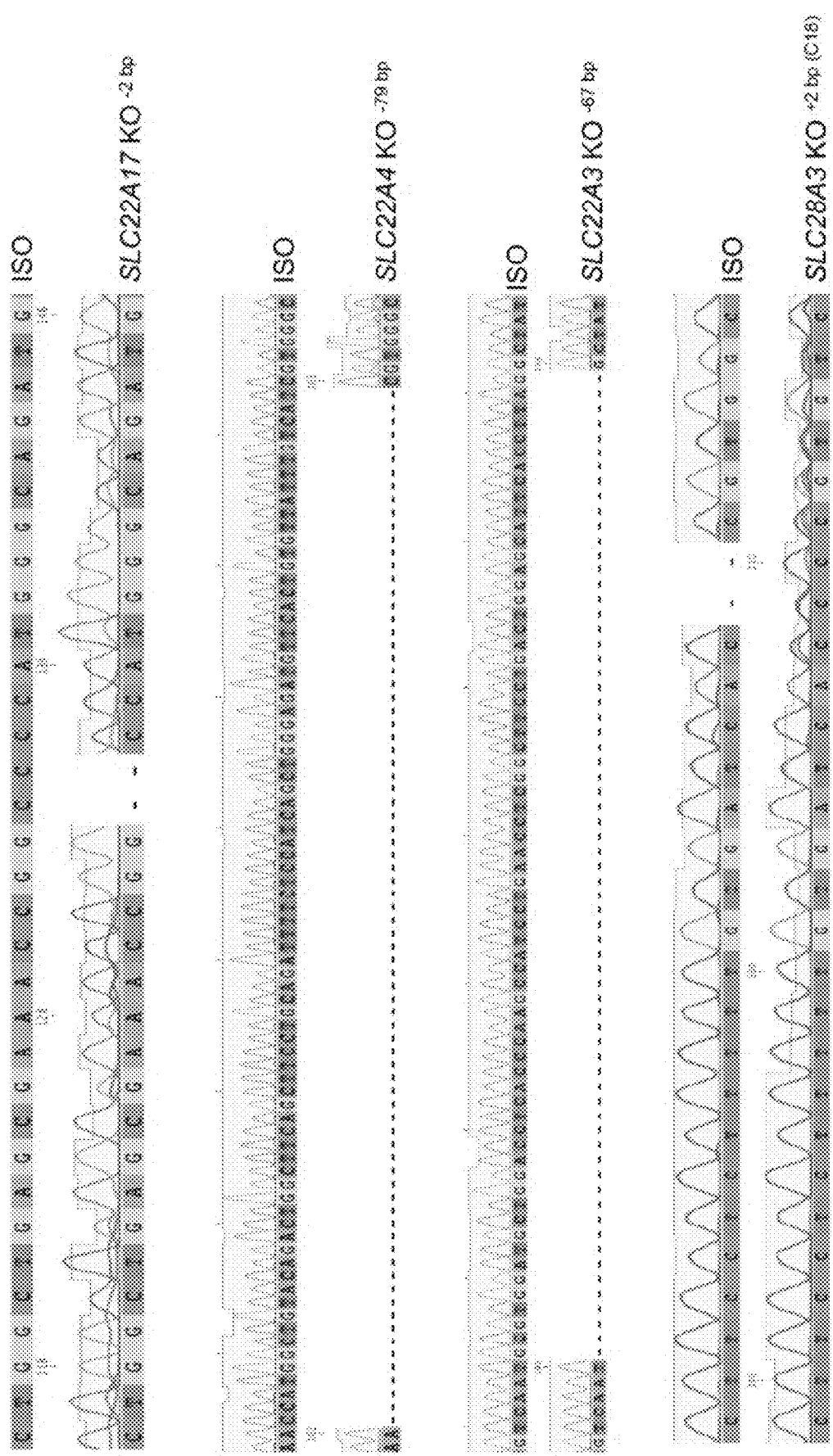
Figure 12B:
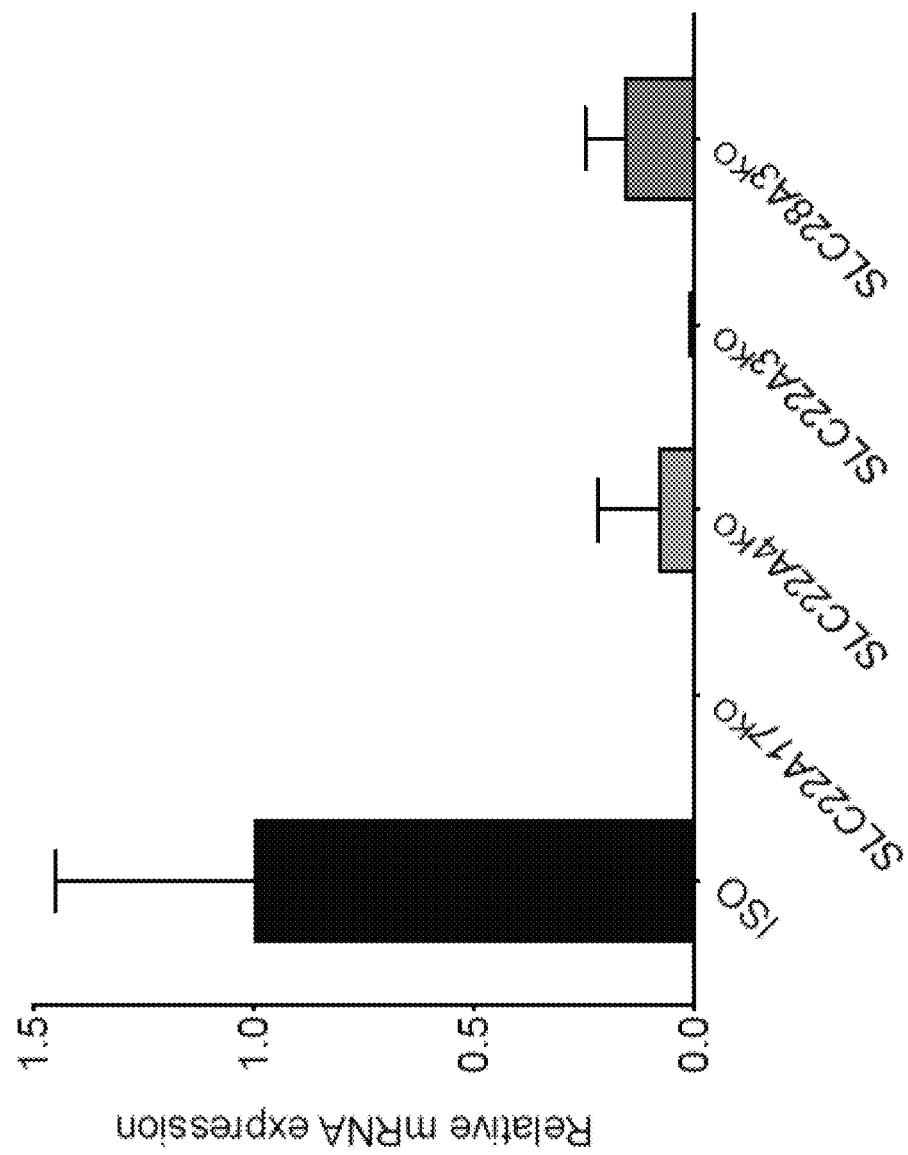

FIGS. 12A and 12B. Generation of DOX-relevant SLC transporter knockouts in an isogenic cell line. A, Validation of SLC transporters knockouts using Sanger sequencing showing disturbance on DNA level at target loci. B, and qPCR to quantify the mRNA expression of relevant transporters (n=3). n=full independent experimental replicates, Error bars, s.e.m.

FIGS. 13A, 13B, 13C, 13D, 13E, 13F, 13G, 13H, 13I, 13J, 13K, 13L, 13M, 13N, 13O, 13P, and 13Q. Assessment of the toxicity of the cherry-picked SLC transporter modulators in hiPSC-CMs. a-q, The effect of 17 different transporter inhibitors on patient derived hiPSC-CMs viability were assessed 72 h post treatment. The drugs assessed were; A, cyclosporin A, B, cimetidine, C, entecavir, D, rifampicin, E, nilotinib, F, phlorizin, G, indomethacin, H, quinidine, I, rifamycin, J, verapamil, K, bosutinib, L, dasatinib, M, vadentanib, N, pazopanib, O, sunitinib, P, sulfobromophthalein, and Q, desipramine.

Figure 14A:
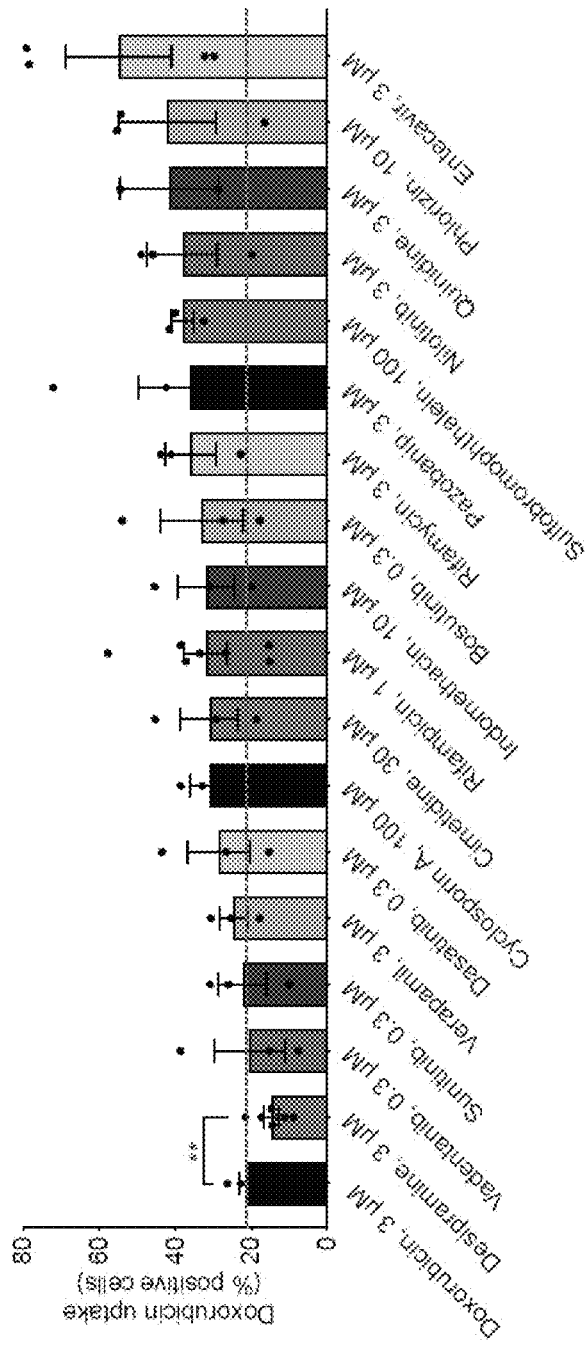
Figure 14B:
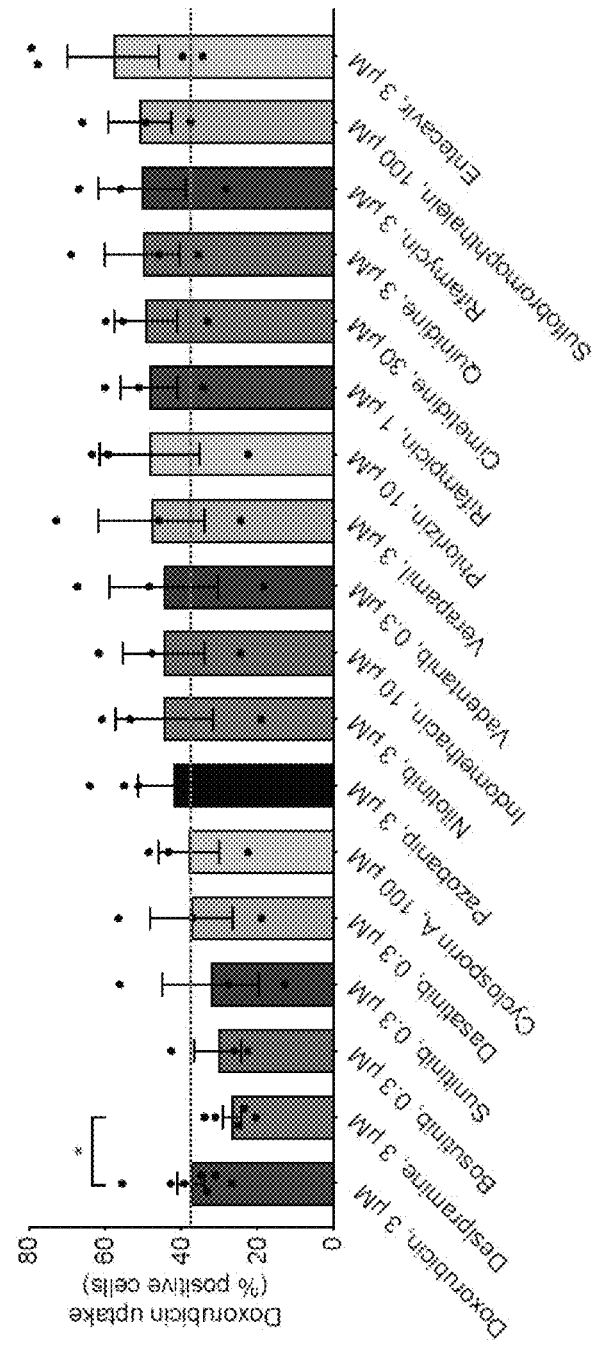
Figure 14C:
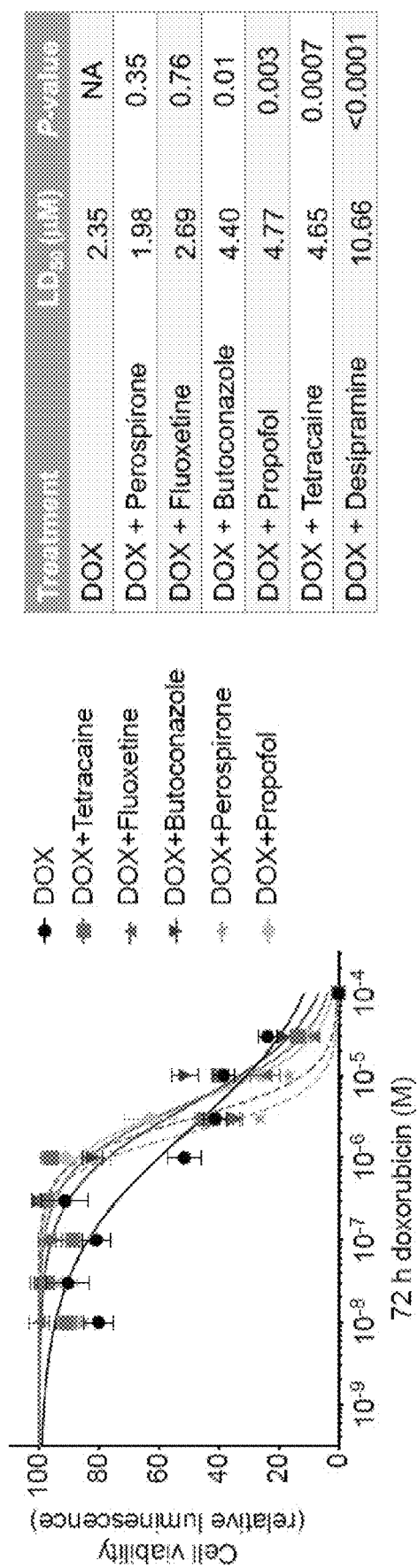

FIGS. 14A, 14B and 14C. Screening of cherry-pick SLCs modulators in relation to DIC in hiPSC-CMs. A-B, The effect of 17 SLC transporter modulators on DOX intracellular accumulation in hiPSC-CMs by quantification of DOX intrinsic fluorescence using a flow cytometry-based assay (n=3-6). DOX uptake was quantified 1 h (A) and 3 h (B) post DOX treatment. C, Validation of Prestwick drug library screening-identified top FDA-approved cardioprotectants against 10 log-doses of doxorubicin. n=full independent experimental replicates, Error bars, s.e.m, *P<0.05, P≤0.01, *P≤0.001, ****P<0.0001 by unpaired two-tailed Student's t-test (a-b). For (c) log-logistic non-linear regression model was used to estimate the value of the four parameters, and t-statistic was used to test for significant difference in $LD_{50}$ between different groups.

FIGS. 15A, 15B, 15C, 15D, 15E, 15F, 15G, and 15H. Desipramine does not attenuate doxorubicin cytotoxicity in cancer cell lines. A-H, Assessment of cell viability after after 48 h of doxorubicin and desipramine co-treatment in A HEPG2. B, DLD1. C, LNCAP. D, SK-UT-1. E, HeLa. F, U2OS. G, Hs 578T. H, and MDA-MB-231 (n=12-20). DESP, desipramine. n=full independent experimental replicates, Error bars, s.e.m, Log-logistic non-linear regression model was used to estimate the value of the four parameters, and t-statistic was used to test for significant difference in $LD_{50}$ between different groups.

Figure 16A:
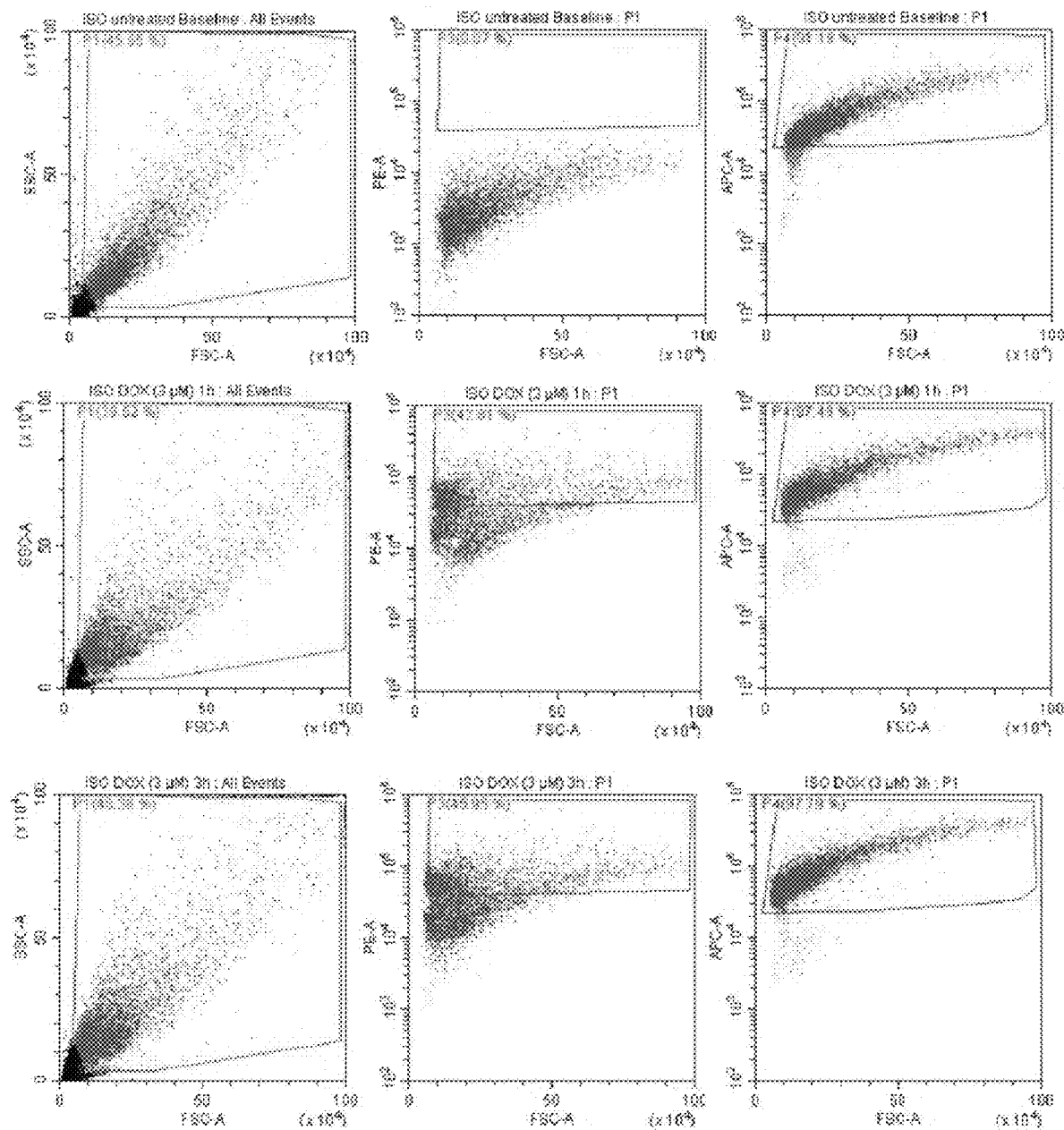
Figure 16B:
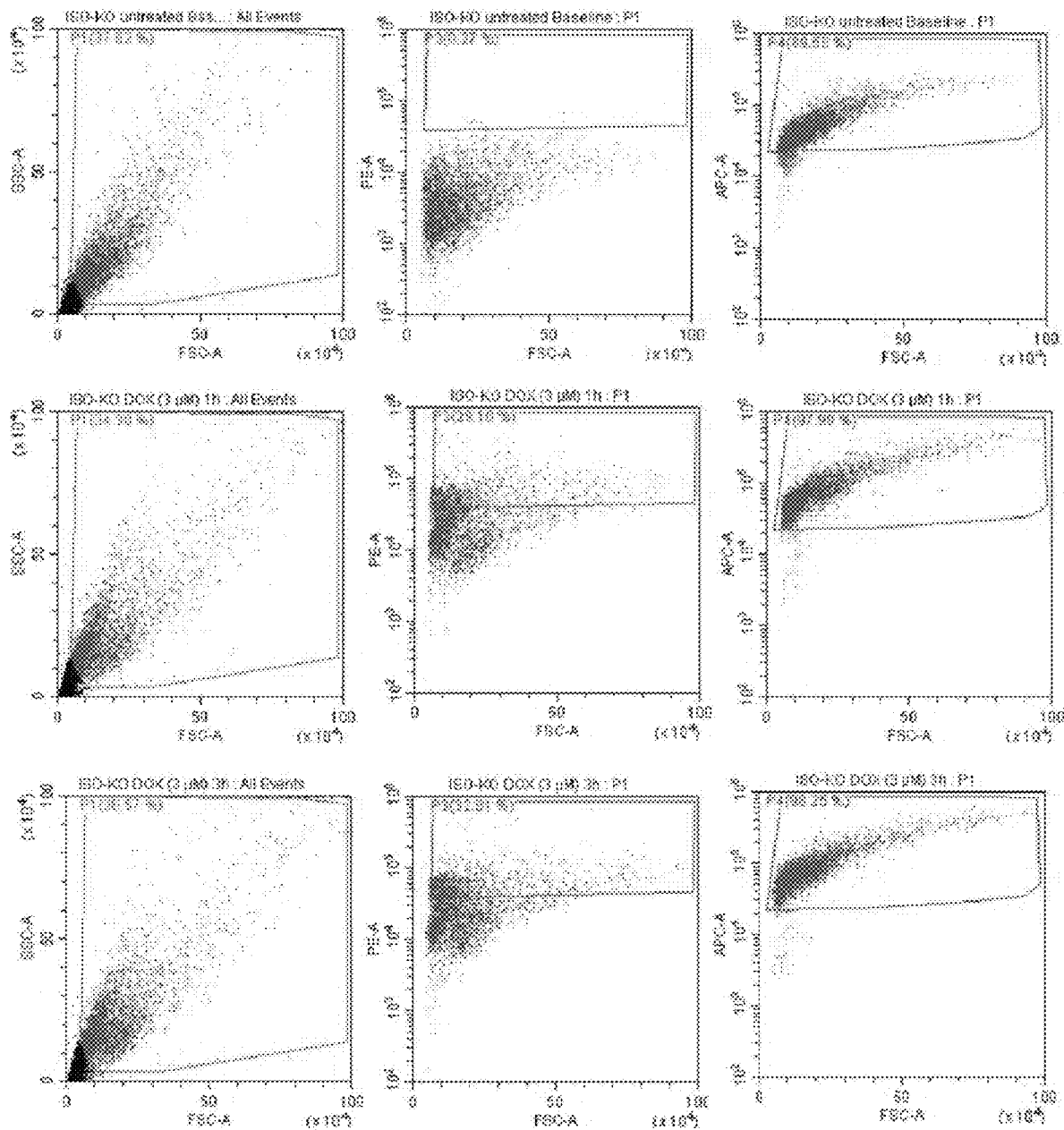
Figure 16C:
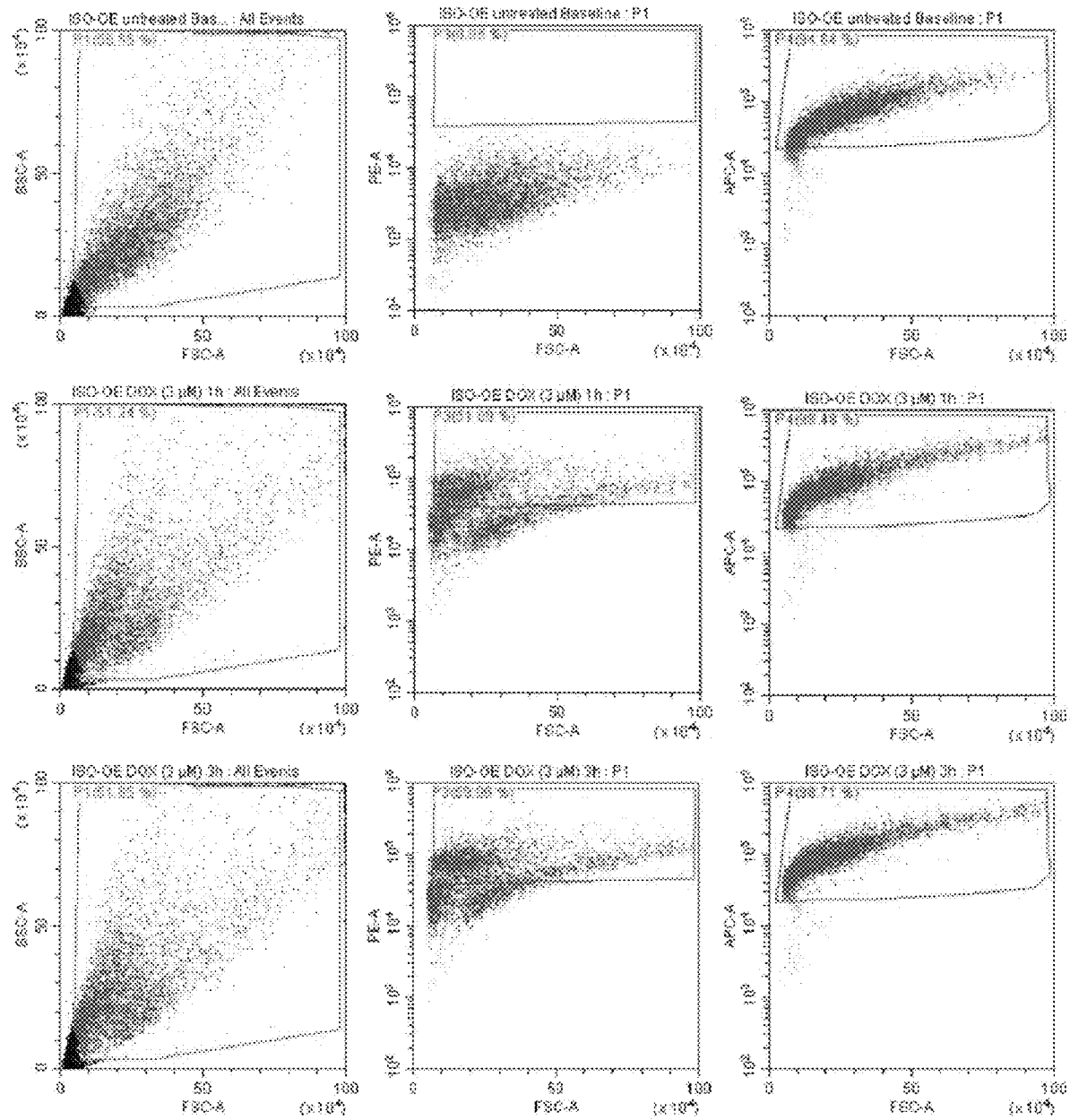

FIGS. 16A, 16B, and 16C. Exemplary flow cytometry plots for DOX uptake in hiPSC-CMs. Flow cytometry-based DOX uptake quantification in ISO (A), ISO-KO (B), and ISO-OE (C). For each subfigure, the top panel depicts DOX uptake in untreated cells at the baseline; the middle panel depicts DOX uptake 1 h post DOX treatment (3 μM); and the bottom panel depicts DOX uptake 3 h post DOX treatment (3 μM). P3 denotes DOX uptake (% positive cells) at baseline, 1 h, and 3 h post DOX treatment. P4 denotes live cells (% positive cells) at baseline, 1 h, and 3 h post DOX treatment.

FIGS. 17A, 17B, 17C, and 17D. Effect of doxorubicin treatment in hiPSC-CMs and mice. A, Comparison of hiPSC-CMs derived from three patients harboring the heterozygous rs7853758 variant and were protected from DIC after DOX treatment (SLCvar1 (n=37), SLCvar2 (n=26), SLCvar3 (n=63); collectively SLCvar), to hiPSC-CMs from three control patients who did not carry this protective SNP and developed DIC upon same DOX treatment (SLCref1 (n=30), SLCref2 (n=29), SLCref3 (n=22); collectively SLCref). B, Western blot showing SLC28A3 expression in SLCref (n=3), and SLCvar (n=3) hiPSC-CMs. C-D, representative echocardiography images for m hearts after 3 weeks of doxorubicin treatment (3 mg/kg, ip, n=10) compared co-treatment (n=8) of desipramine (20 mg/kg/day, Alzet pump) and doxorubicin (3 mg/kg, ip) showing an increased end-systolic dimension in the Dox group when compared to DOX+DESP group. n=full independent experimental replicates, Error bars, s.e.m, *P<0.05.

DETAILED DESCRIPTION

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "an inhibitor of SLC28A3" or "an anthracycline" should be interpreted to mean "one or more inhibitors of SLC28A3" and "one or more anthracyclines," respectively As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus ≤10% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment. A subject may include a subject of any age. In some embodiments, the subject in need thereof is not an adult (e.g., where the subject is a child).

A "subject in need of treatment" may include a subject having a disease, disorder, or condition that can be treated by administering to the subject one or more therapeutic agents as disclosed herein. A subject in need thereof may include a subject having or at risk for developing a cell proliferative disease or disorder such as cancer where the subject has been selected for treatment with an anthracycline chemotherapeutic agent. A subject in need thereof may include, but is not limited to, a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus) where the subject has been selected for treatment with an anthracycline chemotherapeutic agent. As such, methods of treating cancers are contemplated herein, including methods of treating cancers selected from, but not limited to any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus), where the subject is administered an anthracycline chemotherapeutic agent and a therapeutic agent that inhibits the activity or expression of the SLC28A3 transporter.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "pharmaceutical composition" may be defined as a composition that includes a therapeutically effective amount of a therapeutic agent(s) and a pharmaceutically acceptable carrier for delivering the therapeutic agent(s) to target cells or target tissue. As used herein, the term "pharmaceutically acceptable carrier" refers to a carrier for administration of a therapeutic agent which facilitates the delivery of the therapeutic agent to target cells or target tissue. Pharmaceutically acceptable carriers may include solid carriers and liquid carriers, optionally where the therapeutic agents are dissolved in the liquid carriers. As used herein, the term "therapeutically effective amount" refers to that amount of a therapeutic agent that provides a therapeutic benefit in the treatment, prevention, or management of a disease, disorder, or side-effects of treating a diseases or disorder (e.g., side-effect of treating cell proliferation diseases or disorders with anthracycline chemotherapeutic agents).

As used herein, the term "kit" or "system" refers to a combination of components, which may be utilized to achieve a specific purpose. For example, disclosed herein are kits and therapeutic systems that include an agent for treating cancer (e.g., an anthracycline chemotherapeutic agent) and a therapeutic agent that inhibits the activity or expression of the SLC28A3 transporter. In the disclosed kits or systems, the components may be packaged together or separately.

Figure 1A:
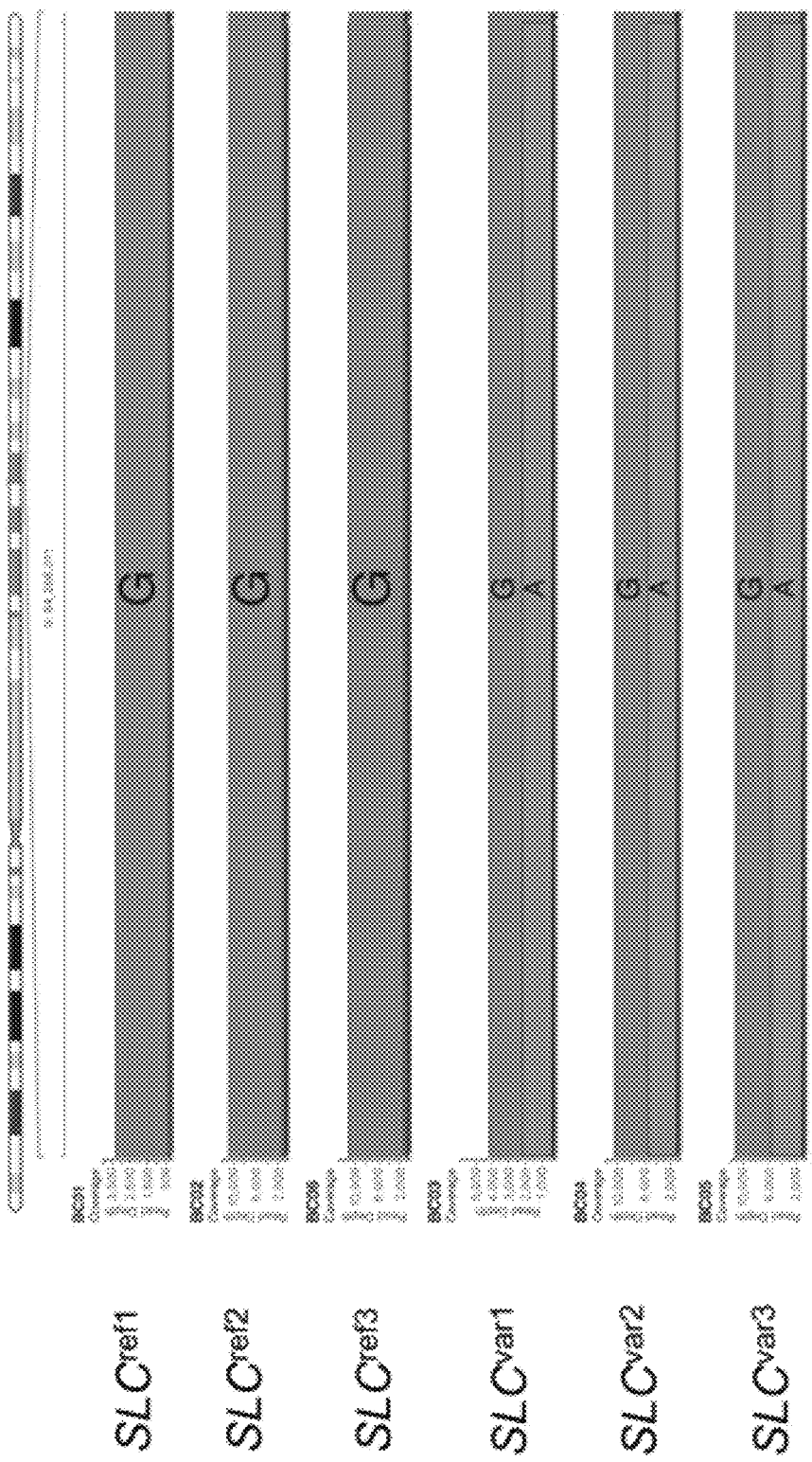
FIGS. 1A, 1B, 1C, 1D, 1E, and 1F. Patient-specific hiPSC-CMs recapitulate the cardioprotective effect of SLC28A3 variant rs7853758. Comparison of hiPSC-CMs derived from three patients harboring the heterozygous rs7853758 variant and were protected from DIC after DOX treatment (SLC$^{var1}$, SLC$^{var2}$, SLC$^{var3}$; collectively SLC$^{var}$), to hiPSC-CMs from three control patients who did not carry this protective SNP and developed DIC upon same DOX treatment (SLC$^{ref1}$, SLC$^{ref2}$, SLC$^{ref3}$, SLC$^{ref3}$SLC$^{ref3}$; collectively SLC$^{ref}$). A, Nanopore sequencing reads at SNP rs7853758 locus confirming its genotypes in all patient-derived hiPSC lines. B, Immunofluorescent staining showing the expression and localization of SLC28A3 throughout the cell in patient-derived hiPSC-CMs. C, Effect of DOX (72 h) on cell viability in SLC$^{var}$ (n=126) and SLC$^{ref}$ (n=81) hiPSC-CMs measured by a CellTiter-Glo 2.0 assay. D, Effect of DOX (72 h) on apoptosis measured by activated caspase 3/7 in SLC$^{var}$ (n=20) and SLC$^{ref}$ (n=20) hiPSC-CMs. E, Assessment of DOX uptake via measurement of percentage of cells with DOX intrinsic fluorescence using a flow cytometry-based assay in patient-derived hiPSC-CMs (n=8-13). F, SLC28A3 expression in SLC$^{ref}$ (n=3), and SLC$^{var}$ (n=3) hiPSC-CMs using western blot. n=full independent experimental replicates, Error bars, s.e.m, *P≤0.05, P≤0.01, *P≤0.001, ****P≤0.0001 by unpaired two-tailed Student's t-test (E and F). For (C and D) log-logistic non-linear regression model was used to estimate the value of the four parameters, and t-statistic was used to test for significant difference in LD$_{50}$ between different groups.
Figure 1B:
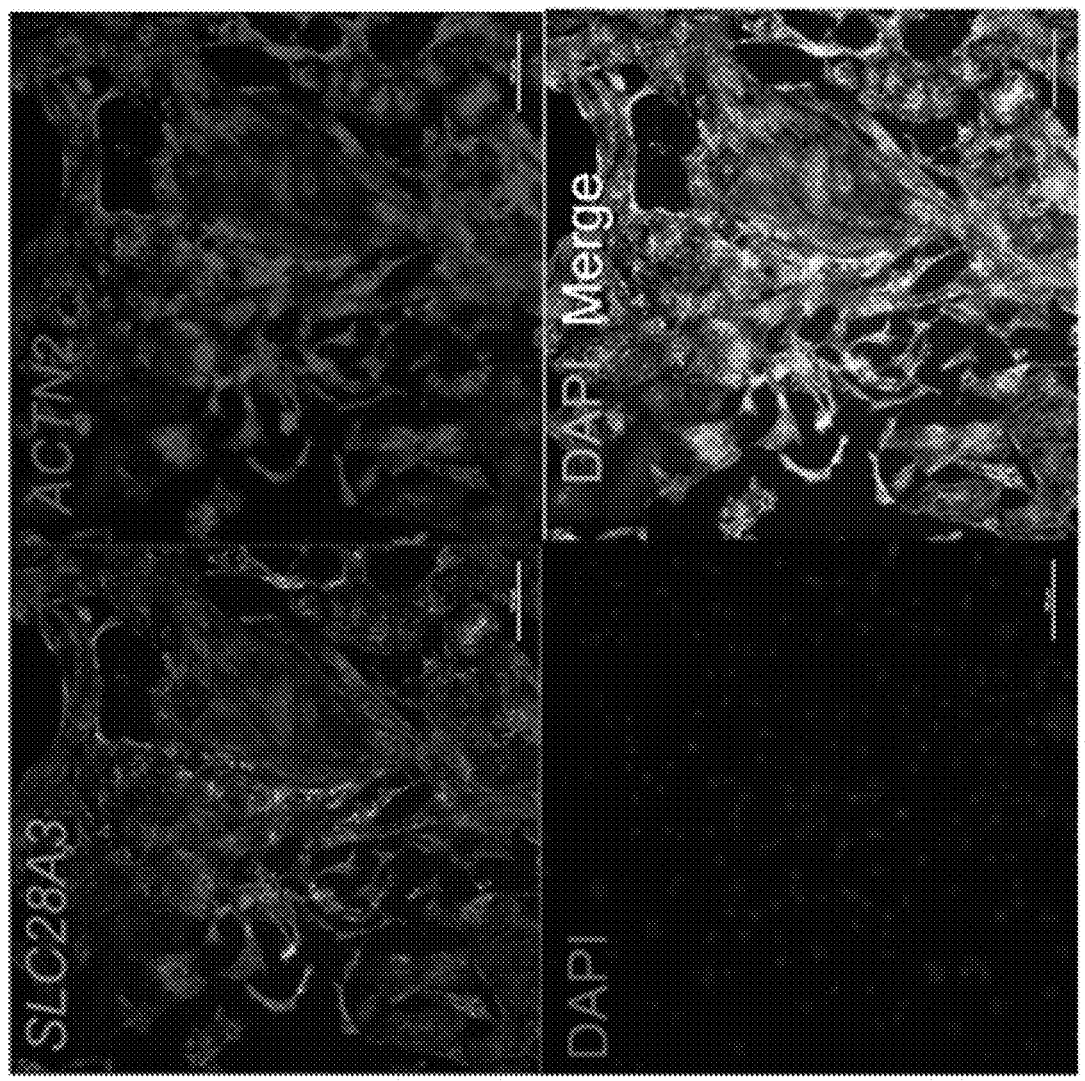
Figure 1D:
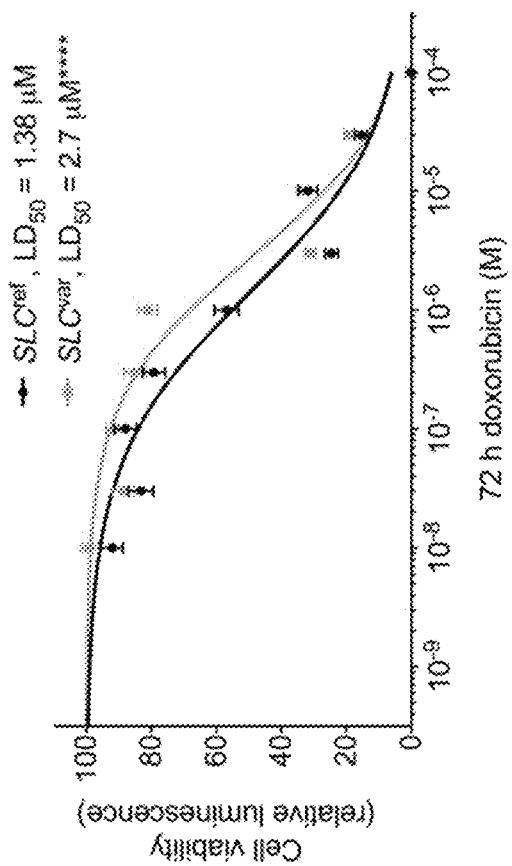
Figure 1C:
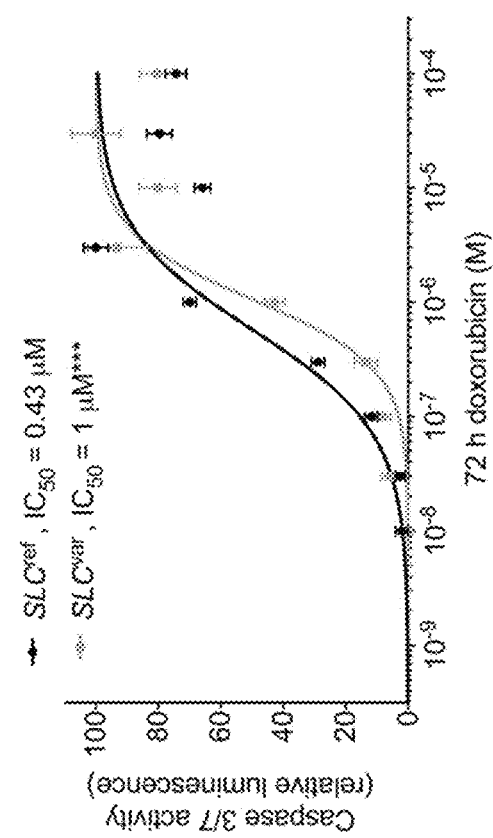
Figure 1F:
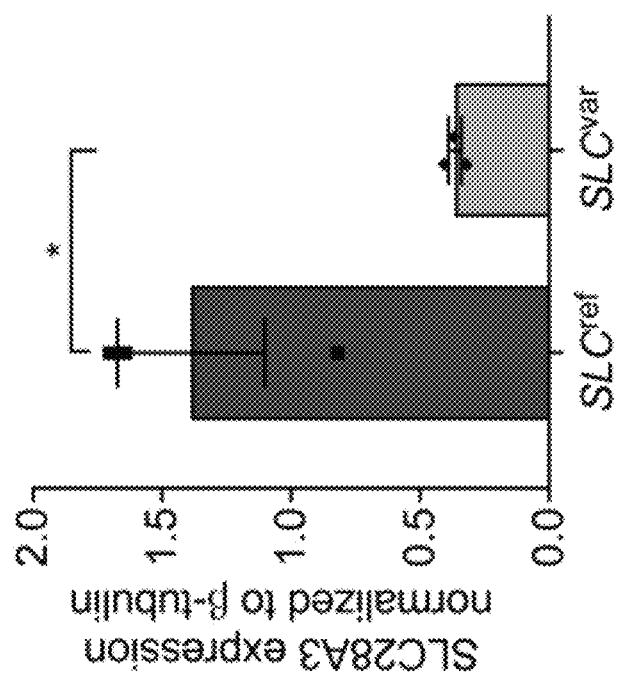
Figure 1E:
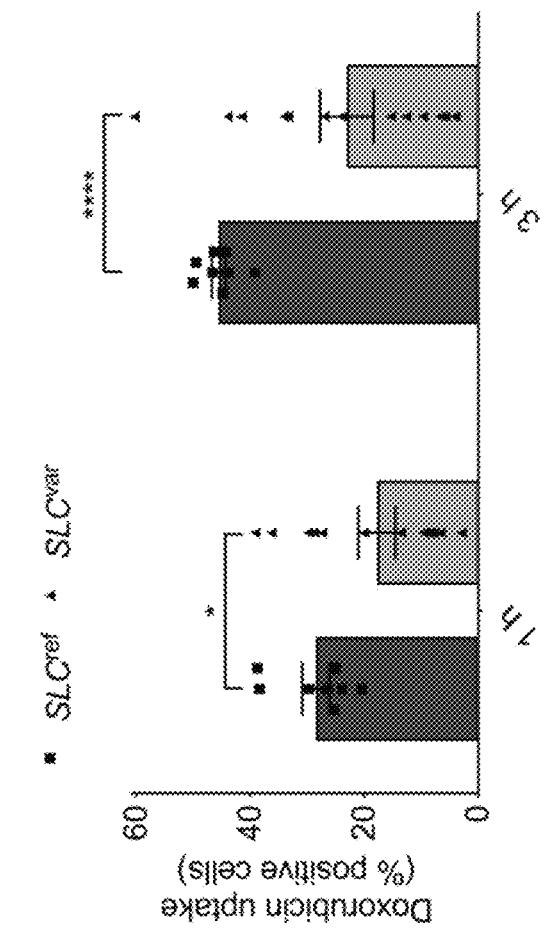

Inhibitors of SLC28A3 Activity or Expression to Attenuate Anthracycline-Induced Cardiotoxicity The inventors demonstrated that induced pluripotent stem cell (iPSC)-derived cardiomyocytes that comprised the SLC$^{var}$ polymorphism in the SLC28A3 gene have decreased caspase staining and increased cell viability as compared to iPSCs comprising only the dominant polymorphism SLC$^{ref}$ when contacted with the anthracycline doxorubicin (FIGS. 1C and 1D). In addition, the inventors demonstrated that cells with the SLC$^{var}$ polymorphism have reduced uptake of doxorubicin (FIG. 1E), which correlates with decreased SLC28A3 expression (FIG. 1F).

Accordingly, disclosed are methods, pharmaceutical compositions, kits, and systems for treating or preventing cardiotoxicity in a subject undergoing treatment with an anthracycline chemotherapeutic agent. The methods, pharmaceutical compositions, kits, and systems typically include or utilize therapeutic agent that inhibits the activity or expression of the solute carrier SLC28A3.

Human SLC28A3 has the amino acid sequence (SEQ ID NO: 1):

```
MELRSTAAPR AEGYSNVGFQ NEENFLENEN TSGNNSIRSR AVQSREHTNT KQDEEQVTVE   60
QDSPRNREHM EDDDEEMQQK GCLERRYDTV CGFCRKHKTT LRHIIWGILL AGYLVMVISA  120
CVLNFHRALP LFVITVAAIF FVVWDHLMAK YEHRIDEMLS PGRRLLNSHW FWLKWVIWSS  180
LVLAVIFWLA FDTAKLGQQQ LVSFGGLIMY IVLLFLFSKY PTRVYWRPVL WGIGLQFLLG  240
LLILRTDPGF IAFDWLGRQV QTFLEYTDAG ASFVFGEKYK DHFFAFKVLP IVVFFSTVMS  300
MLYYLGLMQW IIRKVGWIML VTTGSSPIES VVASGNIFVG QTESPLLVRP YLPYITKSEL  360
HAIMTAGFST IAGSVLGAYI SFGVPSSHLL TASVMSAPAS LAAAKLFWPE TEKPKITLKN  420
AMKMESGDSG NLLEAATQGA SSSISLVANI AVNLIAFLAL LSFMNSALSW FGNMFDYPQL  480
SFELICSYIF MPFSFMMGVE WQDSFMVARL IGYKTFFNEF VAYEHLSKWI HLRKEGGPKF  540
VNGVQQYISI RSEIIATYAL CGFANIGSLG IVIGGLTSMA PSRKRDIASG AVRALIAGTV  600
ACFMTACIAG ILSSTPVDIN CHHVLENAFN STFPGNTTKV IACCQSLLSS TVAKGPGEVI  660
PGGNHSLYSL KGCCTLLNPS TFNCNGISNT F                                691
```

The mRNA sequence for SLC28A3 Isoform X1 is provided at the National Center for Biotechnology (NCBI), Reference Sequence NM_001199633.2.

As discussed above, anthracycline chemotherapeutic agents are commonly used in the treatment of a variety of cell proliferative diseases or disorders. Thus, in the disclosed methods, the subject may have a cell proliferative disease or disorder such as cancer and may be undergoing or may have been selected to undergo treatment with an anthracycline chemotherapeutic agent. In some embodiments of the disclosed methods, the subject has a cell proliferative disease or disorder selected from the group consisting of bladder cancer, breast cancer, glioblastoma, lymphoma, leukemia, lung cancer, ovarian cancer, pancreatic cancer, soft tissue sarcoma, and thyroid cancer.

In the disclosed methods, the subject is undergoing or has been selected to undergo treatment with an anthracycline chemotherapeutic agent. The anthracycline chemotherapeutic agent may be an anthracycline that intercalates within DNA and prevents the release of topoisomerase 2 β (TOP2B) from DNA bound to the TOP2B. In the disclosed methods, the subject may be undergoing treatment with an anthracycline or may have been selected to undergo treatment with an anthracycline, where the anthracycline is selected from the group consisting of doxorubicin, daunorubicin, epirubicin, idarubicin, and aldoxorubicin.

The Examples demonstrate that SLC$^{ref}$ polymorphism protects against anthracycline-induced cardiotoxicity by reducing the uptake of anthracyclines into cardiac cells, e.g., cardiomyocytes. Thus, in one example embodiment, a subject that is undergoing or has been selected to undergo treatment with an anthracycline chemotherapeutic agent is administered an SLC28A3 inhibitor. In other embodiments, the subject that is undergoing or has been selected to undergo treatment with an anthracycline chemotherapeutic agent is administered a therapeutic agent that inhibits expression of SLC28A3, such as an RNAi therapeutic agent.

In some embodiments, the therapeutic agent inhibits activity or expression of SLC28A3 and treats or prevents undesirable side-effects that may be induced by the anthracycline chemotherapeutic agent, for example side-effects that may be induced by the anthracycline chemotherapeutic agent when the anthracycline chemotherapeutic agent is administered at an elevated dosage. In some embodiments, the maximum cumulative dose of the anthracycline chemotherapeutic agent that may be administered is increased when the therapeutic agent that inhibits activity or expression of SLC28A3 is administered.

In the disclosed methods, the subject may be undergoing or may be selected to undergo treatment with doxorubicin. In clinical practice, because of side-effects such as cardiotoxicity, the maximum cumulative dose of doxorubicin that is administered is ~400-450 mg/m². In some embodiments of the presently disclosed methods, a subject may be administered a maximum cumulative dose of doxorubicin that is greater than about 400 mg/m², 450 mg/m², 500 mg/m², 550 mg/m², or 600 mg/m², when the subject is administered the therapeutic agent that inhibits activity or expression of SLC28A3, either before, concurrently with, and/or after doxorubicin is administered to the subject.

In the disclosed methods, the subject may be undergoing or may be selected to undergo treatment with daunorubicin. In clinical practice, because of side-effects such as cardiotoxicity, the maximum cumulative dose of daunorubicin that is administered is ~600 mg/m². In some embodiments of the presently disclosed methods, a subject may be administered a maximum cumulative dose of daunorubicin that is greater than about 500 mg/m², 550 mg/m², 600 mg/m², 650 mg/m², or 700 mg/m², when the subject is administered the therapeutic agent that inhibits activity or expression of SLC28A3, either before, concurrently with, and/or after daunorubicin is administered to the subject.

In the disclosed methods, the subject may be undergoing or may be selected to undergo treatment with epirubicin. In clinical practice, because of side-effects such as cardiotoxicity, the maximum cumulative dose of epirubicin that is administered is ~900 mg/m². In some embodiments of the presently disclosed methods, a subject may be administered a maximum cumulative dose of epirubicin that is greater than about 800 mg/m², 850 mg/m², 900 mg/m², 950 mg/m², or 1000 mg/m², when the subject is administered the therapeutic agent that inhibits activity or expression of SLC28A3, either before, concurrently with, and/or after epirubicin is administered to the subject.

In the disclosed methods, the subject may be undergoing or may be selected to undergo treatment with idarubicin intravenously. In clinical practice, because of side-effects such as cardiotoxicity, the maximum cumulative dose of idarubicin that is administered intravenously is ~150 mg/m². In some embodiments of the presently disclosed methods, a subject may be administered a maximum cumulative dose of idarubicin intravenously that is greater than about 100 mg/m², 125 mg/m², 150 mg/m², 175 mg/m², or 200 mg/m², when the subject is administered the therapeutic agent that inhibits activity or expression of SLC28A3, either before, concurrently with, and/or after idarubicin is administered to the subject.

In the disclosed methods, the subject may be undergoing or may be selected to undergo treatment with idarubicin orally. In clinical practice, because of side-effects such as cardiotoxicity, the maximum cumulative dose of idarubicin that is administered orally is ~400 mg/m². In some embodiments of the presently disclosed methods, a subject may be administered a maximum cumulative dose of idarubicin orally that is greater than about 300 mg/m², 350 mg/m², 400 mg/m², 450 mg/m², or 500 mg/m², when the subject is administered the therapeutic agent that inhibits activity or expression of SLC28A3, either before, concurrently with, and/or after idarubicin is administered to the subject.

In the disclosed methods, the subject may be undergoing or may be selected to undergo treatment with an anthracycline chemotherapeutic agent and the subject is administered the therapeutic agent that inhibits activity or expression of SLC28A3, either before, concurrently with, or after the subject is administered the anthracycline chemotherapeutic agent. In some embodiments, the therapeutic agent inhibits activity of SLC28A3 inhibitor and prevents import of the anthracycline chemotherapeutic agent into cardiac cells for example by competitively inhibiting the anthracycline chemotherapeutic agent from being a substrate for import by the solute carrier SLC28A3.

In the disclosed methods, the subject may be undergoing or may be selected to undergo treatment with an anthracycline chemotherapeutic agent and the subject is administered the therapeutic agent that inhibits activity or expression of SLC28A3.

The inventors discovered that buconazole, tetracaine, propofol, and desipramine inhibit the uptake of anthracyclines by SCL28A3 and increase the viability of cells in the presence of doxorubicin (FIGS. 5B and 5C). Accordingly, in some embodiments, a subject is administered an SLC28A3 inhibitor selected from the group consisting of buconazole, tetracaine, propofol, and desipramine.

In some embodiments of the disclosed methods, the subject is administered a SLC28A3 inhibitor which is desipramine. Desipramine has the IUPAC name 3-(5,6-dihydrobenzo[b][1]benzazepin-11-yl)-N-methylpropan-1-amine and has the formula:

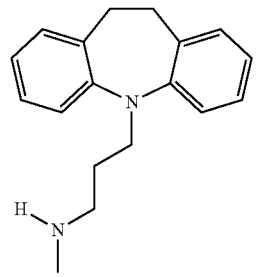 [SMILES: CNCCCN1c2ccccc2CCc2ccccc21]

In some embodiments of the disclosed methods, the subject is administered an SLC28A3 inhibitor which is butoconazole. Butoconazole has the IUPAC name 1-[4-(4-chlorophenyl)-2-(2,6-dichlorophenyl)sulfanylbutyl]imidazole and has the formula:

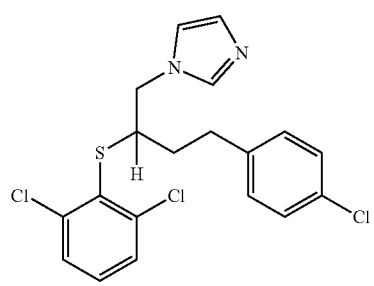 [SMILES: Clc1ccc(CCC(Cn2ccnc2)Sc2c(Cl)cccc2Cl)cc1]

In some embodiments of the disclosed methods, the subject is administered a SLC28A3 inhibitor which is tetracaine. Tetracaine has the IUPAC name 2-(dimethylamino) ethyl 4-(butylamino)benzoate and has the formula:

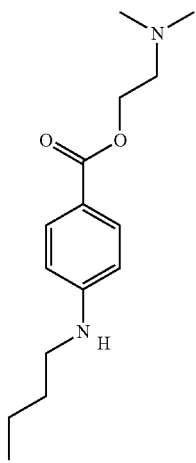

In some embodiments of the disclosed methods, the subject is administered an SLC28A3 inhibitor which is propofol. Propofol has the IUPAC name 2,6-di(propan-2-yl)phenol and has the formula:

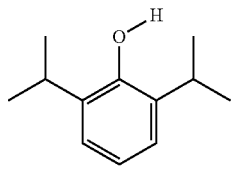

In some embodiments of the disclosed methods, the subject is administered an SLC28A3 inhibitor selected from the group consisting of, but not limited to, 3-(5,6-dihydrobenzo[b][1]benzazepin-11-yl)-N-methylpropan-1-amine, 1-[4-(4-chlorophenyl)-2-(2,6-dichlorophenyl)sulfanylbutyl] imidazole, 2-(dimethylamino)ethyl 4-(butylamino)benzoate, and 2,6-di(propan-2-yl)phenol.

In some embodiments of the disclosed methods, the subject is administered a therapeutic agent that inhibits expression of SLC28A3. Suitable therapeutic agents that inhibit expression of SLC28A3 may include, but are not limited to, therapeutic agents for performing RNA interference of SLC28A3 mRNA.

In the disclosed methods, the subject may be undergoing or may be selected to undergo treatment with an anthracycline chemotherapeutic agent and the subject is administered a therapeutic agent that inhibits the activity or expression of SLSC28A3. The therapeutic agent that inhibits the activity or expression of SLSC28A3 may be administered prior to, concurrently with, and/or after administering the anthracycline chemotherapeutic agent.

Children are especially sensitive to the undesirable side-effects of chemotherapy with anthracycline agents. In some embodiments of the disclosed methods, the subject is no more than about 18, no more than about 17, no more than about 16, no more than about 15, no more than about 14, no more than about 13, no more than about 12, no more than about 11, no more than about 10, no more than about 9, no more than about 8, no more than 7, no more than about 6, no more than about 5, no more than about 4, no more than about 3, no more than about 2, or no more than about 1 year(s) of age. In some embodiments, the subject is less than about 18, less than about 17, less than about 16, less than about 15, less than about 14, less than about 13, less than about 12, less than about 11, less than about 10, less than about 9, less than about 8, less than about 7, less than about 6, less than about 5, less than about 4, less than about 3, less than about 2, or less than about 1 year(s) old.

Also disclosed herein are pharmaceutical compositions, kits, and therapeutic systems that comprise and/or utilize a therapeutic agent that inhibits the activity or expression of SLC28A3. In some embodiments of the disclosed pharmaceutical compositions, kits, and therapeutic systems, the therapeutic agent that inhibits the activity or expression of SLC28A3 is an SLC28A3 inhibitor. Without being limited by any theory or mechanism it is believed that some SLC28A3 inhibitors prevent the import of anthracyclines into cardiac cells. Suitable SLC28A3 inhibitors for the disclosed methods, pharmaceutical compositions, kits, and therapeutic systems may include SLC28A3 inhibitors that prevent the solute transporter SLC28A3 form importing anthracyclines into cardiac cells, e.g., butoconazole, tetracaine, propofol, and desipramine. In some embodiments of the disclosed pharmaceutical compositions, kits, and therapeutic systems, the SLC28A3 inhibitor is a selective inhibitor for SLC28A3. As used herein, "selective inhibitor for SLC28A3" refers to an inhibitor which reduces anthracycline import into cardiac cells by inhibiting SLC28A3, but does not significantly affect the function of related transport proteins.

Suitable anthracycline chemotherapeutic agents for the disclosed methods, pharmaceutical compositions, kits, and therapeutic systems may include anthracyclines that intercalate within DNA and prevents the release of topoisomerase 2 β (TOP2B) from DNA bound to the TOP2B. In some embodiments of the disclosed pharmaceutical compositions, kits, and therapeutic systems the anthracycline is selected from the group consisting of doxorubicin, daunorubicin, epirubicin, idarubicin, and aldoxorubicin.

The disclosed methods, kits, and devices may utilize or include a reagent that is utilized for detecting an SLC28A3 polymorphism. Suitable reagents may include nucleic acid reagents. For example, nucleic acid reagents may include reagents comprising a DNA oligonucleotide that hybridizes specifically to the SLC28A3 gene or that hybridizes specifically to a polymorphism in the SLC28A3 gene. In some embodiments, the methods, kits, and device may utilize or include nucleic acid reagents that comprise one or more primers for sequencing at least a portion of the SLC28A3 gene (e.g., where the portion of the SLC28A3 gene comprises an SLC28A3 polymorphism selected from the group consisting of a polymorphism resulting in a synonymous G>A Leu461Leu change (the polymorphism also known as rs7853758). In further embodiments, the methods, kits, and device may utilize or include nucleic acid reagents that comprise one or more primer pairs for amplifying at least a portion of the SLC28A3 gene (e.g., where the portion of the SLC28A3 gene comprises an SLC28A3 polymorphism selected from the group consisting of a polymorphism resulting in a G>A synonymous Leu461Leu change.

As used herein the terms "diagnose" or "diagnosis" or "diagnosing" refer to distinguishing or identifying a disease, syndrome or condition or distinguishing or identifying a person having or at risk for developing a particular disease, syndrome or condition. As used herein the terms "prognose"

or "prognosis" or "prognosing" refer to predicting an outcome of a disease, syndrome or condition. The methods contemplated herein include predicting resistance to anthracycline-induced cardiotoxicity in a patient that is associated with an SLC28A3 polymorphism (the SNP referred to as rs7853758). The methods contemplated herein also include determining a prognosis for a patient having a psychiatric disorder that is associated with a SLC28A3 polymorphism.

The present methods may include detecting an SLC28A3 polymorphism in a patient sample (e.g., a sample comprising nucleic acid). The term "sample" or "patient sample" is meant to include biological samples such as tissues and bodily fluids. "Bodily fluids" may include, but are not limited to, blood, serum, plasma, saliva, cerebral spinal fluid, pleural fluid, tears, lactal duct fluid, lymph, sputum, and semen. A sample may include nucleic acid, protein, or both.

The detected SLC28A3 polymorphism is present in nucleic acid. The term "nucleic acid" or "nucleic acid sequence" refers to an oligonucleotide, nucleotide or polynucleotide, and fragments or portions thereof, which may be single or double stranded, and represents the sense or antisense strand. A nucleic acid may include DNA or RNA and may be of natural or synthetic origin. For example, a nucleic acid may include mRNA or cDNA. Nucleic acid may include nucleic acid that has been amplified (e.g., using polymerase chain reaction). Nucleic acid may include genomic nucleic acid.

As used herein, the term "assay" or "assaying" means qualitative or quantitative analysis or testing.

As used herein the term "sequencing," as in determining the sequence of a polynucleotide, refers to methods that determine the base identity at multiple base positions or that determine the base identity at a single position.

The term "amplification" or "amplifying" refers to the production of additional copies of a nucleic acid sequence. Amplification is generally carried out using polymerase chain reaction (PCR) technologies known in the art.

The term "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The present methods and kits may utilize or contain primers, probes, or both. The term "primer" refers to an oligonucleotide that hybridizes to a target nucleic acid and is capable of acting as a point of initiation of synthesis when placed under conditions in which primer extension is initiated (e.g., primer extension associated with an application such as PCR). For example, primers contemplated herein may hybridize to one or more polynucleotide sequences comprising the SLC28A3 polymorphisms disclosed herein. A "probe" refers to an oligonucleotide that interacts with a target nucleic acid via hybridization. A primer or probe may be fully complementary to a target nucleic acid sequence or partially complementary. The level of complementarity will depend on many factors based, in general, on the function of the primer or probe. For example, probes contemplated herein may hybridize to one or more polynucleotide sequences comprising the SLC28A3 polymorphisms disclosed herein. A primer or probe may specifically hybridize to a target nucleic acid (e.g., hybridize under stringent conditions as discussed herein). In particular, primers and probes contemplated herein may hybridize specifically to one or more polynucleotide sequences that comprise the SLC28A3 polymorphisms disclosed herein and may be utilized to distinguish a polynucleotide sequence comprising a minor allele from a polynucleotide sequence comprising the major allele.

An "oligonucleotide array" refers to a substrate comprising a plurality of oligonucleotide primers or probes. The arrays contemplated herein may be used to detect the SLC28A3 polymorphisms disclosed herein.

As used herein, the term "specific hybridization" indicates that two nucleic acid sequences share a high degree of complementarity. Specific hybridization complexes form under stringent annealing conditions and remain hybridized after any subsequent washing steps. Stringent conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, a "target nucleic acid" refers to a nucleic acid molecule containing a sequence that has at least partial complementarity with a probe oligonucleotide, a primer oligonucleotide, or both. A primer or probe may specifically hybridize to a target nucleic acid.

The present methods may be performed to detect the presence or absence of the disclosed SLC28A3 polymorphisms. Methods of determining the presence or absence of a SLC28A3 polymorphism may include a variety of steps known in the art, including one or more of the following steps: reverse transcribing mRNA that comprises the SLC28A3 polymorphism to cDNA, amplifying nucleic acid that comprises the SLC28A3 polymorphism (e.g., amplifying genomic DNA that comprises the SLC28A3 polymorphism), hybridizing a probe or a primer to nucleic acid that comprises the SLC28A3 polymorphisms (e.g., hybridizing a probe to mRNA, cDNA, or amplified genomic DNA that comprises the SLC28A3 polymorphism), and sequencing nucleic acid that comprises the SLC28A3 polymorphism (e.g., sequencing cDNA, genomic DNA, or amplified DNA that comprises the SLC28A3 polymorphism).

A "polymorphism" refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism (SNP) is the replacement of one nucleotide by another nucleotide at the polymorphic site. Deletion of a single nucleotide or insertion of a single nucleotide also gives rise to single nucleotide polymorphisms. "Single nucleotide polymorphism" preferably refers to a single nucleotide substitution. Typically, between different individuals, the polymorphic site can be occupied by two different nucleotides which results in two different alleles with the most common allele in the population (i.e., the ancestral allele) being referred to as the "major allele" and the less common allele in the population being referred to as the "minor allele." An individual may be homozygous or heterozygous for the major allele or the minor allele of the polymorphism. "Mutation" as utilized herein, is intended to encompass a single nucleotide substitution, which may be recognized as a single nucleotide polymorphism. Exemplary SNPs disclosed herein including rs7853758 which is a G>A change that results in a synonymous Leu461Leu change.

In the methods and kits, the minor allele and/or the major allele associated with a polymorphism may be detected. The methods may include, and the kits and devices may be used for, determining whether a patient is homozygous or heterozygous for a minor allele and/or major allele associated with a polymorphism (e.g., a SNP). The term "heterozygous" refers to having different alleles at one or more genetic loci in homologous chromosome segments. As used herein "heterozygous" may also refer to a sample, a cell, a cell population or a patient in which different alleles (e.g., major or minor alleles of SNPs) at one or more genetic loci may be detected.

As used herein, the term "homozygous" refers to having identical alleles (e.g., major or minor alleles of SNPs) at one or more genetic loci in homologous chromosome segments. "Homozygous" may also refer to a sample, a cell, a cell population, or a patient in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

Suitable polymorphism for the presently disclosed methods, kits, and arrays may include a G>A polymorphism (or mutation) resulting in a synonymous Leu461Leu amino acid substitution known as rs7853758 which may be a Guanine (G) in the major allele or an Adenine (A) in the minor allele.

The present methods contemplate detecting a single nucleotide polymorphism (SNP). For example, the present methods may detect rs7853758 in either one or both alleles of the patient. (See, rs7853758 SNP entry at the National Center for Biotechnology Information, which entry is incorporated herein by reference and refers to a G←→A transition at the reference nucleotide position, where the G-allele is the major allele and the A-allele is the minor allele). The present methods may detect a G-allele or an A-allele corresponding to the polymorphism (i.e., a G-nucleotide or an A-nucleotide at the position associated with the rs7853758). The present methods may detect whether a patient is homozygous or heterozygous for a G-allele or A-allele (i.e., whether the patient is GG, GA, or AA at the reference nucleotide position for rs7853758).

The inventors discovered novel compositions which reduce anthracycline induced cardiotoxicity, which may be especially useful in subjects who do not have a genetic predisposition for reduced anthracycline induced cardiotoxicity, e.g., subjects who have one or two copies of the $SLC^{ref}$ polymorphism. In an aspect of the disclosure, methods for treating a subject having a cell proliferative disorder, wherein the subject has a polymorphic allele $SLC^{ref}$ are provided. In some embodiments, the methods comprise: (a) administering to the subject a cumulative dose of an anthracycline as follows: doxorubicin, wherein the cumulative dose is greater than about 400 $mg/m^2$; daunorubicin, wherein the cumulative dose is greater than about 600 $mg/m^2$; epirubicin, wherein the cumulative dose is greater than about 900 $mg/m^2$; idarubicin administered intravenously, wherein the cumulative dose is greater than about 150 $mg/m^2$; or idarubicin administered orally, wherein the cumulative dose is greater than about 150 $mg/m^2$; and (b) administering a therapeutic agent that inhibits the activity or expression of the SLC28A3 transporter.

As used herein, "$SLC^{ref}$" refers to the allele at the position notated rs7853758 SNP entry at the National Center for Biotechnology Information for the major allele, i.e., the G allele. As used herein, "$SLC^{var}$" refers to the allele at the position notated rs7853758 SNP entry at the National Center for Biotechnology Information for the minor allele, i.e., the A allele.

As used herein, "having a polymorphic allele $SLC^{ref}$" refers to the composition of the subjects somatic genome comprising the $SLC^{ref}$ polymorphism. In other words, the DNA sequence of the subject's somatic cells comprises the $SLC^{ref}$ polymorphism.

The present methods may detect the polymorphism directly by analyzing chromosomal nucleic acid having the polymorphic variant sequence. Alternatively, the present method may detect the polymorphism indirectly by detecting an isoform nucleic acid expressed from the polymorphic variant sequence, by detecting an isoform polypeptide expressed from the polymorphic variant sequence, or by analyzing the expression of another nucleic acid or protein whose expression is regulated by the polymorphic sequence.

Illustrative Embodiments

1. A method of treating a subject having a cell proliferative disease or disorder, the method comprising administering to the subject: (i) an effective amount of an anthracycline for treating the cell proliferative disease or disorder; and (ii) an effective amount of a therapeutic agent that inhibits the activity or expression of the SLC28A3 transporter for inhibiting cardiotoxicity induced by the anthracycline.
2. The method of embodiment 1, wherein the cell proliferative disease or disorder is cancer.
3. The method of any of embodiments 1-2, wherein the cell proliferative disease or disorder is leukemia.
4. The method of any of embodiments 1-3, wherein the subject is of an age less than about 18 years old.
5. The method of any of embodiments 1-4, wherein the anthracycline is selected from doxorubicin, daunorubicin, epirubicin, or idarubicin.
6. The method of embodiment 5, wherein the anthracycline is doxorubicin.
7. The method of any of embodiments 1-6, wherein an effective amount of the anthracycline comprises a dose of anthracycline that exceeds a recommended cumulative dose.

8. The method of any of embodiments 1-7, wherein the therapeutic agent that inhibits the activity or expression of the SLC28A3 transporter is an SLC28A3 inhibitor selected from the group consisting of butoconazole, tetracaine, propofol, and desipramine.

9. The method of any of embodiment 8, wherein the inhibitor is desipramine.

10. The method of any of embodiments 1-9, wherein the subject has the polymorphic allele $SLC^{ref}$.

11. The method of any of embodiments 1-7, wherein the therapeutic agent inhibits the expression of the SLC28A3 transporter.

12. The method of embodiment 11, wherein the therapeutic agent that inhibits the expression of the SLC28A3 transporter comprises interfering RNA that inhibits the expression of the SLC28A3 transporter.

13. A method comprising:
   (a) detecting a polymorphic allele of SLC28A3 in a subject having a cell proliferative disease or disorder;
   (b) administering to the subject an anthracycline and a therapeutic agent that inhibits the activity or expression of the SLC28A3 transporter.

14. The method of embodiment 13, wherein the cell proliferative disease or disorder is cancer.

15. The method of either of embodiments 13 or 14, wherein the cell proliferative disease or disorder is leukemia.

16. The method of any of embodiments 13-15, wherein the subject is of an age less than about 18 years old.

17. The method of any of embodiments 13-16, wherein the anthracycline is selected from doxorubicin, daunorubicin, epirubicin, or idarubicin.

18. The method of embodiment 17, wherein the anthracycline is doxorubicin.

19. The method of any of embodiments 13-18, wherein the subject has at least one copy of the $SLC^{ref}$ allele.

20. The method of any of embodiments 13-19, wherein the therapeutic agent that inhibits the activity or expression of the SLC28A3 transporter inhibitor is an SLC28A3 inhibitor selected from the group consisting of butoconazole, tetracaine, propofol, and desipramine.

21. The method of embodiment 20, wherein the inhibitor is desipramine.

22. The method of any of embodiments 13-19, wherein the therapeutic agent inhibits the expression of the SLC28A3 transporter.

23. The method of embodiment 22, wherein the therapeutic agent that inhibits the expression of the SLC28A3 transporter comprises interfering RNA that inhibits the expression of the SLC28A3 transporter.

24. A method for treating a subject having a cell proliferative disorder, wherein the subject has a polymorphic allele $SLC^v$, the method comprising:
   (a) administering to the subject a cumulative dose of an anthracycline as follows: doxorubicin, wherein the cumulative dose is greater than about 400 mg/m$^2$; daunorubicin, wherein the cumulative dose is greater than about 600 mg/m$^2$; epirubicin, wherein the cumulative dose is greater than about 900 mg/m$^2$; idarubicin administered intravenously, wherein the cumulative dose is greater than about 150 mg/m$^2$; or idarubicin administered orally, wherein the cumulative dose is greater than about 150 mg/m$^2$; and
   (b) administering a therapeutic agent that inhibits the activity or expression of the SLC28A3 transporter.

25. The method of embodiment 24, wherein the subject has at least one copy of the $SLC^{ref}$ allele.

26. The method of embodiment 24 or 25, wherein the cell proliferative disease or disorder is cancer.

27. The method of embodiment 26, wherein the cell proliferative disease or disorder is leukemia.

28. The method of any of embodiments 24-27, wherein the subject is of an age less than about 18 years old.

29. The method of any of embodiments 24-28, wherein the therapeutic agent that inhibits the activity or expression of the SLC28A3 transporter is an SLC28A3 inhibitor selected from the group consisting of butoconazole, tetracaine, propofol, and desipramine.

30. The method of embodiment 29, wherein the inhibitor is desipramine.

31. The method of any of embodiments 24-28, wherein the therapeutic agent inhibits the expression of the SLC28A3 transporter.

32. The method of embodiment 31, wherein the therapeutic agent that inhibits the expression of the SLC28A3 transporter comprises interfering RNA that inhibits the expression of the SLC28A3 transporter.

33. A kit or treatment system comprising as components:
   (i) an anthracycline chemotherapeutic agent; and (ii) a therapeutic agent that inhibits the activity or expression of the SLC28A3 transporter.

34. The kit or treatment system of embodiment 33, wherein the anthracycline is selected from doxorubicin, daunorubicin, epirubicin, or idarubicin.

35. The kit or treatment system of embodiment 34, wherein the anthracycline is doxorubicin.

36. The kit or treatment system of any of embodiments 33-35, wherein the therapeutic agent that inhibits the activity or express of the SLC28A3 transporter is an SLC28A3 inhibitor selected from the group consisting of butoconazole, tetracaine, propofol, and desipramine.

37. The kit or treatment system of embodiment 36, wherein the inhibitor is desipramine.

38. The method of any of embodiments 33-35, wherein the therapeutic agent inhibits the expression of the SLC28A3 transporter.

39. The method of embodiment 38, wherein the therapeutic agent that inhibits the expression of the SLC28A3 transporter comprises interfering RNA that inhibits the expression of the SLC28A3 transporter.

EXAMPLES

The following Examples are illustrative and is not intended to limit the scope of the claimed subject matter.

Example 1: Inhibition of SLC Transporter Activity or Expression to Attenuate Anthracycline-Induced Cardiotoxicity Background Multiple pharmacogenomic studies have identified the synonymous genomic variant rs7853758 (G>A, L461L) and the intronic variant rs885004 in SLC28A3 as statistically associated with a lower incidence of anthracycline-induced cardiotoxicity (AIC). However, the true causal variant(s), the cardioprotective mechanism of this locus, the role of SLC28A3 and other solute carrier (SLC) transporters in AIC, and the suitability of SLC transporters as targets for cardioprotective drugs has not been investigated.

Methods

Six well-phenotyped, doxorubicin-treated pediatric patients from the original association study cohort were re-recruited and human induced pluripotent stem cell-derived cardiomyocytes were generated. Patient-specific doxorubicin-induced cardiotoxicity (DIC) was then characterized using assays of cell viability, activated caspase 3/7, and doxorubicin uptake. The role of SLC28A3 in DIC was then queried using overexpression and knockout of SLC28A3 in isogenic hiPSCs using a CRISPR/Cas9. Fine-mapping of the SLC28A3 locus was then completed after SLC28A3 resequencing and an extended in silico haplotype and functional analysis. Genome editing of potential causal variant was done using cytosine base editor. SLC28A3-AS1 overexpression was done using a lentiviral plasmid-based transduction and was validated using stranded RNA-Seq after ribosomal RNA depletion. Drug screening was done using the Prestwick drug library (n=1200) followed by in vivo validation in mice. The effect of desipramine on DOX cytotoxicity was also investigated in eight cancer cell lines.

Results

Here, using the most commonly used anthracycline, doxorubicin, we demonstrate that patient-derived cardiomyocytes recapitulate the cardioprotective effect of the SLC28A3 locus and that SLC28A3 expression influences the severity of DIC. Using Nanopore-based fine-mapping and base editing we identify a novel cardioprotective SNP rs11140490 in the SLC28A3 locus which exerts its effect by regulating an antisense long noncoding-RNA (SLC28A3-AS1) that overlaps with SLC28A3. Using high-throughput drug screening in patient-derived cardiomyocytes and whole organism validation in mice, we identify the SLC competitive inhibitor desipramine as protective against DIC.

Conclusion

This work demonstrates the power of the human induced pluripotent stem cell model to take a SNP from a statistical association through to drug discovery, providing human cell-tested data for clinical trials to attenuate DIC.

Example 2: Identification of Drug Transporter Genomic Variants and Inhibitors that Protect Against Doxorubicin-Induced Cardiotoxicity Introduction Doxorubicin (DOX), a cytotoxic anthracycline antibiotic, is a common anti-cancer agent used to treat a wide variety of adult and childhood cancers. The cardiotoxicity of anthracyclines has been documented to be occur in 9% of treated adult patients[1], and on average occurs in just 3.5 months after the last chemotherapy dose and 98% of patients experience cardiotoxicity within the first year[1]. Early cardiotoxicity leads to dose limitation or treatment discontinuation to the detriment of therapy. The cardiotoxicity of doxorubicin is also well-understood to be dose-dependent, with 65% and 85% of cancer patients experiencing a decline in left ventricular ejection fraction (LVEF) when treated with DOX dose of 550 and 700 mg/m$^2$, respectively[2]. However, even despite attempts to severely limit cumulative dose, cardiotoxicity occurs in 14.5% of breast cancer patients receiving the most common 240 mg/m$^2$ cumulative dose[3].

Pharmacogenomic research has attempted to discover predictive DNA biomarkers for anthracycline-induced cardiotoxicity (AIC) and has so far identified about 75 AIC-associated loci[4,5]. However, the true connection between these loci and cardiotoxicity is far from proven, as the vast majority of AIC pharmacogenomic studies lack functional validation of the identified associations. As a result, there are currently no FDA-approved genetic biomarkers being used in routine clinical practice to predict AIC[6], and only a single on-market drug, dexrazoxane is approved to decrease the incidence of AIC.

SLC28A3 encodes solute carrier transporter family 28 member 3 and is the most robustly replicated AIC-associated cardioprotective loci. This locus was initially discovered in a large multi-center pediatric candidate gene association study (CGAS), identifying two single nucleotide polymorphisms (SNPs), rs7853758 (G>A, L461L), which is in a coding region but synonymous, and rs885004 which is located in intron 8. Both SNPs are in high linkage disequilibrium. rs7853758 is highly associated with a lower risk of developing DIC in both discovery (n=188, P$^{adj}$=0.0071, OR=0.29) and replication (n=156, P$^{adj}$=0.0072, OR=0.33) cohorts[7]. Importantly, this genetic association was replicated in a third additional multicenter independent cohort of 218 patients[8]. The sensitivity and specificity (95% CI) of rs7853758 is 17.4 (7.8-31.4) and 64.6 (58.8-70.1), respectively 9. Despite identification of this SNP through two replication cohorts in CGAS, the mechanisms by which a synonymous variant can influence AIC is unclear. Thus, the validity of this this locus in relation to AIC, the true causal variant and the cardioprotective mechanism of this locus, the role of SLC28A3 and other solute carrier (SLC) transporters in AIC, and the suitability of SLC transporters as targets for cardioprotective drugs are critical unanswered questions.

Here, we show that patient-specific hiPSC-CMs recapitulate the cardioprotective effect of SNP rs7853758. SLC28A3 knockdown and overexpression using CRISPR/Cas9 reduces and increases DOX uptake into cardiomyocytes respectively, altering their sensitivity to DOX, thus confirming the role of this locus in DIC. Fine-mapping of the SLC28A3 locus uncovered that rather than the original CGAS-identified synonymous SNP (rs7853758), it is actually the linked SNP rs11140490 that is the causal cardioprotective variant within that locus. Further mechanistic studies showed that rs11140490 exerts its action by regulating a SLC28A3-overlapping antisense long non-coding RNA SLC28A3-AS1. Screening for other potential cardiac-specific SLC transporters in relation to DIC revealed that SLC22A4 and SLC22A17 are also implicated in DIC. Finally screening a drug library using hiPSC-CMs followed by in vivo validation in a mouse model of DIC discovered that the SLC competitive inhibitor, desipramine protects against DIC by without hindering DOX chemotherapy efficacy. Together these findings provide a novel genetic test for rs11140490 that can identify patients who are protected from DIC and two potential therapeutic options, either using the lncRNA SLC28A3-AS1 or developing a derivative of desipramine to attenuate DIC.

Methods

The data, analytic methods, and study materials are available other researchers upon reasonable request for purposes of reproducing the results. RNA-seq data have been deposited in Gene Expression Omnibus with accession code GSE165731.

Human induced pluripotent cell derivation and cardiac differentiation. Protocols and consents were approved by the Northwestern University and University of British Columbia Institutional Review Boards. Six well-phenotyped, doxorubicin-treated pediatric patients from the original association study cohort were re-recruited with informed consent. Peripheral blood mononuclear cells were isolated from blood and reprogramed to hiPSCs using CytoTune-iPS 2.0 Sendai Reprogramming Kit (Invitrogen)[10]. SNP karyotyping was performed using a whole-genome Infinium HumanCytoSNP-12 BeadChip Array (Illumina). Differentiation into cardiomyocytes was performed according to previously described protocol with some modifications[11, 12] including the use of a TNNT2-driven antibiotic selection cassette for cardiomyocyte purification.

CRISPR/Cas9-mediated gene knockout and overexpression. To generate SLC28A3 knockout gRNA expression vectors, gRNA targeting the start codon designed with minimal predicted off-target effect[13]. Each gRNA was annealed and inserted into pSpCas9(BB)-2A-Puro (PX459) V2.0 (48138, Addgene) plasmid that expresses puromycin resistance gene for downstream antibiotic selection, in addition to Cas9. $10^6$ cells were electroporated with 5 μg PX459 plasmid and positive clones were selected 24 h post transfection using puromycin treatment for 48 h. To generate SLC28A3 overexpressing cells, Human SLC28A3 Sequence-Verified cDNA was first amplified and cloned under the CAG promoter of a pAAVS1-Nst-CAG-DEST gateway cloning vector (80489, Addgene). AAVS1 gRNA expression vector[14] (pXAT2, Addgene 80494), which expresses gRNA and Cas9, was used to target AAVS1 locus in the first intron of the PPPIR12C gene[14]. Cells were then electroporated with AAVS1 targeting plasmid and SLC28A3 overexpression donor plasmid. Positive clones were selected using neomycin treatment for 14 days.

Patient-specific doxorubicin-induced cardiotoxicity (DIC) characterization. Patient-specific DIC was characterized by assays of cell viability using CellTiter-Glo 2.0 (Promega) and activated caspase 3/7 using Caspase 3/7-Glo (Promega) that were used per manufacturer's instructions. Doxorubicin uptake was quantified using flow cytometry by measuring DOX intrinsic fluorescence-PE 1 and 3 h post doxorubicin treatment and normalized to baseline fluorescence. All cells were stained with NucRed Live Ready-Probes Reagent (Invitrogen) to monitor cell viability.

SLC28A3 locus genetic fine mapping. Fine-mapping of the SLC28A3 locus was then completed after SLC28A3 resequencing using MinION Nanopore sequencer and an extended in silico haplotype and functional analysis.

Genome editing of potential causal variant rs11140490. Locus-specific base-editor protein complex and the gRNA were designed using Beditor[15], and the designed gRNA was cloned in the gRNA expressing plasmid (73797, Addgene). Then $1 \times 10^6$ cells were electroporated with 4 μg of the base editor expressing plasmid (pSI-Target-AID-NG, 119861, Addgene) and 4 μg of the gRNA expressing plasmid (lenti sgRNA (MS2)_puro, 73797, Addgene). Cells were then selected with puromycin 24 h post transfection for 48 h, clones were hand-picked, the target locus was PCR-amplified and sanger-sequenced to confirm the SNP editing in all clones.

SLC28A3-AS1 overexpression in isogenic hiPSCs. The SLC28A3-AS1 cDNA was cloned into pLenti-C-Myc-DDK-IRES-Puro lentiviral vector (Origene) which was then co-transfected with packaging plasmids psPAX2 (Addgene 12260) and pMD2.G (Addgene 12259) into Lenti-X 293T cells (Takara) to generate lentivirus. Virus-containing supernatant was collected at 48- and 72-hours post-transfection. Lentivirus was concentrated 1:100 from cleared supernatant using PEG-iT (SBI). Isogeneic hiPSCs were then transduced and positive clones were selected with puromycin for seven days to generate ISO$^{SLC28A3-AS1}$. SLC28A3-AS1 overexpression was confirmed using stranded RNA-Seq after ribosomal RNA depletion.

Mouse model of doxorubicin-induced cardiomyopathy and drug administration. Procedures followed were in accordance with Stanford University's institutional guidelines. In vivo validation was done using C57BL/6J 10 week old male mice were co-treated with doxorubicin (NovaPlus) and water as a control vehicle (n=10), or with desipramine (Sigma) as experimental groups (n=8). At day 0, mice were treated with doxorubicin (3 mg kg$^{-1}$) intraperitoneally twice a week alone or with desipramine by Alzet pump infusion (20 mg kg$^{-1}$ day$^{-1}$) for 3 weeks (day 0-day 21). For the control group, we treated mice with corn oil in the same schedule as desipramine administration. We recorded an echocardiogram once a week (day 0, day 7, day 14, and day 21) and terminated the experiment at day 21.

Statistical Analysis. Data were analyzed in R version 4.0.3 and graphed in GraphPad Prism 6. Detailed statistical information is included in the corresponding figure legends. Data were presented as mean±SEM. Comparisons were conducted via one way-ANOVA test, or an unpaired two-tailed Student's t-test with significant differences defined as P<0.05 (*), P<0.01 (), P<0.001 (*), and P<0.0001 (****). Our sample size (3 patients in each category) was based on the feasibility of handling this number of hiPSC lines. For dose response curves, log-logistic non-linear regression model was used to estimate the value of the four parameters, and t-statistic was used to test for significant difference in LD$_{50}$ between different groups using "drc" package[16] in R.

Results

Investigation of the Protective Role of Variant Rs7853758

Six well-phenotyped, doxorubicin-treated pediatric patients from the original CGAS cohort were specifically re-recruited according to the original inclusion criteria[17] (Table 1). These included three patients who were heterozygous for the rs7853758 variant and were protected from DIC (SLC$^{var1}$, SLC$^{var2}$, SLC$^{var3}$; collectively SLC$^{var}$), and three control patients who did not carry this protective variant (they carry the reference allele) and developed DIC after the DOX therapy (SLC$^{ref1}$, SLC$^{ref2}$, SLC$^{ref3}$; collectively SLC$^{ref}$). Detailed patient data including age, sex, ethnicity, type of cancer, treatment regimen, and presence or absence or DIC are provided in Table 2. hiPSC lines were established from patients' peripheral blood using non-integrating (Sendai virus-based) reprogramming and our well-established protocols[18, 19]. These lines showed normal hiPSC morphology (FIG. 6A), expressed high levels of undifferentiated cell markers (FIGS. 6B-6C), and were karyotypically normal (FIG. 7). The genotypes of the rs7853758 SNP were validated using Nanopore-based sequencing (FIG. 1A). Cardiomyocytes were generated using our established chemically defined, small molecule-based monolayer differentiation system[11, 20] (FIG. 8A), along with a TNNT2-based antibiotic selection cassette which consistently produces cardiomyocytes which are 80-98% TNNT2$^+$ (FIGS. 8B and 8D). hiPSC-CMs express SLC28A3 throughout the cell (FIG. 1B).

Patient-specific hiPSC-CMs recapitulate the cardioprotective effect of rs7853758 against DIC.

Figure 17A:
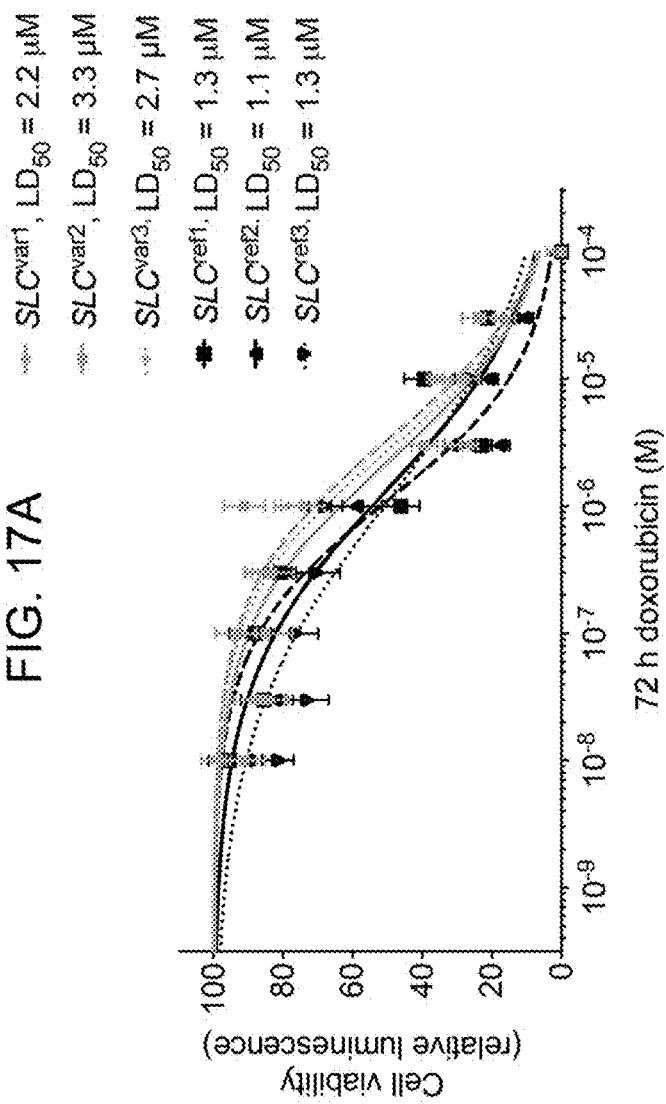
Figure 17B:
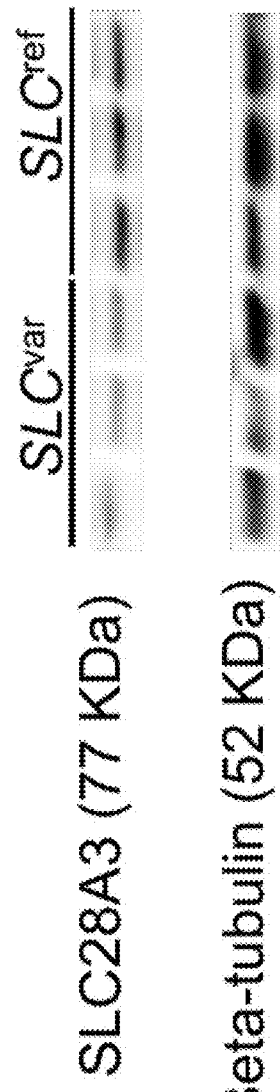

We first sought to model the cardioprotective effect of rs7853758 variant in patient-specific hiPSC-CMs. A cell viability assay completed at 72 h post DOX treatment demonstrated that the three SLC$^{var}$ lines recapitulated the protective effect of SNP (rs7853758 G>A, L461L) (LD$_{50}$=2.7 μM, P<0.0001, n=126) as compared to the SLC$^{ref}$ lines (LD$_{50}$=1.38 μM, n=81) (FIG. 1C and FIG. 17A). Consistently, apoptosis as quantified by a caspase-3 and -7 activity assay completed 72 h post DOX treatment was significantly lower in SLC$^{var}$ lines (IC$_{50}$=1 μM, P=0.001, n=20) compared to the SLC$^{ref}$ lines (IC$_{50}$=0.43 μM, n=20) (FIG. 1D). Since SLC28A3 is an uptake transporter, we hypothesized that the lower level of DIC in the SLC$^{var}$ lines might be due to reduced DOX uptake as a result of impaired SLC28A3 function in these patients. To test this, we used a flow cytometry-based assay and found that intracellular DOX uptake was ~50% lower in SLC$^{var}$ as compared to SLC$^{ref}$ (FIG. 1E), which is consistent with the magnitude LD$_{50}$ (1.38 µM vs. 2.7 µM) and IC$_{50}$ (0.43 µM and 1 µM) changes on our in vitro DIC assays (FIG. 1C). To investigate whether this cardioprotective effect seen in SLC$^{var}$ is due to altered SLC28A3 protein expression, we then quantified SLC28A3 in our patient-specific hiPSC-CMs using western blot. SLC28A3 expression in SLC$^{var}$ was significantly lower than SLC$^{ref}$ (P=0.03) (FIG. 1F, and FIG. 17B).

SLC28A3 altered expression affects doxorubicin-induced cardiotoxicity in hiPSC-CMs.

Figure 2A:
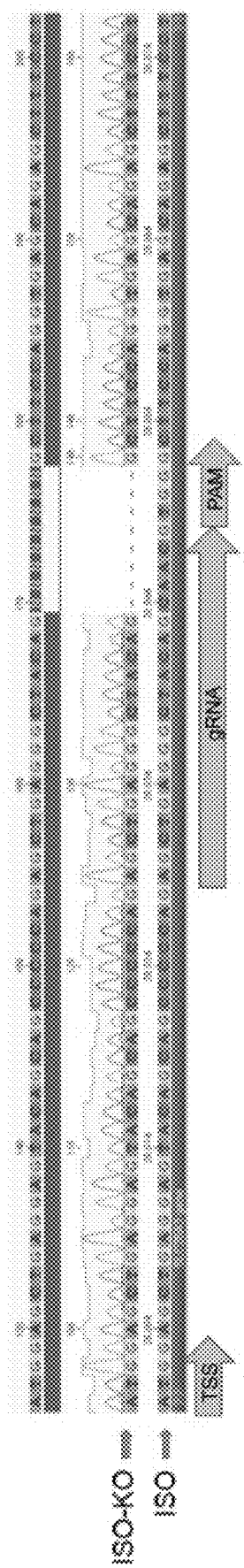
Figure 2C:
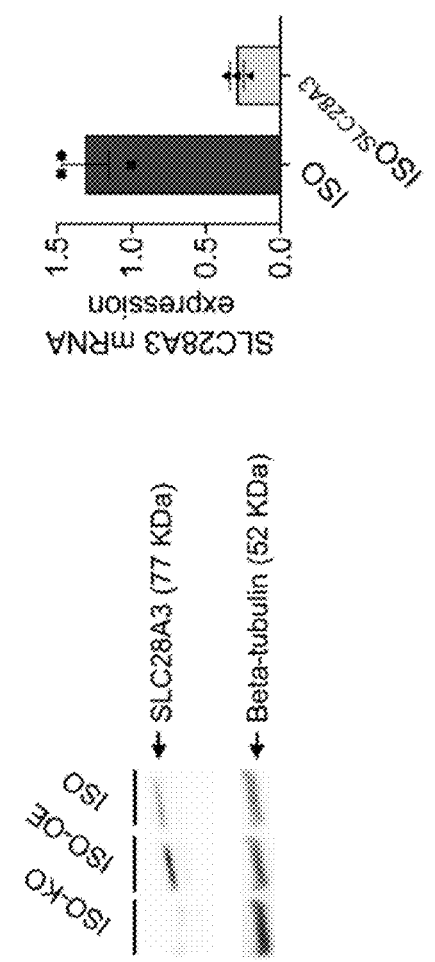
Figure 2B:
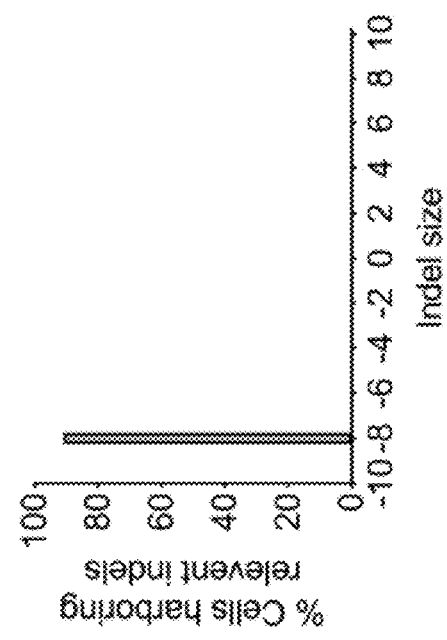

To further confirm the implication of SLC28A3 in DIC regardless of patient-specific genetic, transcriptomic, and environmental background and to isolate the effect of SLC28A3 in relation to DIC, we next examined whether a gain or loss of function of SLC28A3 altered DIC in an isogenic hiPSC line (ISO). The ISO line was derived from a healthy individual and its whole genome sequencing confirmed that it doesn't harbor any other DIC-associated loci identified by the original study. SLC28A3 overexpression (ISO-OE) and knockout (ISO-KO) lines were generated via a CRISPR/Cas9-mediated approach. Disturbance at start codon region was confirmed by Sanger sequencing (FIGS. 2A-2B) and altered SLC28A3 expression in these lines was confirmed by RT-PCR and western blot showing 90% downregulation of SLC28A3 in ISO-KO (FIG. 2C). The effect of SLC28A3 OE and KO on in vitro DIC was investigated using the above cell viability and caspase assays at 72 h post DOX treatment. The cell viability assay showed that the ISO-OE hiPSC-CMs (LD$_{50}$=0.9 µM) were ~3.3-fold and 1.4-fold more sensitive to DOX as compared to ISO-KO (LD$_{50}$=4 µM, P=0.03) and ISO (LD$_{50}$=2.5 µM, P<0.0001), respectively (FIG. 2D). Likewise, caspase activity was ~2.6-fold higher in ISO-OE (LD$_{50}$=0.14 µM) as compared to ISO (LD$_{50}$=0.53 µM, P<0.0001) (FIG. 2E). We next sought to investigate the effect of SLC28A3 KO and OE on DOX intracellular uptake. DOX uptake was significantly higher in ISO-OE as compared to ISO both at 1 h (P=0.035) and 3 h (P<0.0017) post DOX treatment (FIG. 2F). Similarly, DOX uptake was significantly lower in ISO-KO as compared to ISO both at 1 h (P=0.0009) and 3 h (P=0.0006) post DOX treatment (FIG. 2F). These findings show that SLC28A3 is implicated in DIC regulation through affecting DOX uptake into cardiomyocytes.

Figure 3A:
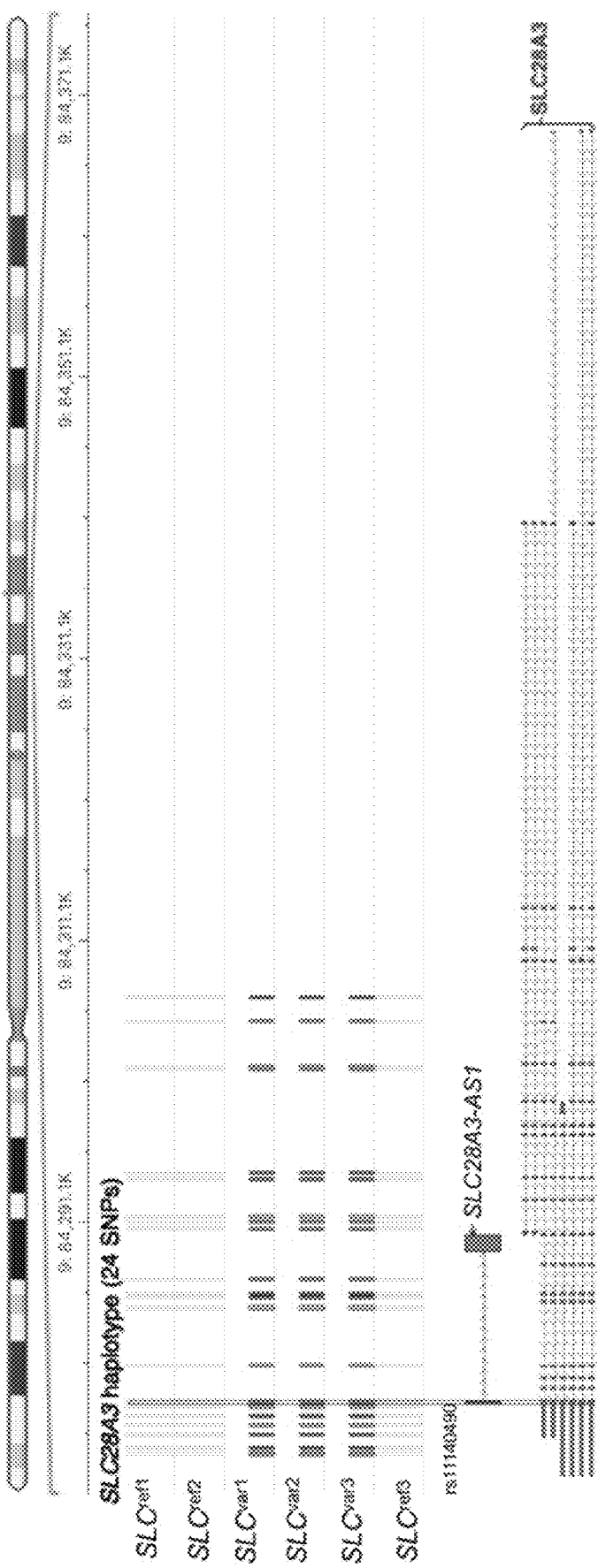
Figure 9A:
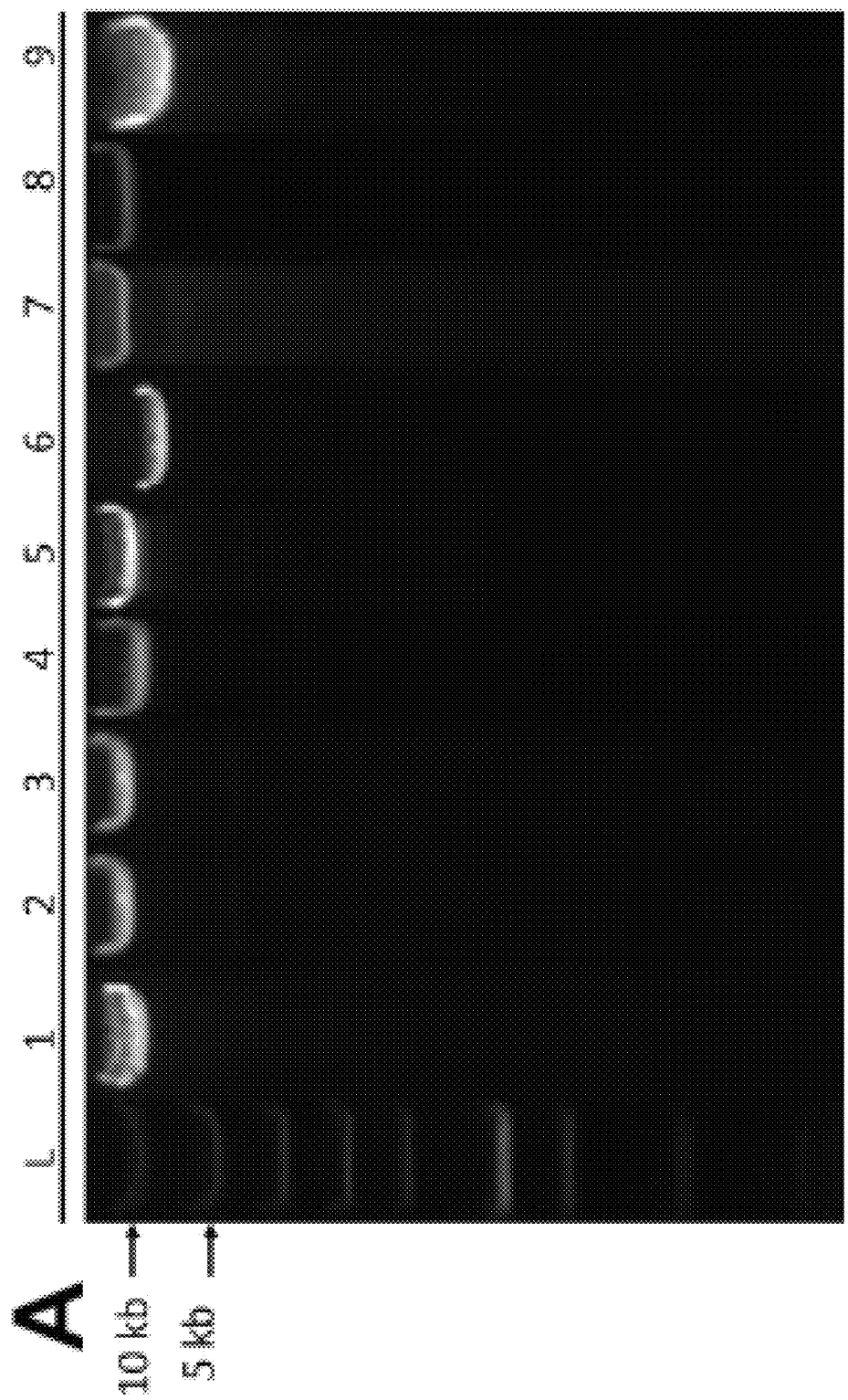
Figure 9B:
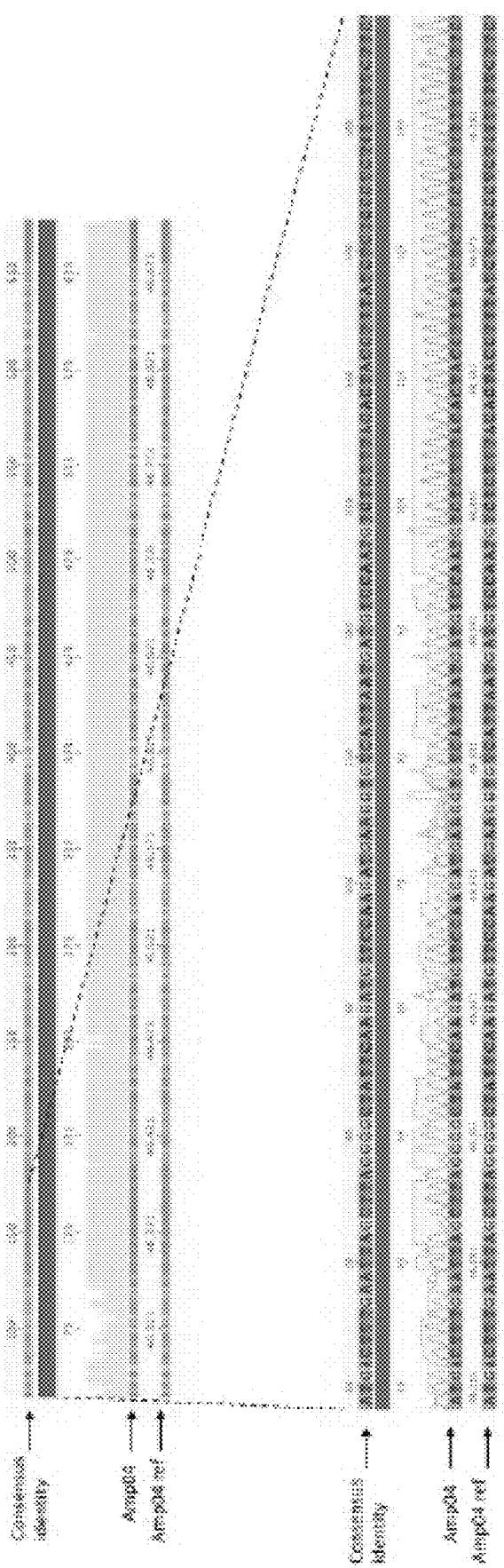
Figure 9F:
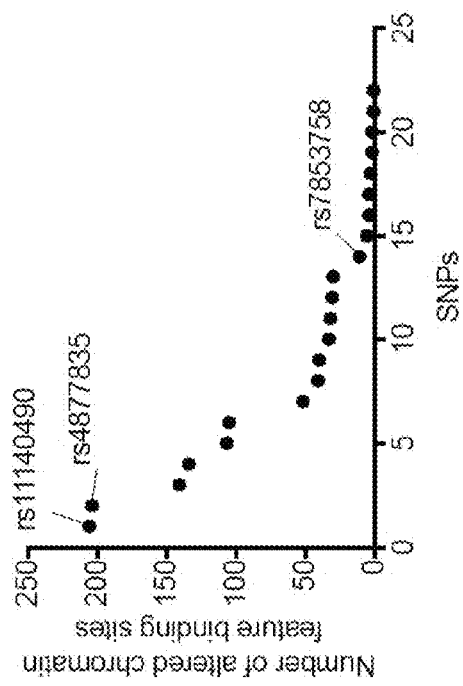
Figure 9E:
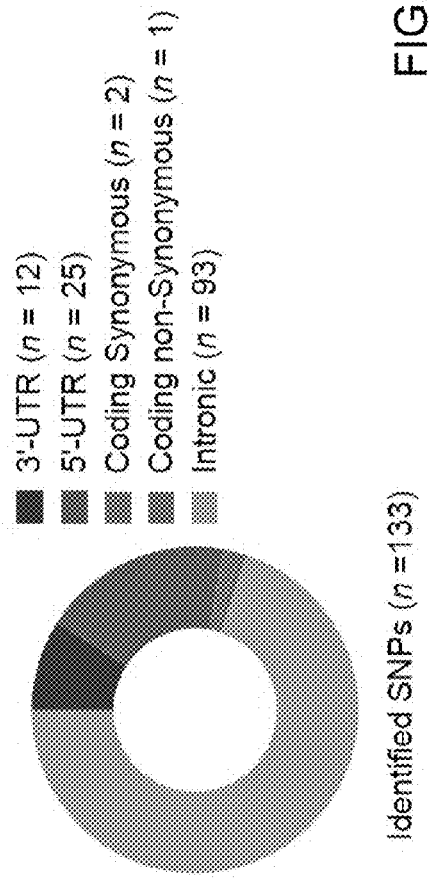

Fine mapping at the SLC28A3 locus prioritizes potential causal variant.

rs7853758 is a coding synonymous SNP located in exon 14 and thus does not affect the amino acid sequence. Because of the tag-SNP and linkage disequilibrium (LD) issues associated with GWAS[21], we expected that rs7853758 is linked (coinherited) to additional SNPs including the causal one(s). To elucidate this, we next fine-mapped the SLC28A3 locus to identify the potential causal variant. We sequenced the SLC28A3 gene in all six SLC$^{var}$ and SLC$^{ref}$ patients using a Nanopore MinION sequencer and SNPs were called using Nanopolish[22]. For all patients, Nanopore genotypes of the original association study hit, rs7853758 were in concordance with the GWAS-chip genotypes (FIG. 1A). In total 133 SNPs were identified all of which have at least one variant allele in at least one patient (FIG. 9E). The vast majority of identified SNPs were intronic (n=93), 25 SNPs were located in 5'-UTR, 12 SNPs were located in 3'-UTR, in addition to three coding SNPs of which two were synonymous and one non-synonymous (Table 6). We then examined which SNPs were exclusively co-inherited in cardioprotected patients and identified a cardioprotective haplotype, Hap$^{SLC28A3}$ comprising 24 SNPs that is co-inherited only in cardioprotected patients. These SNPs are distributed as follows, eight SNPs are located in the 3'-UTR, 14 SNPs are intronic, and two are coding synonymous SNPs (FIGS. 3a-b and Table 6).

Interestingly, seven SNPs within Hap$^{SLC28A3}$ are located within a long non-coding RNA, ensemble gene id: ENSG00000233262 that we called "SLC28A3-AS1" (submitted to HGNC registry) that overlaps with SLC28A3 forming another haplotype, Hap$^{SLC28A3-AS1}$ (FIG. 3A, FIGS. 9A-9B). Hap$^{SLC28A3-AS1}$ consists of SNPs, rs11140490 (A>G), rs10868135 (T>C), rs4877831 (C>G), rs4877833 (T>C), rs7853066 (A>G), rs7853758 (G>A), and rs7030019 (A>G).

In order to validate and confirm the linkage disequilibrium pattern of the Nanopore-identified cardioprotective haplotype, Hap$^{SLC28A3}$, we investigated the haplotype structure and allelic frequency of this cardioprotective haplotype on a wider population level in 99 individuals of the CEU (Utah Residents (CEPH) with Northern and Western European Ancestry) population, the same ethnic population of the study cohort. This analysis showed that the 24 SNPs constituting the Hap$^{SLC28A3}$ were in high LD with an average D' and R$^2$ of 0.99 and 0.84, respectively (FIGS. 9A-9B and Table 11). Regarding Hap$^{SLC28A3-AS1}$, seven structures were identified, Hap-I$^{SLC28A3-AS1}$ to Hap-VII$^{SLC28A3-AS1}$ (FIG. 10C). In that, Hap-I$^{SLC28A3-AS1}$ consists of the reference alleles for all seven SNPs (ATCTAGA) and is inherited in 71.7% of the examined population, whereas Hap-II$^{SLC28A3-AS1}$ comprises the variant alleles for all seven SNPs (GCGCGAG) and is inherited in 17.7% of the examined population (FIG. 10C). This finding confirms the linkage disequilibrium pattern identified by the Nanopore pipeline in all of the study patients.

To eliminate the probability that the causal variant might be located in one of the adjacent genes to the SLC28A3/SLC28A3-AS1 target locus, we did an extended LD analysis to include all variants that are located with 1 MB up and down-stream of the target locus in both European (the same ethnic population of the original genotype-phenotype association study) and all ethnicity populations. These analyses did not identify any other SNPs that are linked to rs7853758 and are not included in our original haplotype analysis. This eliminates the probability that the causal cardioprotective variant is located in adjacent genes (FIG. 11).

Figure 9G:
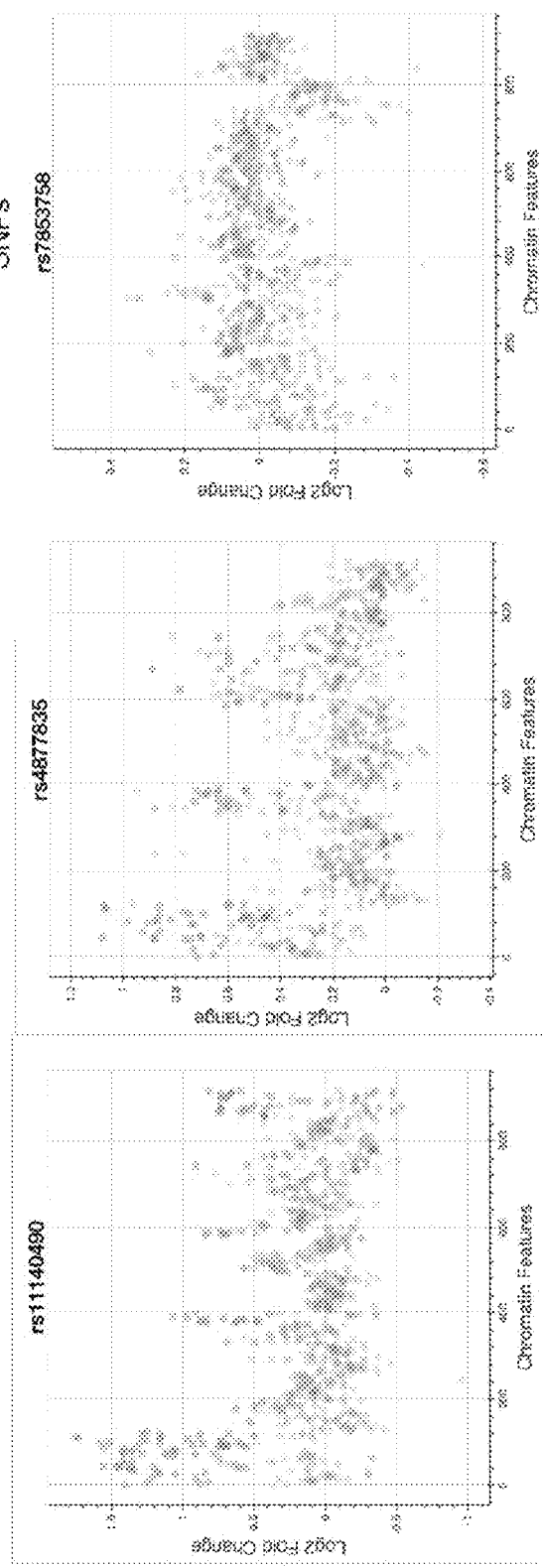

In order to prioritize cardioprotective haplotype SNPs, we investigated the regulatory properties of all candidate SNPs (n=24). Using the Encyclopedia of DNA Elements (EN-CODE) and Roadmap Epigenomics[23] data and DeepSEA[24] algorithm, we examined the functional effect of each SNP on altering chromatin features (transcription factors, DNase hypersensitive site, and histone marks) binding sites. Among all SNPs, rs11140490 and rs4877835 had the top chromatin regulatory effect as both SNPs predicted to alter the binding site of 206 and 204 chromatin features, respectively (FIG. 9F, Tables 7 and 8). Moreover, SNP rs11140490 has the most substantial regulatory effect as it is predicted to alter the binding sites of 43 features with log$_2$ fold change of ≥1, whereas rs4877835 is predicted to alter the binding sites of only 4 features with log$_2$ fold change of ≥1. Unsurprisingly, the primary study significant association, rs7853758 does not show any significant chromatin regulatory effect (FIG. 9G).

Since DIC affects cardiomyocytes, we performed an additional regulatory analysis exclusively focusing on human cardiac tissue, and for that we used ensemble regulatory build that includes transcription factors, histone mark, and DNase hypersensitive regions. Six SNPs, rs11140490, rs4877835, rs4877831, rs7047898, rs885004, and rs10868137 were found to be located in at least one regulatory region in human cardiac tissue (Table 9). Finally, to investigate further regulatory consequences of these candidate SNPs, we used the Genotype-Tissue Expression (GTEx) project database (https://www.gtexportal.org/home/) to investigate which of the identified candidate SNPs have been shown to be an expression quantitative trait loci (eQTL). All candidate SNPs except rs7858075 have been previously identified as eQTL in cultured fibroblasts, thyroid, and brain tissues (Table 10). Although the eQTLs identified by the GTEx are located in non-cardiac tissues, these associations emphasize the regulatory function of these SNPs. These findings when taken together suggest that SNP rs11140490, interestingly located at the splice site of the first exon of SLC28A3-AS1, is the SNP with the highest likelihood to be the causal cardioprotective SNP (FIG. 3C).

Editing rs11140490 in hiPSC-CMs confirms its causality in relation to protection against DIC.

After we prioritized rs11140490 to be the top candidate causal variant within the DIC-associated SLC28A3-SLC28A3-AS1 locus, we went on to confirm the causality of this variant. Using a base-editor mediated approach, we edited the SNP rs11140490 in hiPSCs from two SLC$^{var}$ patients that harbor the heterozygous genotype CT back to the reference genotype TT. The cytosine base editor that we have used is composed of a catalytically inactive "dead" Cas9 (dCas9) fused to (CBE) cytidine deaminase that converts C•G base pair to a T•A base pair. Importantly, the CBE does not induce a DNA cut and thus helped us avoid the mono-allelic genomic deletions and loss-of-heterozygosity problem associated with the homology directed repair (HDR)-based genomic editing approaches[25]. Positive hiPSC clones were differentiated into cardiomyocytes and finally DIC and DOX uptake were quantified using the above assays. SLC$^{rs11140490(CT>TT)}$ cardiomyocytes were more sensitive to DOX (LD$_{50}$=1.37 µM, P=0.005) as compared to SLC$^{rs11140490(CT)}$ LD$_{50}$=1.9 µM) (FIG. 3E). Moreover, DOX uptake was significantly higher in SLC$^{rs11140490(CT>TT)}$ when compared to SLC$^{rs11140490(CT)}$ at 3 h post DOX treatment (P=0.006) (FIG. 3F). This finding confirms that the SNP rs11140490 is the causal cardioprotective SNP affecting DIC.

Variant rs11140490 exert its cardioprotective effect by regulating the long non-coding RNA, SLC28A3-AS1.

Figure 4A:
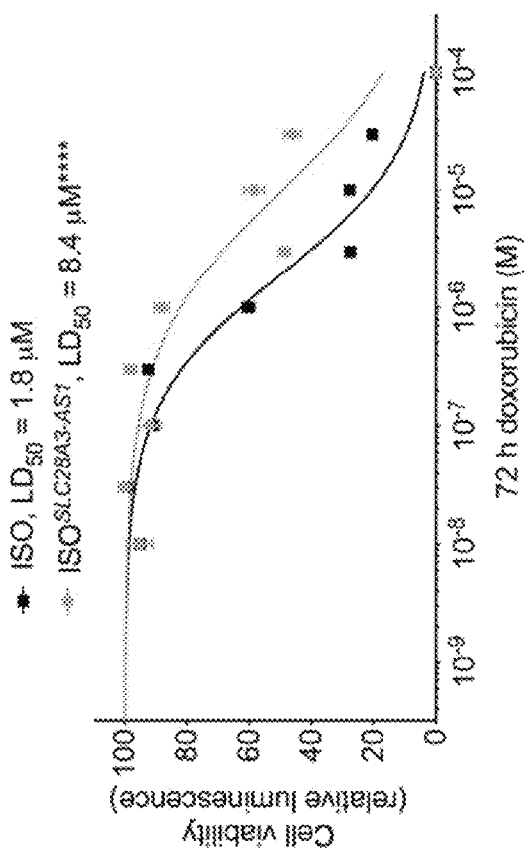
Figure 4B:
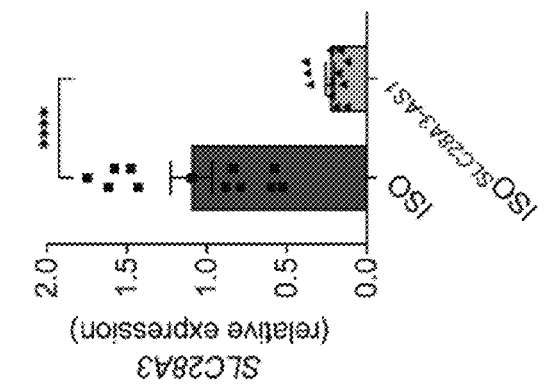
Figure 4C:
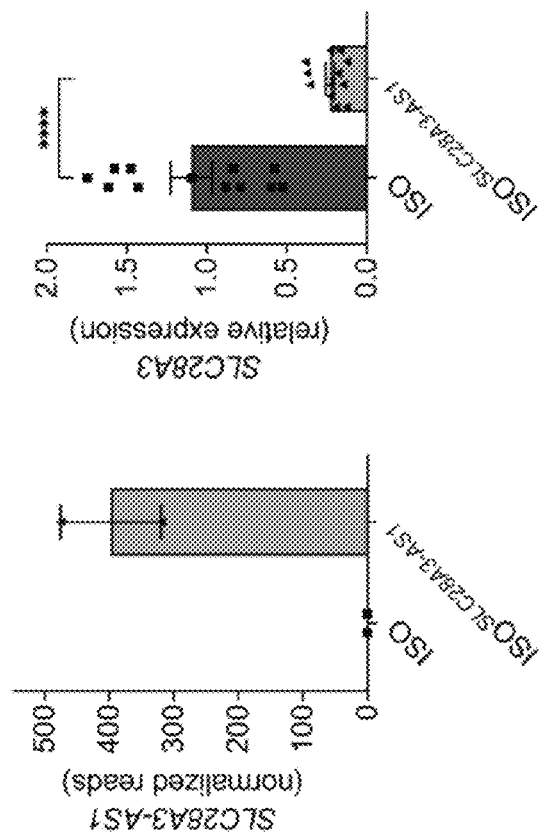

Next, we investigated the cardioprotective mechanism of rs11140490. This variant is located at the splice site of the first exon of the anti-sense SLC28A3-AS1 that overlaps with SLC28A3. Thus, we hypothesized that SNP rs11140490 might exert its cardioprotective action via regulating the transcription of SLC28A3-AS1, which in turn alters the expression of doxorubicin-related genes including SLC28A3, and eventually alters patients' susceptibility to DIC. To test this hypothesis, we investigated the effect of altered expression of SLC28A3-AS1 on DIC phenotype. We overexpressed SLC28A3-AS1 in an isogenic cell line (ISO$^{SLC28A3-AS1}$) by transducing isogenic hiPSCs with the SLC28A3-AS1 cDNA cloned into pLenti-MYC-DDK-IRES-Puro lentivirus expression vector (ORIGENE, PS100069). SLC28A3-AS1 overexpression was confirmed by stranded RNA-Seq after ribosomal RNA depletion (FIG. 4A). We then assessed the effect SLC28A3-AS1 overexpression on SLC28A3 expression in cardiomyocytes and showed that SLC28A3 is significantly downregulated in ISO$^{SLC28A3-AS1}$ cardiomyocytes after DOX treatment (FIG. 4B). We then investigated the effect of SLC28A3-AS1 overexpression on DIC and DOX uptake as before. ISO$^{SLC28A3-AS1}$ hiPSC-CMs were significantly more resistant to DOX (LD$_{50}$=8.4 µM, P<0.0001) as compared to ISO (LD$_{50}$=1.8 µM) (FIG. 4C). Moreover, DOX uptake was significantly impaired in ISO$^{SLC28A3-AS1}$ cardiomyocytes when compare to ISO both at 1 h (P=0.001) and 3 h (P<0.001) post DOX treatment (FIG. 4D). These results show that the regulation of SLC28A3-AS1 is a potential mechanism by which SNP rs11140490 exerts its cardioprotective effect.

Implication of other SLC transporters in DIC regulation.

After we provided proof of principle for the importance of SLC transporters in DIC by showing that SLC28A3 expression and genomic variants affect the severity of DIC, we examined other potential SLC transporters that might affect DIC. To date, there are more than 450 identified SLC transporters, 12 of which have been shown to either transport DOX or a DOX metabolite and/or their genes harbor SNPs that are significantly associated with DOX clinical outcomes[26]. We examined which of these 12 SLC transporters are expressed in adult heart tissue, fetal heart tissue, and hiPSC-CMs. Only three additional SLC transporters met these criteria, SLC22A4, SLC22A3, SLC22A17 were selected for further investigation (FIG. 4E). For each of these transporters, we generated CRISPR/Cas9-mediated KO hiPSC (SLC22A4$^{KO}$, SLC22A3$^{KO}$, and SLC22A17$^{KO}$) and differentiated them to cardiomyocytes (FIG. 12). We examined the effect of altered expression of each candidate transporter on DOX intracellular uptake and cell viability after DOX treatment. Expectedly, SLC22A3, SLC22A4, SLC28A3, and SLC22A17 knockout resulted in a significant decrease in DOX uptake in isogenic hiPSC-CMs (FIG. 4F). DIC quantification revealed that SLC22A4$^{KO}$ cardiomyocytes (LD$_{50}$=3.8 µM, P<0.0001, n=58), SLC28A3$^{KO}$ cardiomyocytes (LD$_{50}$=3.3 µM, P<0.0001, n=17), and SLC22A17$^{KO}$ cardiomyocytes (LD$_{50}$=3 µM, P=0.005, n=10) were less sensitive to DOX and more protected against DIC as compared to ISO (LD$_{50}$=1.9 µM, P<0.0001, n=128). Whereas, knocking out SLC22A3 had a detectable yet not significant effect on DIC (LD$_{50}$=2.1 µM, P=0.5, n=17) (FIG. 4G).

High-throughput drug screening reveals the SLC inhibitor, desipramine as a novel cardioprotective drug against DIC in hiPSC-CMs and murine.

Since SLC transporters affect DIC and represent well-founded druggable targets, we went on to examine whether SLC substrates can alter DOX uptake and subsequently regulate DIC in hiPSC-CMs. To test this, we first screened 17 drugs with well-established roles in affecting SLC transporter efficacy in relation to DOX uptake (Table 12). In order eliminate potential toxicity from high doses of the SLC substrate drugs, LD$_{50}$ was determined in our ISO cardiomyocytes for the 17 drugs to determine relevant maximum tolerable dose (FIG. 13). This screening revealed that desipramine was the only substrate that altered DOX uptake at both 1 h and 3 h post DOX treatment. DOX uptake was significantly lower in cells co-treated with desipramine (3 µM) plus doxorubicin (3 µM) as compared to cells treated with doxorubicin (3 µM) only, after 1 h (P=0.008) and 3 h (P=0.04) posttreatment (FIGS. 14A-14B). Since desipramine significantly decreased doxorubicin transport into cardiomyocytes, we next inspected whether lower doxorubicin intracellular concentration in desipramine pre-treated cells affect the magnitude of DIC.

Figure 5A:
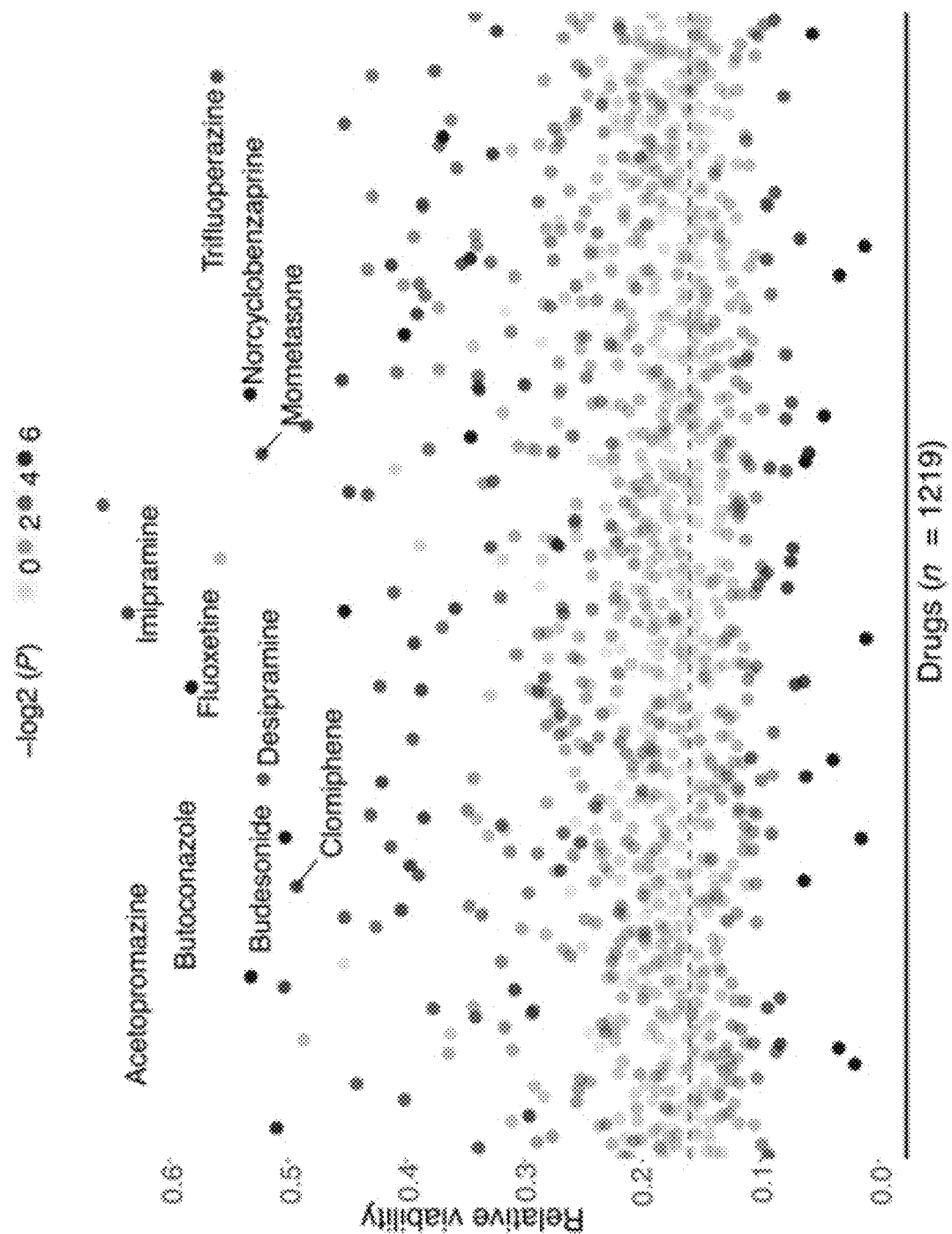

Next, we sought to expand our screening for novel cardioprotectants by testing the cardioprotective role of the Prestwick drug library that includes 1219 drugs. Cells were pre-treated with 3 µM of relevant drugs for 24 h, then co-treated with relevant drug (3 µM) and doxorubicin (10 µM) for 72 h after which DIC was quantified. For each plate, untreated and doxorubicin (10 µM) only treated cells were included to serve as negative and positive controls, respectively. Drug library screening reveled 34 cardioprotective molecules that attenuated cell death after DOX treatment (FIG. 5A). Drug repurposing is significantly faster and more cost-effective than de novo drug discovery approaches, and thus we focused on the top FDA-approved drugs identified from our screening. Interestingly, the top ten significant cardio-protectants included six FDA approved drugs; fluoxetine, butoconcazole, perospirone, tetracaine, propofol, and desipramine (FIG. 5B), of these drugs, desipramine again showed the most significant protection against DOX-induced cardiomyocyte death (P=0.007, 2.5-fold) (FIG. 5A-5B). To further validate these results, we then investigated the cardioprotective effect of these FDA-approved cardioprotective drugs against 10 log-doses of doxorubicin. This analysis showed that desipramine has the strongest cardioprotective effect when compared to cells treated only with DOX ($LD_{50}$=10.66 µM, P<0.0001), followed by propofol ($LD_{50}$=4.77 µM, P=0.003), then tetracaine ($LD_{50}$=4.65 µM, P<0.001), then butoconazole ($LD_{50}$=4.4 µM, P=0.01) (FIG. 5C-5D, FIG. 14C).

Based on these findings, we selected desipramine as our lead cardioprotective drug, and thus we then investigated whether or not desipramine could attenuate DIC in vivo. For that, we treated mice with doxorubicin (3 mg $kg^{-1}$ intraperitoneal twice weekly for 3 weeks) plus desipramine (20 mg $kg^{-1}$ $day^{-1}$ infusion for 3 weeks), or water as a vehicle control. Doxorubicin treatment results in a steady decline in cardiac function, as assessed by fractional shortening. Critically, cardiac function was significantly less attenuated by doxorubicin at three weeks with desipramine (P<0.05), compared with vehicle treatment (FIG. 5E-5F, FIGS. 17B-17C, and Table 13). To rule out the possibility that desipramine could diminish DOX chemotherapeutic effect, we studied eight cancer cell lines, representing breast, liver, colorectal, prostate, uterus, cervix, and bone cancers and found that co-treatment with desipramine did not impede the anticancer efficacy of DOX in any of these lines (FIG. 5F, and FIG. 15).

Discussion

The identification of reliable predictive genomic biomarkers for DIC and the discovery of efficient cardioprotectants are indispensable to enhance the clinical utility of doxorubicin in cancer treatment. The identification of gene variants predictive of altering DIC through GWAS has provided impetus for developing platforms to confirm these GWAS hits, moving them from 'association' to 'confirmed mechanism'. In this work we demonstrated that the patient-specific hiPSC-CM model is ideal for studying the implication of transporter inhibitors and genetic variants in DIC. We show that patient-specific cardiomyocytes do indeed recapitulate the cardioprotective effect of the CGAS-identified SLC28A3 locus; confirm for the first time the role of SLC28A3 in DIC independent of patient-specific genetic background; and critically reveal that another SNP within this cardioprotective locus, rs11140490 has the highest likelihood to be causal. Furthermore, this platform allowed us to discover that the SLC competitive inhibitor, desipramine protects against DIC without hampering DOX chemotherapy efficacy.

The SLC28A3 genetic variant rs7853758 is the most robustly replicated AIC strongly associated cardioprotective loci. We show that rs7853758 is in perfect LD with 23 other SNPs of which 22 are non-coding variants, forming the cardioprotective $Hap^{SLC28A3}$. Pinpointing causal SNP within this locus is crucial for clinical translation because testing for the causal variant guarantees the detection of the best possible clinical correlation with AIC. Almost 93% of phenotype-associated genetic variants are non-coding[27]. Using the ENCODE project dataset, it has been shown that ~80% of GWAS-identified non-coding SNPs are not the causal SNP[28]. Using our recently developed cost-effective fine mapping pipeline[29], we found that rs11140490, but not the CGAS-identified hit rs7853758, is the variant with the highest likelihood to be causal in DIC.

Editing only the rs11140490 cardioprotective genotype (CT) back to the reference genotype (TT) in patient-specific hiPSC-CMs renders these cardiomyocytes more susceptible to DIC confirming the causality of this novel variants. Interestingly, editing rs11140490 increase the sensitivity of hiPSC-CMs by ~28% which is modest and thus denotes that there might be more SNPs within the $Hap^{SLC28A3}$ that interact in an additive manner with rs11140490 to predispose to protection against DIC Going forward, we propose that a simple clinical test to detect the presence of rs11140490 can be used to predict that a patient will be less likely to experience DIC and that, with future clinical trials, it may be possible for these patients to be treated with a longer duration (higher cumulative dose) of doxorubicin to enhance the efficacy of their chemotherapy. Similarly, the rs11140490 genetic testing could be employed as a part of a polygenic cardiotoxicity risk stratification score for doxorubicin-containing chemotherapy regimens such that the protective effect of rs11140490 could balance out for a risk factor that would have otherwise prevented the administration of a relevant doxorubicin-containing chemotherapy regimen to a particular patient.

SLC28A3 encodes a cardiac-specific uptake transporter that has no/marginal expression in several cancer cells and hence, represents a highly druggable target to screen for cardioprotective agents. A large number of drugs have been identified as being trafficked by SLC transporters which explains the substantial role of these transporters in both drug pharmacokinetics and pharmacodynamics and emphasizes the importance of this class of transporters in drug response disposition[30]. Our high-throughput drug screening discovered that treating patient-specific cardiomyocytes with the SLC inhibitor desipramine protects against DIC through decreasing the intracellular uptake of DOX into human heart. Our results suggest that a single dose of 3 µM desipramine 24 h before the administration of DOX in addition to another dose of 3 µM desipramine co-administered with DOX is sufficient for protecting against DIC.

Desipramine is a tricyclic antidepressant sold under that brand name Norpramin, that was first patented in 1962[31]. The typical adult dose of desipramine 100 mg to 200 mg/day. In more severely ill patients, dosage may be further increased gradually to 300 mg/day if necessary. The typical therapeutic concentration is 100-300 ng/ml with daily dosing. Our 3 µM in vitro dose would be 798 ng/ml, but importantly, our preliminary data suggest that just two doses or potentially one dose per cycle of doxorubicin would be required to attenuate DIC. We would therefore suggest that these desipramine doses are potentially within the acceptable clinical range, although further animal model work to confirming dosing strategy is required prior to clinical trial.

Desipramine is far from an ideal drug, being the most potent sodium channel blocker among its group and causing cardiotoxicity when used chronically. Desipramine-treated patients have been shown to have significantly lower rates of sinus pauses and junctional rhythm, but significantly higher rates of single or paired premature atrial contractions and runs of supraventricular tachycardia as well as lengthening of the QT interval. The solution to this is to develop a desipramine derivative without the sodium channel blockade effect, although approach eliminates the primary advantage of repurposing a drug like desipramine to attenuate DIC. Still, the advantage of using our hiPSC-CM platform for subsequent testing will be a major advantage in such an effort The majority (56%) of candidate drugs have failed in clinical trial due to the lack of efficacy, most likely because the pre-clinical models used to test the drug does not recapitulate what happens in humans[32] or in the specific target cell type. Additionally, studies staring with genetic correlations in genes encoding targets increases the success rate in clinical development by 2-fold[33]. Patient-derived hiPSC-CMs provides a unique platform that firstly permits a thorough validation of GWAS-identified AIC-associated loci, and secondly recapitulate alteration in DIC phenotype in a human-relevant manner. Hence the utilization of hiPSC-CMs in the development of cardioprotectants substantially improves the potential of developing novel derivatives of desipramine that have the same SLC28A3 competitive inhibition effect as desipramine without the well-known side effects common to the tricyclic antidepressant drug family.

Clearly hiPSC-CMs do not fully mimic the human whole-body model and do not recapitulate all the steps of drug pharmaco-kinetics and -dynamics. However, current hiPSC-CM generation methodologies have enhanced the robustness, purity, maturation, and scalability to a point where these cells are suitable for a wide-range of disease modelling and drug response assays[34-42]. Here we demonstrated that patient-specific cardiomyocytes recapitulate intra-individual variability in genomic-dependent DIC susceptibility. We show that hiPSC-CMs are appropriate to study drug response-associated loci especially for genes with a known mechanism of action such as transporter-encoding genes. The integration of CRISPR/Cas9-based genetic editing to our patient-specific hiPSC model proves to be a powerful tool in identify causal genetic variations in relation to a specific drug-response. The expansion of the utility of patient-specific hiPSC-CMs to study additional anthracycline-relevant loci as well as those of other anti-cancer agents will help to identify patients/population-specific chemotherapeutic-induced cardiotoxicity genetic biomarkers and new cardioprotective agents. Ultimately, the information derived from this platform may allow physicians to tailor chemotherapeutics doses based on patient genotype, bringing the promise of personalized medicine to the field of cardio-oncology.

REFERENCES

1. Cardinale D, Colombo A, Bacchiani G, Tedeschi I, Meroni C A, Veglia F, Civelli M, Lamantia G, Colombo N, Curigliano G, et al. Early detection of anthracycline cardiotoxicity and improvement with heart failure therapy. *Circulation.* 2015; 131:1981-8.
2. Swain S M, Whaley F S and Ewer M S. Congestive heart failure in patients treated with doxorubicin: A retrospective analysis of three trials. *Cancer.* 2003; 97:2869-2879.
3. Avila M S, Ayub-Ferreira S M, de Barros Wanderley M R, Jr., das Dores Cruz F, Goncalves Brandao S M, Rigaud V O C, Higuchi-Dos-Santos M H, Hajjar L A, Kalil Filho R, Hoff P M, et al. Carvedilol for Prevention of Chemotherapy-Related Cardiotoxicity: The CECCY Trial. *J Am Coll Cardiol.* 2018; 71:2281-2290.
4. Magdy T, Burmeister B T and Burridge P W. Validating the pharmacogenomics of chemotherapy-induced cardiotoxicity: What is missing? *Pharmacol Ther.* 2016.
5. Aminkeng F, Ross C J D, Rassekh S R, Rieder M J, Bhavsar A P, Sanatani S, Bernstein D, Hayden M R, Amstutz U and Carleton B C. Pharmacogenomic screening for anthracycline-induced cardiotoxicity in childhood cancer. *Br J Clin Pharmacol.* 2017; 83:1143-1145.
6. Tan L L and Lyon A R. Role of Biomarkers in Prediction of Cardiotoxicity During Cancer Treatment. *Curr Treat Options Cardiovasc Med.* 2018; 20:55.
7. Visscher H, Ross C J D, Rassekh S R, Barhdadi A, Dubé M-P, Al-Saloos H, Sandor G S, Caron H N, van Dalen E C, Kremer L C, et al. Pharmacogenomic prediction of anthracycline-induced cardiotoxicity in children. *J Clin Oncol.* 2012; 30:1422-1428.
8. Visscher H, Ross C J D, Rassekh S R, Sandor G S S, Caron H N, van Dalen E C, Kremer L C, van der Pal H J, Rogers P C, Rieder M J, et al. Validation of variants in SLC28A3 and UGT1A6 as genetic markers predictive of anthracycline-induced cardiotoxicity in children. *Pediatr Blood Cancer.* 2013; 60:1375-1381.
9. Aminkeng F, Ross C J D, Rassekh S R, Hwang S, Rieder M J, Bhavsar A P, Smith A, Sanatani S, Gelmon K A, Bernstein D, et al. Recommendations for genetic testing to reduce the incidence of anthracycline-induced cardiotoxicity. *Br J Clin Pharmacol.* 2016; 82:683-695.
10. Fusaki N, Ban H, Nishiyama A, Saeki K and Hasegawa M. Efficient induction of transgene-free human pluripotent stem cells using a vector based on Sendai virus, an RNA virus that does not integrate into the host genome. *Proc Jpn Acad Ser B Phys Biol Sci.* 2009; 85:348-62.
11. Burridge P W, Matsa E, Shukla P, Lin Z C, Churko J M, Ebert A D, Lan F, Diecke S, Huber B, Mordwinkin N M, et al. Chemically defined generation of human cardiomyocytes. *Nat Methods.* 2014; 11:855-60.
12. Burridge P W, Holmstrom A and Wu J C. Chemically Defined Culture and Cardiomyocyte Differentiation of Human Pluripotent Stem Cells. *Curr Protoc Hum Genet.* 2015; 87:2131-15.
13. Ran F A, Hsu P D, Wright J, Agarwala V, Scott D A and Zhang F. Genome engineering using the CRISPR-Cas9 system. *Nat Protoc.* 2013; 8:2281-308.
14. Oceguera-Yanez F, Kim S I, Matsumoto T, Tan G W, Xiang L, Hatani T, Kondo T, Ikeya M, Yoshida Y, Inoue H, et al. Engineering the AAVS1 locus for consistent and scalable transgene expression in human iPSCs and their differentiated derivatives. *Methods.* 2016; 101:43-55.
15. Dandage R, Despres P C, Yachie N and Landry C R. beditor: A Computational Workflow for Designing Libraries of Guide RNAs for CRISPR-Mediated Base Editing. *Genetics.* 2019.

16. Ritz C, Baty F, Streibig J C and Gerhard D. Dose-Response Analysis Using R. *PLoS ONE.* 2015; 10:e0146021.
17. Aminkeng F, Bhavsar A P, Visscher H, Rassekh S R, Li Y, Lee J W, Brunham L R, Caron H N, van Dalen E C, Kremer L C, et al. A coding variant in RARG confers susceptibility to anthracycline-induced cardiotoxicity in childhood cancer. *Nat Genet.* 2015; 47:1079-84.
18. Churko J M, Burridge P W and Wu J C. Generation of human iPSCs from human peripheral blood mononuclear cells using non-integrative Sendai virus in chemically defined conditions. *Methods Mol Biol.* 2013; 1036:81-8.
19. Diecke S, Lu J, Lee J, Termglinchan V, Kooreman N G, Burridge P W, Ebert A D, Churko J M, Sharma A, Kay M A, et al. Novel codon-optimized mini-intronic plasmid for efficient, inexpensive, and xeno-free induction of pluripotency. *Sci Rep.* 2015; 5:8081.
20. Burridge P W, Holmstrom A and Wu J C. Chemically Defined Culture and Cardiomyocyte Differentiation of Human Pluripotent Stem Cells. *Curr Protoc Hum Genet.* 2015; 87:2131-21315.
21. Magdy T and Burridge P W. The future role of pharmacogenomics in anticancer agent-induced cardiovascular toxicity. *Pharmacogenomics.* 2018; 19:79-82.
22. Loman N J, Quick J and Simpson J T. A complete bacterial genome assembled de novo using only nanopore sequencing data. *Nat Methods.* 2015; 12:733-5.
23. Kundaje A, Meuleman W, Ernst J, Bilenky M, Yen A, Heravi-Moussavi A, Kheradpour P, Zhang Z, Wang J, Ziller M J, et al. Integrative analysis of 111 reference human epigenomes. *Nature.* 2015; 518:317-30.
24. Zhou J and Troyanskaya O G. Predicting effects of noncoding variants with deep learning-based sequence model. *Nat Methods.* 2015; 12:931-4.
25. Weisheit I, Kroeger J A, Malik R, Klimmt J, Crusius D, Dannert A, Dichgans M and Paquet D. Detection of Deleterious On-Target Effects after HDR-Mediated CRISPR Editing. *Cell Rep.* 2020; 31:107689.
26. Magdy T, Burmeister B T and Burridge P W. Validating the pharmacogenomics of chemotherapy-induced cardiotoxicity: What is missing? *Pharmacol Ther.* 2016; 168:113-125.
27. Maurano M T, Humbert R, Rynes E, Thurman R E, Haugen E, Wang H, Reynolds A P, Sandstrom R, Qu H, Brody J, et al. Systematic localization of common disease-associated variation in regulatory DNA. *Science.* 2012; 337:1190-5.
28. Schaub M A, Boyle A P, Kundaje A, Batzoglou S and Snyder M. Linking disease associations with regulatory information in the human genome. *Genome Res.* 2012; 22:1748-59.
29. Magdy T, Kuo H H and Burridge P W. Precise and Cost-Effective Nanopore Sequencing for Post-GWAS Fine-Mapping and Causal Variant Identification. *iScience.* 2020; 23:100971.
30. Giacomini K M, Huang S M, Tweedie D J, Benet L Z, Brouwer K L, Chu X, Dahlin A, Evers R, Fischer V, Hillgren K M, et al. Membrane transporters in drug development. *Nat Rev Drug Discov.* 2010; 9:215-36.
31. Andersen J, Kristensen A S, Bang-Andersen B and Stromgaard K. Recent advances in the understanding of the interaction of antidepressant drugs with serotonin and norepinephrine transporters. *Chem Commun (Camb).* 2009:3677-92.
32. Arrowsmith J and Miller P. Trial watch: phase II and phase III attrition rates 2011-2012. *Nat Rev Drug Discov.* 2013; 12:569.
33. Nelson M R, Tipney H, Painter J L, Shen J, Nicoletti P, Shen Y, Floratos A, Sham P C, Li M J, Wang J, et al. The support of human genetic evidence for approved drug indications. *Nat Genet.* 2015; 47:856-60.
34. Itzhaki I, Maizels L, Huber I, Zwi-Dantsis L, Caspi O, Winterstern A, Feldman O, Gepstein A, Arbel G, Hammerman H, et al. Modelling the long QT syndrome with induced pluripotent stem cells. *Nature.* 2011; 471:225-229.
35. Malan D, Zhang M, Stallmeyer B, Müller J, Fleischmann B K, Schulze-Bahr E, Sasse P and Greber B. Human iPS cell model of type 3 long QT syndrome recapitulates drug-based phenotype correction. *Basic Res Cardiol.* 2016; 111.
36. Carvajal-Vergara X, Sevilla A, D'Souza S L, Ang Y-S, Schaniel C, Lee D-F, Yang L, Kaplan A D, Adler E D, Rozov R, et al. Patient-specific induced pluripotent stem cell derived models of LEOPARD syndrome. *Nature.* 2010; 465:808-812.
37. Yazawa M, Hsueh B, Jia X, Pasca A M, Bernstein J A, Hallmayer J and Dolmetsch R E. Using iPS cells to investigate cardiac phenotypes in patients with Timothy Syndrome. *Nature.* 2011; 471:230-234.
38. Kim C, Wong J, Wen J, Wang S, Wang C, Spiering S, Kan N G, Forcales S, Puri P L, Leone T C, et al. Studying arrhythmogenic right ventricular dysplasia with patient-specific iPSCs. *Nature.* 2013; 494:105-110.
39. Sun N, Yazawa M, Liu J, Han L, Sanchez-Freire V, Abilez O J, Navarrete E G, Hu S, Wang L, Lee A, et al. Patient-specific induced pluripotent stem cells as a model for familial dilated cardiomyopathy. *Sci Transl Med.* 2012; 4:130ra47.
40. Wang G, McCain M L, Yang L, He A, Pasqualini F S, Agarwal A, Yuan H, Jiang D, Zhang D, Zangi L, et al. Modeling the mitochondrial cardiomyopathy of Barth syndrome with induced pluripotent stem cell and heart-on-chip technologies. *Nat Med.* 2014; 20:616-623.
41. Magdy T and Burridge P W. Unraveling Difficult Answers: From Genotype to Phenotype in Coronary Artery Disease. *Cell Stem Cell.* 2019; 24:203-205.
42. Drawnel F M, Boccardo S, Prummer M, Delobel F, Graff A, Weber M, Gérard R, Badi L, Kam-Thong T, Bu L, et al. Disease modeling and phenotypic drug screening for diabetic cardiomyopathy using human induced pluripotent stem cells. *Cell Rep.* 2014; 9:810-821.
43. Chou B K, Gu H, Gao Y, Dowey S N, Wang Y, Shi J, Li Y, Ye Z, Cheng T and Cheng L. A facile method to establish human induced pluripotent stem cells from adult blood cells under feeder-free and xeno-free culture conditions: a clinically compliant approach. *Stem Cells Transl Med.* 2015; 4:320-32.
44. Kuo H H, Gao X, DeKeyser J M, Fetterman K A, Pinheiro E A, Weddle C J, Fonoudi H, Orman M V, Romero-Tejeda M, Jouni M, et al. Negligible-Cost and Weekend-Free Chemically Defined Human iPSC Culture. *Stem Cell Reports.* 2020; 14:256-270.
45. Kim D, Paggi J M, Park C, Bennett C and Salzberg S L. Graph-based genome alignment and genotyping with HISAT2 and HISAT-genotype. *Nat Biotechnol.* 2019; 37:907-915.
46. Liao Y, Smyth G K and Shi W. The Subread aligner: fast, accurate and scalable read mapping by seed-and-vote. *Nucleic Acids Res.* 2013; 41:e108.

47. Love M I, Huber W and Anders S. Moderated estimation of fold change and dispersion for RNA-seq data with DESeq2. *Genome Biol.* 2014; 15:550.
48. Schmittgen T D and Livak K J. Analyzing real-time PCR data by the comparative C(T) method. *Nat Protoc.* 2008; 3:1101-8.
49. Wick R R, Judd L M, Gorrie C L and Holt K E. Completing bacterial genome assemblies with multiplex MinION sequencing. *Microbial genomics.* 2017; 3:e000132.
50. De Coster W, D'Hert S, Schultz D T, Cruts M and Van Broeckhoven C. NanoPack: visualizing and processing long-read sequencing data. *Bioinformatics.* 2018; 34:2666-2669.
51. Li H. Minimap2: pairwise alignment for nucleotide sequences. *Bioinformatics.* 2018; 34:3094-3100.
52. Li H, Handsaker B, Wysoker A, Fennell T, Ruan J, Homer N, Marth G, Abecasis G and Durbin R. The Sequence Alignment/Map format and SAMtools. *Bioinformatics.* 2009; 25:2078-9.
53. Ramirez F, Ryan D P, Gruning B, Bhardwaj V, Kilpert F, Richter A S, Heyne S, Dundar F and Manke T. deepTools2: a next generation web server for deep-sequencing data analysis. *Nucleic Acids Res.* 2016; 44:W160-5.
54. Danecek P, Auton A, Abecasis G, Albers C A, Banks E, DePristo M A, Handsaker R E, Lunter G, Marth G T, Sherry S T, et al. The variant call format and VCFtools. *Bioinformatics.* 2011; 27:2156-8.
55. Cingolani P, Patel V M, Coon M, Nguyen T, Land S J, Ruden D M and Lu X. Using *Drosophila melanogaster* as a Model for Genotoxic Chemical Mutational Studies with a New Program, SnpSift. *Front Genet.* 2012; 3:35.
56. Narasimhan V, Danecek P, Scally A, Xue Y, Tyler-Smith C and Durbin R. BCFtools/RoH: a hidden Markov model approach for detecting autozygosity from next-generation sequencing data. *Bioinformatics.* 2016; 32:1749-51.
57. Durinck S, Spellman P T, Birney E and Huber W. Mapping identifiers for the integration of genomic datasets with the R/Bioconductor package biomaRt. *Nat Protoc.* 2009; 4:1184-1191.
58. Braun D, Kim T D, le Coutre P, Köhrle J, Hershman J M and Schweizer U. Tyrosine kinase inhibitors non-competitively inhibit MCT8-mediated iodothyronine transport. *The Journal of clinical endocrinology and metabolism.* 2012; 97:E100-5.
59. Damaraju V L, Weber D, Kuzma M, Cass C E and Sawyer M B. Selective Inhibition of Human Equilibrative and Concentrative Nucleoside Transporters by BCR-ABL Kinase Inhibitors: IDENTIFICATION OF KEY hENT1 AMINO ACID RESIDUES FOR INTERACTION WITH BCR-ABL KINASE INHIBITORS. *J Biol Chem.* 2016; 291:18809-17.
60. Braun D and Schweizer U. Authentic bosutinib inhibits triiodothyronine transport by monocarboxylate transporter 8. *Thyroid.* 2014; 24:926-7.
61. Yin J, Duan H and Wang J. Impact of Substrate-Dependent Inhibition on Renal Organic Cation Transporters hOCT2 and hMATE1/2-K-Mediated Drug Transport and Intracellular Accumulation. *J Pharmacol Exp Ther.* 2016; 359:401-410.
62. Tsuda M, Terada T, Ueba M, Sato T, Masuda S, Katsura T and Inui K. Involvement of human multidrug and toxin extrusion 1 in the drug interaction between cimetidine and metformin in renal epithelial cells. *J Pharmacol Exp Ther.* 2009; 329:185-91.
63. Shitara Y, Itoh T, Sato H, Li A P and Sugiyama Y. Inhibition of transporter-mediated hepatic uptake as a mechanism for drug-drug interaction between cerivastatin and cyclosporin A. *J Pharmacol Exp Ther.* 2003; 304:610-6.
64. Shitara Y, Takeuchi K, Nagamatsu Y, Wada S, Sugiyama Y and Horie T. Long-lasting inhibitory effects of cyclosporin A, but not tacrolimus, on OATP1B1- and OATP1B3-mediated uptake. *Drug Metab Pharmacokinet.* 2012; 27:368-78.
65. Craddock A L, Love M W, Daniel R W, Kirby L C, Walters H C, Wong M H and Dawson P A. Expression and transport properties of the human ileal and renal sodium-dependent bile acid transporter. *The American journal of physiology.* 1998; 274:G157-69.
66. Schroeder A, Eckhardt U, Stieger B, Tynes R, Schteingart C D, Hofmann A F, Meier P J and Hagenbuch B. Substrate specificity of the rat liver Na(+)-bile salt cotransporter in *Xenopus laevis* oocytes and in CHO cells. *The American journal of physiology.* 1998; 274: G370-5.
67. Taguchi T, Masuo Y, Kogi T, Nakamichi N and Kato Y. Characterization of Long-Lasting Oatp Inhibition by Typical Inhibitor Cyclosporine A and In Vitro-In Vivo Discrepancy in Its Drug Interaction Potential in Rats. *J Pharm Sci.* 2016; 105:2231-9.
68. Pahwa S, Alam K, Crowe A, Farasyn T, Neuhoff S, Hatley O, Ding K and Yue W. Pretreatment With Rifampicin and Tyrosine Kinase Inhibitor Dasatinib Potentiates the Inhibitory Effects Toward OATP1B1- and OATP1B3-Mediated Transport. *J Pharm Sci.* 2017; 106:2123-2135.
69. Xu Q, Wang C, Meng Q, Liu Q, Sun H, Peng J, Ma X, Kaku T and Liu K. OAT1 and OAT3: targets of drug-drug interaction between entecavir and JBP485. *European journal of pharmaceutical sciences: official journal of the European Federation for Pharmaceutical Sciences.* 2013; 48:650-7.
70. Kouzuki H, Suzuki H and Sugiyama Y. Pharmacokinetic study of the hepatobiliary transport of indomethacin. *Pharmaceutical research.* 2000; 17:432-8.
71. Takeda M, Khamdang S, Narikawa S, Kimura H, Hosoyamada M, Cha S H, Sekine T and Endou H. Characterization of methotrexate transport and its drug interactions with human organic anion transporters. *J Pharmacol Exp Ther.* 2002; 302:666-71.
72. Hu S, Mathijssen R H, de Bruijn P, Baker S D and Sparreboom A. Inhibition of OATP1B1 by tyrosine kinase inhibitors: in vitro-in vivo correlations. *Br J Cancer.* 2014; 110:894-8.
73. Taguchi T, Masuo Y, Sakai Y and Kato Y. Short-lasting inhibition of hepatic uptake transporter OATP1B1 by tyrosine kinase inhibitor pazopanib. *Drug Metab Pharmacokinet.* 2019; 34:372-379.
74. Oulianova N, Falk S and Berteloot A. Two-step mechanism of phlorizin binding to the SGLT1 protein in the kidney. *The Journal of membrane biology.* 2001; 179:223-42.
75. David-Silva A, Esteves J V, Morais M, Freitas H S, Zorn T M, Correa-Giannella M L and Machado U F. Dual SGLT1/SGLT2 Inhibitor Phlorizin Ameliorates Non-Alcoholic Fatty Liver Disease and Hepatic Glucose Production in Type 2 Diabetic Mice. *Diabetes, metabolic syndrome and obesity: targets and therapy.* 2020; 13:739-751.

76. Urakami Y, Akazawa M, Saito H, Okuda M and Inui K. cDNA cloning, functional characterization, and tissue distribution of an alternatively spliced variant of organic cation transporter hOCT2 predominantly expressed in the human kidney. *Journal of the American Society of Nephrology: JASN.* 2002; 13:1703-10.

77. Bednarczyk D, Ekins S, Wikel J H and Wright S H. Influence of molecular structure on substrate binding to the human organic cation transporter, hOCT1. *Mol Pharmacol.* 2003; 63:489-98.

78. Ohashi R, Tamai I, Yabuuchi H, Nezu J I, Oku A, Sai Y, Shimane M and Tsuji A. Na(+)-dependent carnitine transport by organic cation transporter (OCTN2): its pharmacological and toxicological relevance. *J Pharmacol Exp Ther.* 1999; 291:778-84.

79. van Montfoort J E, Müller M, Groothuis G M, Meijer D K, Koepsell H and Meier P J. Comparison of "type I" and "type II" organic cation transport by organic cation transporters and organic anion-transporting polypeptides. *J Pharmacol Exp Ther.* 2001; 298:110-5.

80. Cha S H, Sekine T, Fukushima J I, Kanai Y, Kobayashi Y, Goya T and Endou H. Identification and characterization of human organic anion transporter 3 expressing predominantly in the kidney. *Mol Pharmacol.* 2001; 59:1277-86.

81. Yabuuchi H, Tamai I, Nezu J, Sakamoto K, Oku A, Shimane M, Sai Y and Tsuji A. Novel membrane transporter OCTN1 mediates multispecific, bidirectional, and pH-dependent transport of organic cations. *J Pharmacol Exp Ther.* 1999; 289:768-73.

82. Nozawa T, Tamai I, Sai Y, Nezu J and Tsuji A. Contribution of organic anion transporting polypeptide OATP-C to hepatic elimination of the opioid pentapeptide analogue [D-Ala2, D-Leu5]-enkephalin. *J Pharm Pharmacol.* 2003; 55:1013-20.

83. Vavricka S R, Van Montfoort J, Ha H R, Meier P J and Fattinger K. Interactions of rifamycin S V and rifampicin with organic anion uptake systems of human liver. *Hepatology* (Baltimore, Md.). 2002; 36:164-72.

84. Fattinger K, Cattori V, Hagenbuch B, Meier P J and Stieger B. Rifamycin S V and rifampicin exhibit differential inhibition of the hepatic rat organic anion transporting polypeptides, Oatp1 and Oatp2. *Hepatology* (Baltimore, Md.). 2000; 32:82-6.

85. Cui Y, König J, Leier I, Buchholz U and Keppler D. Hepatic uptake of bilirubin and its conjugates by the human organic anion transporter SLC21A6. *J Biol Chem.* 2001; 276:9626-30.

86. Sekine T, Cha S H, Tsuda M, Apiwattanakul N, Nakajima N, Kanai Y and Endou H. Identification of multispecific organic anion transporter 2 expressed predominantly in the liver. *FEBS letters.* 1998; 429:179-82.

87. Hirano M, Maeda K, Shitara Y and Sugiyama Y. Drug-drug interaction between pitavastatin and various drugs via OATP1B1. *Drug Metab Dispos.* 2006; 34:1229-36.

88. Minematsu T and Giacomini K M. Interactions of tyrosine kinase inhibitors with organic cation transporters and multidrug and toxic compound extrusion proteins. *Mol Cancer Ther.* 2011; 10:531-9.

89. Shen H, Yang Z, Zhao W, Zhang Y and Rodrigues A D. Assessment of vandetanib as an inhibitor of various human renal transporters: inhibition of multidrug and toxin extrusion as a possible mechanism leading to decreased cisplatin and creatinine clearance. *Drug Metab Dispos.* 2013; 41:2095-103.

90. Cho S K, Kim C O, Park E S and Chung J Y. Verapamil decreases the glucose-lowering effect of metformin in healthy volunteers. *Br J Clin Pharmacol.* 2014; 78:1426-32.

91. Oostendorp R L, van de Steeg E, van der Kruijssen C M, Beijnen J H, Kenworthy K E, Schinkel A H and Schellens J H. Organic anion-transporting polypeptide 1B1 mediates transport of Gimatecan and BNP1350 and can be inhibited by several classic ATP-binding cassette (ABC) B1 and/or ABCG2 inhibitors. *Drug Metab Dispos.* 2009; 37:917-23.

92. Cvetkovic M, Leake B, Fromm M F, Wilkinson G R and Kim R B. OATP and P-glycoprotein transporters mediate the cellular uptake and excretion of fexofenadine. *Drug Metab Dispos.* 1999; 27:866-71.

93. Radchenko M, Symersky J, Nie R and Lu M. Structural basis for the blockade of MATE multidrug efflux pumps. *Nat Commun.* 2015; 6:7995.

94. Zhang L, Schaner M E and Giacomini K M. Functional characterization of an organic cation transporter (hOCT1) in a transiently transfected human cell line (HeLa). *J Pharmacol Exp Ther.* 1998; 286:354-61.

95. Gorboulev V, Ulzheimer J C, Akhoundova A, Ulzheimer-Teuber I, Karbach U, Quester S, Baumann C, Lang F, Busch A E and Koepsell H. Cloning and characterization of two human polyspecific organic cation transporters. *DNA and cell biology.* 1997; 16:871-81.

96. Wu X, Huang W, Ganapathy M E, Wang H, Kekuda R, Conway S J, Leibach F H and Ganapathy V. Structure, function, and regional distribution of the organic cation transporter OCT3 in the kidney. *American journal of physiology Renal physiology.* 2000; 279:F449-58.

97. Wu X, George R L, Huang W, Wang H, Conway S J, Leibach F H and Ganapathy V. Structural and functional characteristics and tissue distribution pattern of rat OCTN1, an organic cation transporter, cloned from placenta. *Biochim Biophys Acta.* 2000; 1466:315-27.

98. Wu X, Huang W, Prasad P D, Seth P, Rajan D P, Leibach F H, Chen J, Conway S J and Ganapathy V. Functional characteristics and tissue distribution pattern of organic cation transporter 2 (OCTN2), an organic cation/carnitine transporter. *J Pharmacol Exp Ther.* 1999; 290:1482-92.

Supplemental Methods

Human induced pluripotent cell derivation. All pluripotent and reprogramming cell cultures were maintained at 37° C. in Heracell VIOS 160i humidified incubators (Thermo Scientific) with 5% $CO_2$ and 5% 02. Differentiation cultures were maintained at 5% $CO_2$ and atmospheric $O_2$. Protocols were approved by the Northwestern University and University of British Columbia Institutional Review Boards. Patients had previously been genotyped with Illumina Infinium HumanOmniExpress array (738,432 SNPs). With informed written consent, ~9 ml of peripheral blood was taken from each volunteer and shipped at 4° C., samples were transferred to LeucoSep tubes (Greiner) filled with Histopaque-1077 (Sigma). $1\times10^6$ isolated peripheral blood mononuclear cells (PMBC) were grown in 24-well tissue culture-treated plates (Greiner) in 2 ml of SFEM II (Stem Cell Technologies) supplemented with 10 ng $ml^{-1}$ IL3, 50 ng $ml^{-1}$ SCF (KITLG), 40 ng $ml^{-1}$ IGF1 (all Peprotech), 2 U $ml^{-1}$ EPO, 1 µM dexamethasone (both Sigma)[37]. 50% medium was changed every other day. After 12 days of growth, 6×10⁴ cells were transferred to a well of a 24-well plate in 500 μl of SFEM II with growth factors supplemented with CytoTune-iPS 2.0 Sendai Reprogramming Kit viral particle factors (Invitrogen) 38 diluted to 10% of the manufacturer's recommendations. Cells were treated with 3.5 μl, 3.5 μl, and 2.2 μl of hKOS (0.85×10⁸ CIU ml⁻¹), hMYC (0.85' 108 CIU ml⁻¹), and hKLF4 (0.82' 108 CIU ml⁻¹), respectively at MOI of 5:5:3 (KOS:MYC:KLF4). 100% media was changed after 24 h by centrifugation (300×g for 4 min) to 2 ml fresh SFEM II with growth factors, and cells were transferred to one well of a 6-well plate (Greiner) coated with 2 ml of 1:800 reduced growth factor Matrigel (Corning) diluted in DMEM (Corning). 50% medium was changed gently every other day. On d8 after transduction, 100% of medium was changed to B8 medium. B8 medium was made in-house as previously described[39] and consisted of DMEM/F12 (10-092-CM, Corning), 5 μg ml-1 E. coli-derived recombinant human insulin (Gibco), 200 μg ml⁻¹ L-ascorbic acid 2-phosphate trisodium salt (Wako), 5 μg ml⁻¹ Oryza sativa-derived recombinant human transferrin (Sigma), 20 ng ml⁻¹ sodium selenite (Sigma), 40 ng ml⁻¹ recombinant human FGF2 (154 amino acids, E. coli-derived, made in-house), 0.1 ng ml⁻¹ recombinant human TGFβ3 (113 amino acid, E. coli-derived, Cell Guidance Systems), and 0.1 ng ml⁻¹ recombinant human NRG1 (65 amino acid, E. coli-derived, Peprotech). Medium was changed every day. At d17 individual colonies were picked in to a Matrigel-treated 12-well plate (one colony per well). Subsequently, cells were expanded in Matrigel-coated 6-well plates by passaging using 0.5 mM EDTA (Gibco) in DPBS without $Ca^{2+}$ or $Mg^{2+}$ (Corning) for 6 min at RT. Specific hiPSC clones used for this study were summarized in Table 2. The genotypes for SNP rs7853758 were confirmed through SLC28A3 gene sequencing in all hiPSC lines using Nanopore MinION sequencer.

Human induced pluripotent stem cell culture. Cells were routinely maintained in B8 medium (made as above) on 1:800 diluted growth factor reduced Matrigel. B8 was supplemented with 2 μM Rho kinase inhibitor (thiazovivin) (LC Labs), hereby referred to as B8T, for the first 24 h after passage. Cells were passaged at a ratio of 1:15 every 3 days using 0.5 mM EDTA, achieving 75% confluence. Cell lines were used between passages 20 and 80. All cultures (pluripotent and differentiation) were maintained with 2 ml medium per 9.6 cm2 of surface area or equivalent. All cultures were routinely tested for *Mycoplasma* using a MycoAlert PLUS Kit (Lonza) and a Varioskan LUX (Thermo Scientific) plate reader.

Karyotyping. Genomic DNA was extracted from the cell pellets using a Quick-DNA Miniprep Plus kit (Zymo). SNP karyotyping was performed using a whole-genome Infinium HumanCytoSNP-12 BeadChip Array (Illumina) covering 300,000 SNP using a NextSeq 500 (Illumina). Data was analyzed using BlueFuse Multi software (Illumina).

CRISPR/Cas9-mediated gene knockout. To generate SLC28A3 knockout gRNA expression vectors, gRNA targeting the start codon designed an online CRISPR design tool (http://tools.genome-engineering.org) with minimal predicted off-target effect[40]. Each gRNA with BbsI ligation overhangs was annealed and inserted into the BbsI restriction site of a pSpCas9(BB)-2A-Puro (PX459) V2.0 (48138, Addgene) plasmid that expresses puromycin resistance gene for downstream antibiotic selection, in addition to Cas9. The constructed gRNA expression plasmids were confirmed by Sanger sequencing (Eurofins) with LKO1_5_primer (5'-GACTATCATATGCTTACCG-3' (SEQ ID NO: 2)). 10⁶ cells were electroporated with 5 μg PX459 plasmid using Neon™ Transfection System (Invitrogen) using electroporation parameters, 1400 V, 20 ms, and 2 pulses. Positive clones were selected 24 h post transfection using puromycin (0.5 μg ml⁻¹) treatment for 48 h. Indels introduced by Cas9 were confirmed by sanger sequencing after PCR amplification of target region using forward primer (5'-AAACT-GAAGCAAGCTGTGCC-3'(SEQ ID NO: 3)) and reverse primer (5'-TTTGTCAACCCAGAAGAGCCC-3' (SEQ ID NO: 24))

CRISPR/Cas9-mediated gene overexpression. To generate SLC28A3 overexpressing cells, SLC28A cDNA (Mammalian Genome Collection (MGC) Human SLC28A3 Sequence-Verified cDNA (insert sequence, BC09382; CloneId, 7939666, Catalog number, MHS6278-202857241, Dharmacon) was first amplified and cloned into pENTR/D-TOPO® (Invitrogen) by TOPO cloning reaction performed according to the manufacturer protocol. SLC28A3 overexpression donor plasmid was generated by inserting SLC28A3 cDNA under the CAG promoter of a pAAVS1-Nst-CAG-DEST gateway cloning vector (80489, Addgene), which has a neomycin selection cassette in addition to homology arms for AAVS1, using Gateway LR Clonase II Enzyme Mix (Invitrogen). The constructed SLC28A3 donor plasmid was confirmed by Sanger sequencing with the following primer set: P3-F (5'-GGCGCCGGCAG-GAAGGAAAT-3' (SEQ ID NO: 4)) and P3-R (5'-AGCCAGGGCATTGGCCACAC-3' (SEQ ID NO: 5)). AAVS1 gRNA expression vector[41] (pXAT2, Addgene 80494), which expresses gRNA and Cas9, was used to target AAVS1 locus in the first intron of the PPP1R12C gene[41]. Cells were then electroporated (as mentioned above) with 1 μg AAVS1 targeting plasmid and 3 μg SLC28A3 overexpression donor plasmid. Positive clones were selected using neomycin (100 μg ml⁻¹) treatment for 14 days.

Cardiac differentiation. Differentiation into cardiomyocytes was performed according to previously described protocol with some modifications (FIG. 8A)[14, 42]. All cell lines for each individual experiment were differentiated in parallel to further reduce experimental variability. Briefly, hiPSCs were split at 1:15 ratios using 0.5 mM EDTA as above and grown in B8 medium for 3 days reaching 75% confluence. At the start of differentiation (day 0), B8 medium was changed to R6C[14], consisting of RPMI 1640 (Corning) and 6 μM of the glycogen synthase kinase 3-b inhibitor CHIR99021 (LC Labs). On day 1, medium was changed to RPMI 1640 only and on day 2 medium was changed to RBA consisting of RPMI, 2 mg ml⁻¹ fatty acid-free albumin (GenDEPOT) and 200 μg ml⁻¹ L-ascorbic acid 2-phosphate (Wako) supplemented with 0.5 μM of the Wnt inhibitor Wnt-C59 (Biorbyt). Medium was then changed on day 4 to RBAI consisting of 0.5 mg ml⁻¹ fatty acid-free albumin, 200 μg ml⁻¹ L-ascorbic acid 2-phosphate, and 5 μg ml⁻¹ insulin (Gibco). Medium was then changed every other day with RBAI. Contracting cells were noted from day 7. For each hiPSC line, we added a TNNT2 promotor-driven neomycin resistant cassette targeted to the AAVS1 locus[41] to guarantee cardiomyocyte purity to >80% TNNT2⁺. On day 8-12, cells were selected with 100 μg/ml G418/geneticin (Gibco). On day 16, cardiomyocytes were dissociated using DPBS for 20 min at 37° C. followed by 1:200 Liberase TH (Roche) in DPBS for 20 min at 37° C., manually triturated, centrifuged at 300 g for 5 min, filtered through a 100 μm cell strainer (Falcon). Live cells were counted using a LUNA-FL Dual Fluorescence cell counter (Logos Biosystems) then plated onto Matrigel-treated Nunc Lab-Tek II 8-chamber slides (50,000 cells per well), No 1.5 coverslips (100,000 cells per coverslip) in 12-well plates, 24-well plates (1×10⁶ cells per well), or 384-well white-sided µClear plates (50,000 cells per well) (all Greiner), in RBAI medium supplemented with 10% Cosmic Calf Serum (U.S. Origin, Hyclone) for 48 h and changed back to RBAI medium thereafter. Cardiomyocytes were used for analysis 30 days after differentiation.

Immunofluorescent staining. Cardiomyocytes were dissociated with Liberase TH and plated onto Matrigel-coated No 1.5 coverslips as described previously and allowed to adhere and spread for 4 days. Cells were fixed with 4% paraformaldehyde (Electron Microscopy Services) in DPBS for 15 min at RT, permeabilized with 10 mg ml$^{-1}$ (1%) saponin (Sigma) in DPBS for 15 min at RT, blocked with 30 mg ml$^{-1}$ (3%) bovine serum albumin (BSA, Sigma) and saponin in DPBS for 30 min at RT, and stained for 3 h in 3% BSA/1% saponin/DPBS at RT with 1:200 polyclonal rabbit IgG TNNT2 (Abcam, ab45932), 1:500 monoclonal mouse IgG1 ACTN2 (Sigma, A7811), 1:200 polyclonal rabbit IgG SLC28A3 (Origene, TA337177). Cells were washed three times in 1% saponin/DPBS and then stained with secondary antibodies 1:250 Alexa Fluor 488 goat anti-rabbit IgG, Alexa Fluor 957 594 goat anti-mouse IgG$_1$, or Alexa Fluor 488 goat anti-mouse IgG$_1$, Alexa Fluor 594 goat anti-rabbit IgG (all Invitrogen) in 3% BSA/1% saponin/DPBS for 1 h at RT in the dark. Cells were washed three times with 1% saponin/DPBS, with NucBlue (Invitrogen) in the last wash for 20 min and mounted with ProLong Diamond Antifade Mountant (Invitrogen). Slides were imaged with a Ti-E inverted fluorescent microscope (Nikon Instruments) and a Zyla sCMOS camera (Andor) using NIS-Elements 4.4 Advanced software.

Flow cytometry. hiPSCs were dissociated with TrypLE Express (Gibco) for 3 min at RT and 1×10⁶ cells were transferred to flow cytometry tubes (Falcon). For staining of surface marker, cells were stained 5 mg ml$^{-1}$ (0.5%) BSA (Sigma) in DPBS using 1:20 mouse IgG$_3$ SSEA4-488 (BD Biosciences, 560308) for 30 min at RT then washed twice in DPBS by centrifugation. For intracellular staining, cells were fixed with 4% PFA for 20 min at RT, washed twice with DPBS, and permeabilized with 1% saponin for 15 min at RT, and stained using 1:20 mouse IgG$_1$ POU5F1-647 (BD Biosciences, 560307), and mouse IgG$_1$ NANOG-647 (BD Biosciences, 561300) for 30 min at RT then washed. Isotype controls mouse IgG$_3$-488 (BD Biosciences, 563636) and mouse IgG$_1$-647 (BD Biosciences, 565571) were used to establish gating. Cardiomyocytes were dissociated with Liberase TH as described above, fixed and permeabilized as above, and stained using 1:100 mouse monoclonal IgG$_1$ TNNT2-647 (BD Biosciences, 565744) for 30 min at RT and washed again. Isotype controls mouse IgG$_1$-647 (BD Biosciences, 565571) were used to establish gating. Primary human dermal fibroblasts showed no staining under these conditions. All cells were analyzed using a CytoFLEX (Beckman Coulter) with CytExpert 2.0 software. To account for autofluorescence, each and every sample had a negative untreated control for which the fluorescence is measured before DOX treatment. Exemplary flow cytometry plots for DOX uptake in hiPSC-CMs is shown in FIG. 16.

Flow cytometry-based doxorubicin uptake quantification. On day 14, cardiomyocytes were dissociated and then plated on 12-well plate (2×10⁶ per well). On day 30, cells were treated for 24 h with either tested drugs in relevant concentration or RPMI 1640 medium (no phenol red, Corning) supplemented with 500 µg ml$^{-1}$ recombinant human serum albumin (Oryzogen) as negative control (FIG. 9). Cells were then treated with either doxorubicin (1 and 3 µM) alone or in combination with tested drugs in relevant concentrations. Cells auto-fluorescence was assayed before doxorubicin treatment and serves as baseline fluorescence. Doxorubicin intrinsic fluorescence-PE was measured 1 and 3 h post doxorubicin treatment and normalized to baseline fluorescence. All cells were stained with NucRed Live ReadyProbes Reagent (Invitrogen) to monitor cell viability.

Doxorubicin treatment. Doxorubicin hydrochloride (HY-15142, MedChem Express) was resuspended to 10 mM in cell culture-grade water (Corning). Day 30 hiPSC-CMs were treated for 24 h or 72 h with doxorubicin (0.01-100 µM) diluted in RPMI 1640 medium (no phenol red, Corning) supplemented with 500 µg ml$^{-1}$ recombinant human serum albumin (Oryzogen). For SLC transporter modulator drug screening, day 30 hiPSC-CMs were treated with respective drug 24 h prior to doxorubicin administration and then a second dose was co-administered with doxorubicin as above.

384-well plate-based cell viability, caspase 3/7 activity assays. To measure cell viability after 72 h of doxorubicin (0.01-100 µM) treatment, CellTiter-Glo 2.0 (Promega) was used per manufacturer's instructions. Luminescence was measured using a VarioSkan Lux Multi-Mode Reader (Thermo Scientific) with an integration time of 0.25 sec. Apoptosis was measured using Caspase 3/7-Glo (Promega) respectively according to manufacturer's instructions with an integration time of 1 sec. 10 µM staurosporine (MedChemExpress) was used as a positive control. Data were analyzed using Prism 7.0 software (GraphPad) using standard dose-response guidelines.

RNA-seq gene expression. RNA was extracted using a TRI reagent and Direct-zol RNA microprep kit (Zymo) including on-column DNase digestion to remove genomic DNA. Samples were quantified using an Agilent 2100 Bioanalyzer and passed QC. Forward stranded library preparation was done after ribosomal RNA depletion and sequencing with DNBseq platform sequencing (BGI), generating ~90 million paired-end 100 bp reads for each sample. Reads were mapped to the GRCh38 reference human genome using HISAT2[43]. Gene expression levels and exon usage were estimated using featureCounts function in the Subread software[46]. Differential gene expression analysis was done using DEseq2 package[47] and R (v3.3.3). Bioinformatics script and codes for the analysis are available upon request.

Quantitative Real-time PCR. RNA was isolated using a TRI reagent and Direct-zol RNA microprep kit (Zymo) including on-column DNase digestion to remove genomic DNA. cDNA was produced from 1 µg of total RNA using the High Capacity RNA-to-cDNA kit (Applied Biosystems). All PCR reactions were performed in triplicate in a 384-well plate format using TaqMan 1024 Gene Expression Master Mix in a QuantStudio 5 Real-Time PCR System (both Applied Biosystems) with following TaqMan Gene Expression Assays (Applied Biosystems): 18S (Hs99999901_s1), NANOG (Hs02387400_g1), POU5F1 (Hs00999632_g1), SOX2 (Hs01053049_s1), KLF4 (Hs00358836_m1), LIN28 (Hs00702808_s1), MYC Hs00153408_m1), UTF1 (Hs00747497_g1), DNMT3B (Hs01003405_m1), TERT (Hs99999022_m1), TP53 (Hs99999147_m1), SLC28A3 (hs00910439_m1). Relative quantification of gene expression was 1030 calculated using $2^{-\Delta\Delta Ct}$ method[48], normalized to the reference 18S and untreated control samples as specified in the figure legends.

Western blot. Cells were washed twice with DPBS, then the supernatant was aspirated, and the cell pellets were flash frozen. Cells were lysed with lysis buffer (150 mM NaCl, 1% Triton X-100, protease inhibitor and 50 mM Tris-HCl, pH 8.0). Cell protein was isolated by centrifugation at 4° C.

for 15 minutes at 15,000 rpm. Protein was quantified using Bradford assay (IBI scientific). 20-50 µg of protein was reduced and denatured in LDS sample buffer and reducing agent (Invitrogen) at 37° C. for 20 min, loaded onto the precast NuPage 10% Bis-Tris gel (Invitrogen) and run for 35 min at 200 V. Transfer to the nitrocellulose membrane (GE Healthcare) was performed at 10 V for 90 min. The membrane was blocked for 1 h at RT in the blocking buffer (5% BSA diluted with TBST) and incubated with 1:200 polyclonal rabbit SLC28A3 (Santa Cruz, sc134529), and 1:2000 monoclonal mouse $IgG^{2a}$ β-Tubulin (Invitrogen, MA5-16308) at 4° C. overnight. The membrane was then washed three times with TBST and incubated with 1:2000 HRP-goat anti-mouse IgG or HRP-goat anti-rabbit IgG (both Invitrogen) for 1 h at RT. The membrane was washed three times with TBST and incubated with Chemiluminescent substrate for quantitative chemiluminescent Westerns (Azure Biosystems) according to the manufacturer's recommendation. The chemiluminescent signals were captured using a CCD camera-based imager (Azure Biosystems).

Breast cancer cell lines. Four human breast cancer cell lines were used, MCF7 (adenocarcinoma, ATCC HTB-22) and Hs 578T (carcinsarcoma, ATCC HTB-126) both cultured in RPMI 1640 (Hyclone) with 10% FBS (Seradigm), MDA-MB-231 (adenocarcinoma, ATCC HTB-26) and MDA-MB-468 (adenocarcinoma, ATCC HTB-131) both cultured in DMEM (Corning) with 10% FBS. All cells were cultured on uncoated tissue culture plates and passaged with TrypLE Express (Gibco).

SLC28A3 candidate gene resequencing using MinION Nanopore sequencer. DNA extraction and purification. DNA was isolated from six patient derived human induced pluripotent stem cells, using QuickExtract DNA Extraction Solution (Epicenter) according to manufacturer protocol. Isolated DNA was then purified using Genomic DNA Clean & Concentrator-10 (Zymo) according to manufacturer protocol.

SLC28A3 locus amplification and amplicons validation. ~77 kb located on Chr9: 84,291,953-84,368,534 (NC 000009.12, GRCh38.p7) encompassing the coding region of SLC28A3 gene in addition to 9 kb and 5 kb at the 5'UTR and 3'UTR, respectively was amplified using long range PCR. A set of primer pairs were designed to amplify nine overlapping amplicons covering the target region whereas, length of amplicons ranged between 5732 and 9908 bp (Table 3). Generation of overlapping amplicons help compensate for the low depth of coverage associated with the start and the end of each sequence read. Using ~200 ng of DNA per reaction, amplicons were amplified using PrimeSTAR GXL DNA Polymerase (Takara) via three steps-PCR. PCR reaction mixture components and cycling conditions are described in Table 4. Generated amplicons were then purified using Genomic DNA Clean & Concentrator-5 (Zymo research) according to the manufacturer protocol to get rid of contaminants that might damage the pores of the Nanopore flow cell, which leads to a significant decrease in the number of sequence reads.

Amplicon validation prior sequencing. PCR product (amplicons) were run on 1% agarose gel and visualized by staining with GelGreen Nucleic Acid Stain (Biotium) (FIG. 1). Gel bands equivalent to target amplicons were confirmed for all amplified amplicons. For further confirmation that we got the correct amplicons, about 1 kb of the start and the end of each purified amplicon were then Sanger sequenced, and in silico aligned to its corresponding reference sequence. The quality and concentration of generated amplicons was assessed using NanoDrop 8000 and Qubit 3.0 fluorometer, respectively (Table 3). It is important to generate amplicons with reasonable purity to avoid ruining the pores of the flow cell which decreases the number of generated sequencing reads. Thus, amplicons with 260/280 and 260/230 of less than 1.8 and 1.5 were excluded and regenerated (Table 5).

MinION library preparation and flow cell loading. Library preparation was done using ligation sequencing (Oxford, Nanopore, SQK-LSK108) and 1D Native barcoding (Oxford, Nanopore, EXP-NBD103) kits. Nine amplicons from relevant patients were pooled together in am equimolar amount. Amplicons were then repaired using NEBNext FFPE Repair Mix (New England Biolabs, M6630) to maximize the read length by adding 1 mg DNA to 8.5 ml nuclease free water, 6.5 ml FFPE repair buffer, and 2 ml FFPE Repair. The reaction mix was then cleaned adding 62 ml AMPure XP beads (Beckman Coulter, A63880), DNA was then incubated on a hula mixer at room temperature for 5 min, spun down, and pelleted on a magnet, washed twice with 200 ml freshly prepared 70% ethanol. Samples was pun down again, placed back on a magnet, left to dry for ~30 sec. DNA was then removed from the magnet, re-suspended in 46 ml nucleases free water, incubated for 2 min at room temperature, and re-placed on a magnet until the elute is clear. Finally, 46 ml of clear elute was transferred to 1.5 ml Eppendorf DNA LoBind tube. End-repair and dA-tailing was then performed using NEBNext End repair/dA-tailing Module (New England Biolabs, E7546). Reaction mix was prepared by adding 45 ml eluted DNA to 7 ml Ultra II End-prep reaction buffer, 10 ml Ultra II End-prep enzyme mix, and 5 ml nuclease-free water. Reaction mix was then incubated for 5 min at 20° C. followed by 5 min at 65° C. DNA was then purified using AMPure XP beads (see above). Finally, 25 ml clear elute was transferred into DNA LoBind tube. Each sample was barcoded using 1D Native barcoding (Oxford, Nanopore, EXP-NBD103), 2.5 ml native Barcode was added to 22.5 ml end-prepped DNA, and 25 ml Blunt/TA Ligase Master Mix (New England Biolabs, M0367). Reaction mix was then incubated for 10 min at room temperature, DNA was than purified using AMPure XP beads (see above), and 26 ml of clear elute was transferred into Eppendorf DNA LoBind tube.

Barcoded samples were pooled in an equimolar amount to a final concentration of 700 ng, then diluted by adding 24 ml nuclease free water. Adapter ligation was then performed using NEBNext Quick Ligation Module (New England Biolabs, E6056). 700 ng pooled DNA was mixed with 20 ml Barcode Adapter Mix, 20 ml NEBNext Quick Ligation Reaction Buffer, and 10 ml Quick T4 DNA Ligase. Reaction mix was then incubated for 10 min at room temperature, and DNA was then purified by adding 62 ml AMPure XP beads Beckman Coulter, A63880), incubated on a hula mixer at room temperature for 5 min, spun down, and pelleted on a magnet, and Supernatant was discarded. Beads were then resuspended in 140 ml Adapter Bead Buffer (ABB) by flicking the tube, pelted on magnet, and supernatant was discarded (resuspension step was repeated). Pellet was resuspended in 15 ml Elution Buffer, incubated for 10 min at room temperature, pellet on magnet until the elute is clear, and finally 15 ml clear elute was transferred into Eppendorf DNA LoBind tube.

Priming mix was prepared by adding 576 µl RBF to 624 µl nuclease-free water, then 800 µl priming mix was loaded on the flow cell using priming port dropwise to avoid the introduction of air bubbles. Five minutes later, SpotON sample cover on MinION was opened and 200 µl priming mix was loaded. DNA library was prepared for loading by adding 12 µl DNA library to 35 µl RBF, 25.5 µl LLB, and 2.5

µl nuclease-free water. DNA library was gently mixed, loaded on the flow cell (FLO-MIN 106 R9 version, FAF19356) through SpotON port. Library was then sequenced for 48 hours with live base-calling.

Raw sequencing data and SNPs functional analysis. Raw barcoded sequence reads were demultiplexed into six fastaq files using Porechop[49]. Quality of demultiplexed sequence reads were assessed using Nanopack[50]. Sequence reads were then aligned to reference human genome (GRCh38.p92) using minimap2[51] "-ax map-ont", sam files were then sorted and converted into barn files using SAMtools[50]. Barn files were down-sampled using SAMtools "-s 0.1 to -s 0.9", and the quality of aligned reads were assessed using Nanopack. Depth of coverage analysis was done using deepTools2[51]. Sequence reads were indexed and variants were called using Nanopolish[22]. Variant call format files containing called SNPs were processed and analyzed using several tools including VCFtools[54], SnpSift[55], and BCFtools[56]. SNPs functional annotation analysis was done using DeepSEA[18], R (RCoreTeam) and BiomaRt[57] Bioconductor package that includes multiple ensemble gene regulation database. Conservation analysis was done using SnpSift[55] and PhastCons dataset that includes genome-wide multiple alignments with other 99 vertebrate species. (hgdownload.cse.ucsc.edu/goldenpath/hg38/phastCons100way)

Editing of the causal variant, rs11140490 in hiPSC derived form study patients. Locus specific base-editor protein complex and the gRNA were designed using Beditor[15], and the designed gRNA was cloned in the gRNA expressing plasmid (73797, Addgene). Then $1 \times 10^6$ cells were electroporated with 4 µg of the base editor expressing plasmid (pSI-Target-AID-NG, 119861, Addgene) and 4 µg of the gRNA expressing plasmid (lenti sgRNA (MS2)_puro, 73797, Addgene). Cells were then selected with 0.3 µg/ml puromycin 24 h post transfection for 48 h, clones were picked, the target locus was PCR-amplified and sanger-sequenced to confirm the SNP editing in all clones.

SLC28A3-AS1 overexpression in isogenic hiPSCs. The SLC28A3-AS1 cDNA was cloned into pLenti-C-Myc-DDK-IRES-Puro lentiviral vector (Origene) which was then co-transfected with packaging plasmids psPAX2 (Addgene 12260) and pMD2.G (Addgene 12259) into Lenti-X 293T cells (Takara) to generate lentivirus. Virus-containing supernatant was collected at 48- and 72-hours post-transfection. Lentivirus was concentrated 1:100 from cleared supernatant using PEGiT (SBI). Isogeneic hiPSCs were then transduced and positive clones were selected with puromycin for seven days to generate ISO$^{SLC28A3-AS1}$. SLC28A3-AS1 overexpression was confirmed using stranded RNA-Seq after ribosomal RNA depletion.

Mouse model of doxorubicin-induced cardiomyopathy and drug administration. C57BL/6J 10 weeks old male mice were co-treated with doxorubicin (NovaPlus) and water as a control vehicle (n=100), or with desipramine (Sigma) as experimental groups (n=8). At day 0, mice were treated with doxorubicin (3 mg kg$^{-1}$) intraperitoneally twice a week alone or with desipramine by Alzet pump infusion (20 mg kg$^{-1}$ day$^{-1}$) for 3 weeks (day 0-day 21). For the control group, we treated mice with corn oil in the same schedule as desipramine administration. We recorded an echocardiogram once a week (day 0, day 7, day 14, and day 21) and terminated the experiment at day 21.

Echocardiographic evaluation. Mice were studied at baseline and weekly during the protocol under light anesthesia with isoflurane (induction 3%, maintenance 1.5%). 2D images in the parasternal short axis were obtained with a GE Vivid 7 ultrasound system (GE Healthcare) equipped with a 13 MHz transducer. Left ventricular end-systolic (LVESD) and end-diastolic (LVEDD) dimensions were measured and left ventricular fractional shortening (FS) was calculated.

Statistical methods. Data were analyzed in R version 4.0.3 and graphed in GraphPad Prism 6. Detailed statistical information is included in the corresponding figure legends. Data were presented as mean±SEM. Comparisons were conducted via one way-ANOVA test, or an unpaired two-tailed Student's t-test with significant differences defined as P<0.05 (*), P<0.01 (), P<0.001 (*), and P<0.0001 (****). Our sample size (3 patients in each category) was based on the feasibility of handling this number of hiPSC lines. For dose response curves, log-logistic non linear regression model was used to estimate the value of the four parameters, and t-statistic was used to test for significant difference in $LD_{50}$ between different groups using "drc" package[57] in R. Patient exclusion criteria are outlined in Table 1. No statistical methods were used to predetermine sample size. The experiments were not randomized, and the investigators were not blinded to allocation during experiments and outcome assessment.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

TABLE 1

| Inclusion and exclusion criteria | |
|---|---|
| Inclusion Criteria | Exclusion Criteria |
| Diagnosis of cancer | Patients who have not been treated with doxorubicin |
| Treatment with doxorubicin (Adriamycin) | Unwilling to consent/assent to ≤15 ml blood draw (≤5 ml for children under 5 years) |
| Age <21 years at time treatment | |
| Must have previously participated in the research of CPNDS | |
| Must be European ancestry | |
| Documentation of pre-chemotherapy shortening fraction of ≥30% | |
| For DIC patients only: SF of ≤26%. Only echocardiograms ≥21 days after a doxorubicin dose are to be considered. | |
| For control patients: SF of ≥30% and no symptoms of cardiac compromise for at least 5 years after treatment | |

TABLE 2

Doxorubicin-treated patients recruited in this study

| ID | Anthracycline | Cardiotoxicity | Gender | Age at Treatment | Cancer diagnosis | Heart radiation | rs7853758 genotype |
|---|---|---|---|---|---|---|---|
| SLC$^{ref1}$ | Yes | Yes | Male | 5.1 | Wilm's Tumor | Yes | GG |
| SLC$^{ref2}$ | Yes | Yes | Male | 1.6 | ALL | No | GG |
| SLC$^{ref3}$ | Yes | Yes | Female | 4.3 | ALL | No | GG |
| SLC$^{var1}$ | Yes | No | Female | 2.7 | ALL | No | AG |
| SLC$^{var2}$ | Yes | No | Female | 2.2 | ALL | No | AG |
| SLC$^{var3}$ | Yes | No | Male | 1.6 | ALL | No | AG |
| ISO | No | NA | Male | NA | NA | No | GG |

TABLE 3 primers for SLC28A3 amplicons amplification

| Primer ID | Sequence 5' > 3' | SEQ ID NO | Direction | Amplicon length (bp) |
|---|---|---|---|---|
| Amp_1_fw | AGTTGCATGTTGCCATTCTG | 6 | Forward | 9218 |
| Amp_1_rw | GTTGCTGTAGCCCTCAGCTC | 7 | Reverse | |
| Amp_2_fw | CTCCCCAGGAGTGCAAATAG | 8 | Forward | 9908 |
| Amp_2_rv | TCAAGGGGAATCACTTCAGG | 9 | Reverse | |
| Amp_3_fw | TCAAGTTTGCATGATCACACC | 10 | Forward | 8979 |
| Amp_3_rv | CAGGAAATATGGCTTCAGCTC | 11 | Reverse | |
| Amp_4_fw | AAGGAAGATCCCACGTTGTG | 12 | Forward | 9286 |
| Amp_4_rv | AAGTGATGCTTCCCATCAGG | 13 | Reverse | |
| Amp_5_fw | GCTGTTTGTTGAATCGGATG | 14 | Forward | 9306 |
| Amp_5_rv | TCCAACTGTCTGAGCACCAG | 15 | Reverse | |
| Amp_6_fw | TGTTGCAGGTGTTTGGAAAG | 16 | Forward | 5732 |
| Amp_6_rv | ACATTATGAGCCCACCGAAG | 17 | Reverse | |
| Amp_7_fw | CGGCCGCTGGTGAGGTCCCCCAA | 18 | Forward | 8668 |
| Amp_7_rv | TGGGCAGTGGTGCTGGCAAGCGT | 19 | Reverse | |
| Amp_8_fw | TTGGCAATGTCCGGATTC | 20 | Forward | 9420 |
| Amp_8_rv | TTCCCCTTTCCAGGGATAAC | 21 | Reverse | |
| Amp_9_fw | GGACCTCTTCTCCCTGGAAC | 22 | Forward | 9509 |
| Amp_9_rv | AGACCCTAAGGCCTCTCCAG | 23 | Reverse | |

TABLE 4

PCR reaction mixture and conditions

| Amplicon | Composition of reaction mixture | PCR condition |
|---|---|---|
| Amp1, Amp2, Amp4, Amp5, and Amp9 | 10 µl 5X PrimeSTAR GXL Buffer, 4 µl dNTP Mixture (2.5 mM each), 1 µl of 100 µM primer, 300 ng DNA template, and 1 µl PrimeSTAR GXL DNA Polymerase 1.25 U/50 µl, and Sterile distilled water to 50 µl | 30 cycles 98° C. 10 sec 60° C. 15 sec 68° C. 10 min Hold at 4° C. |
| Amp3, and Amp 8 | 10 µl 5X PrimeSTAR GXL Buffer, 4 µl dNTP Mixture (2.5 mM each), 1 µl of 100 µM primer, 300 ng DNA template, and 1 µl PrimeSTAR GXL DNA Polymerase 1.25 U/50 µl, and Sterile distilled water to 50 µl | 30 cycles 98° C. 10 sec 58° C. 15 sec 68° C. 10 min Hold at 4° C. |
| Amp6 | 10 µl 5X PrimeSTAR GXL Buffer, 4 µl dNTP Mixture (2.5 mM each), 1 µl of 100 µM primer, 300 ng DNA template, and 1 µl PrimeSTAR GXL DNA Polymerase 1.25 U/50, and Sterile distilled water to 50 µl | 30 cycles 98° C. 10 sec 60° C. 15 sec 68° C. 6 min Hold at 4° C. |
| Amp7 | 10 µl 5X PrimeSTAR GXL Buffer, 4 µl dNTP Mixture (2.5 mM each), 1 µl of 100 µM primer, 300 ng DNA template, and 1 µl PrimeSTAR GXL DNA Polymerase 1.25 U/50, and Sterile distilled water to 50 µl | 30 cycles 98° C. 10 sec 66° C. 15 sec 68° C. 6 min Hold at 4° C. |

TABLE 5

Quality assessment of SLC28A3 amplicons

| Sample ID | Amplicon | Conc (ng/μl) | A260 | A280 | 260/280 | 260/230 |
|---|---|---|---|---|---|---|
| SLC$^{ref1}$ | Amp01 | 117.2 | 2.344 | 1.232 | 1.9 | 1.72 |
| | Amp02 | 7.525 | 0.15 | 0.095 | 1.58 | 1.69 |
| | Amp03 | 74.43 | 1.489 | 0.771 | 1.93 | 1.73 |
| | Amp04 | 48.37 | 0.967 | 0.514 | 1.88 | 2.08 |
| | Amp05 | 128.3 | 2.566 | 1.342 | 1.91 | 1.94 |
| | Amp06 | 59.79 | 1.196 | 0.649 | 1.84 | 1.62 |
| | Amp07 | 90.3 | 1.806 | 0.971 | 1.86 | 1.69 |
| | Amp08 | 7.217 | 0.144 | 0.074 | 1.95 | 1.52 |
| | Amp09 | 146.8 | 2.936 | 1.546 | 1.9 | 2.13 |
| SLC$^{ref2}$ | Amp01 | 148.3 | 2.967 | 1.57 | 1.89 | 2.14 |
| | Amp02 | 80.62 | 1.612 | 0.88 | 1.83 | 1.72 |
| | Amp03 | 51.97 | 1.039 | 0.549 | 1.89 | 1.75 |
| | Amp04 | 107.7 | 2.154 | 1.142 | 1.89 | 1.96 |
| | Amp05 | 98.96 | 1.979 | 1.06 | 1.87 | 1.95 |
| | Amp06 | 122.6 | 2.453 | 1.288 | 1.9 | 1.94 |
| | Amp07 | 103.4 | 2.069 | 1.123 | 1.84 | 1.88 |
| | Amp08 | 19.44 | 0.389 | 0.217 | 1.79 | 2.04 |
| | Amp09 | 81.35 | 1.627 | 0.855 | 1.9 | 2.02 |
| SLC$^{ref3}$ | Amp01 | 96.78 | 1.936 | 1.016 | 1.91 | 2.09 |
| | Amp02 | 60.44 | 1.209 | 0.672 | 1.8 | 1.57 |
| | Amp03 | 73.76 | 1.475 | 0.796 | 1.85 | 1.72 |
| | Amp04 | 134.1 | 2.681 | 1.424 | 1.88 | 2.07 |
| | Amp05 | 84.22 | 1.684 | 0.887 | 1.9 | 1.92 |
| | Amp06 | 41.24 | 0.825 | 0.439 | 1.88 | 1.86 |
| | Amp07 | 104.5 | 2.089 | 1.095 | 1.91 | 2.11 |
| | Amp08 | 45.57 | 0.911 | 0.496 | 1.84 | 1.79 |
| | Amp09 | 73.19 | 1.464 | 0.81 | 1.81 | 1.67 |
| SLC$^{var1}$ | Amp01 | 120.1 | 2.403 | 1.284 | 1.87 | 2.07 |
| | Amp02 | 40.18 | 0.804 | 0.449 | 1.79 | 1.61 |
| | Amp03 | 58.98 | 1.18 | 0.631 | 1.87 | 1.8 |
| | Amp04 | 91.2 | 1.824 | 0.973 | 1.87 | 1.92 |
| | Amp05 | 114.6 | 2.293 | 1.241 | 1.85 | 1.72 |
| | Amp06 | 93.09 | 1.862 | 0.979 | 1.9 | 2.01 |
| | Amp07 | 106.4 | 2.128 | 1.11 | 1.92 | 1.77 |
| | Amp08 | 64.44 | 1.289 | 0.711 | 1.81 | 1.91 |
| | Amp09 | 61.63 | 1.233 | 0.651 | 1.89 | 2.08 |
| SLC$^{var2}$ | Amp01 | 147 | 2.94 | 1.551 | 1.9 | 1.79 |
| | Amp02 | 38.41 | 0.768 | 0.405 | 1.9 | 1.78 |
| | Amp03 | 35.4 | 0.708 | 0.387 | 1.83 | 1.56 |
| | Amp04 | 155.2 | 3.105 | 1.664 | 1.87 | 1.91 |
| | Amp05 | 101.4 | 2.028 | 1.045 | 1.94 | 1.98 |
| | Amp06 | 46.66 | 0.933 | 0.494 | 1.89 | 1.88 |
| | Amp07 | 82.67 | 1.653 | 0.911 | 1.81 | 1.9 |
| | Amp08 | 14.07 | 0.281 | 0.15 | 1.88 | 1.81 |
| | Amp09 | 61.4 | 1.228 | 0.663 | 1.85 | 2.11 |
| SLC$^{var3}$ | Amp01 | 72.96 | 1.459 | 0.771 | 1.89 | 1.72 |
| | Amp02 | 116.3 | 2.327 | 1.246 | 1.87 | 2.13 |
| | Amp03 | 125.4 | 2.509 | 1.312 | 1.91 | 2.2 |
| | Amp04 | 59.99 | 1.2 | 0.644 | 1.86 | 1.55 |
| | Amp05 | 33.31 | 0.666 | 0.353 | 1.89 | 1.79 |
| | Amp06 | 141.3 | 2.826 | 1.515 | 1.87 | 1.73 |
| | Amp07 | 27.08 | 0.542 | 0.295 | 1.84 | 1.59 |
| | Amp08 | 41.91 | 0.838 | 0.44 | 1.91 | 1.72 |
| | Amp09 | 90.51 | 1.81 | 0.978 | 1.85 | 1.83 |

TABLE 6

Identified SLC28A3 SNP genotypes across study samples

| Position | SNP Id | REF | ALT | SLC$^{ref1}$ | SLC$^{ref2}$ | SLC$^{ref3}$ | SLC$^{var1}$ | SLC$^{var2}$ | SLC$^{var3}$ | Location | AA alteration |
|---|---|---|---|---|---|---|---|---|---|---|---|
| 84273903 | rs1332538 | C | T | 0 | 0 | 0 | 1 | 1 | 0 | 3'-UTR | |
| 84274601 | rs12003403 | G | A | 0 | 0 | 0 | 1 | 1 | 1 | 3'-UTR | |
| 84274729 | rs12003423 | G | A | 0 | 0 | 0 | 1 | 1 | 1 | 3'-UTR | |
| 84275091 | rs11140488 | A | T | 0 | 0 | 0 | 1 | 1 | 1 | 3'-UTR | |
| 84275843 | rs17426961 | C | T | 0 | 1 | 0 | 0 | 0 | 0 | 3'-UTR | |
| 84276016 | rs11140489 | T | A | 0 | 0 | 0 | 1 | 1 | 1 | 3'-UTR | |
| 84276158 | NA | C | T | 1 | 1 | 1 | 1 | 1 | 1 | 3'-UTR | |
| 84276679 | rs10868133 | T | C | 0 | 0 | 0 | 1 | 1 | 1 | 3'-UTR | |
| 84276696 | rs1036176955 | C | A | 0 | 0 | 0 | 0 | 0 | 1 | 3'-UTR | |
| 84277372 | rs4877272 | G | A | 0 | 0 | 0 | 1 | 1 | 1 | 3'-UTR | |
| 84277979 | rs3750406 | A | C | 0 | 0 | 0 | 1 | 1 | 1 | 3'-UTR | |
| 84278156 | rs7858075 | T | C | 0 | 0 | 0 | 1 | 1 | 1 | 3'-UTR | |
| 84278398 | rs11140490 | A | G | 0 | 0 | 0 | 1 | 1 | 1 | I17 | |
| 84278763 | NA | G | A | 1 | 1 | 1 | 1 | 1 | 1 | I17 | |
| 84279527 | rs7862562 | T | C | 0 | 1 | 0 | 1 | 1 | 1 | I16 | |
| 84279858 | rs1290966405 | C | T | 1 | 0 | 0 | 0 | 0 | 1 | I16 | |
| 84280938 | rs10868135 | T | C | 0 | 0 | 0 | 1 | 1 | 1 | I14 | |
| 84282506 | NA | C | T | 1 | 0 | 1 | 1 | 1 | 1 | I14 | |
| 84283431 | rs973302715 | A | G | 0 | 0 | 0 | 0 | 1 | 0 | I14 | |
| 84284969 | rs4877831 | C | G | 0 | 0 | 0 | 1 | 1 | 1 | I14 | |
| 84285032 | rs4877832 | A | C | 0 | 1 | 0 | 1 | 1 | 1 | I14 | |
| 84285101 | rs4877833 | T | C | 0 | 0 | 0 | 1 | 1 | 1 | I14 | |
| 84285427 | NA | G | A | 1 | 1 | 1 | 1 | 1 | 1 | E14 | A522V |
| 84285698 | rs7853066 | A | G | 0 | 0 | 0 | 1 | 1 | 1 | I13 | |
| 84286011 | rs7853758 | G | A | 0 | 0 | 0 | 1 | 1 | 1 | E13 | L489L |
| 84286220 | rs937635656 | G | A | 0 | 0 | 0 | 0 | 0 | 1 | I12 | |
| 84287089 | rs7030019 | A | G | 0 | 0 | 0 | 1 | 1 | 1 | I12 | |
| 84288640 | NA | G | A | 1 | 0 | 1 | 0 | 0 | 0 | I11 | |
| 84289166 | NA | G | A | 1 | 1 | 1 | 1 | 1 | 1 | I11 | |
| 84290636 | rs4877834 | T | C | 0 | 0 | 0 | 1 | 1 | 1 | I10 | |
| 84291093 | rs7047315 | A | G | 0 | 0 | 0 | 1 | 1 | 1 | I10 | |
| 84291502 | rs7047898 | A | C | 0 | 0 | 0 | 1 | 1 | 1 | I10 | |
| 84291663 | rs1050069561 | C | T | 1 | 1 | 1 | 1 | 1 | 1 | I10 | |
| 84291698 | NA | G | A | 1 | 1 | 1 | 1 | 1 | 1 | I10 | |
| 84291702 | NA | G | A | 1 | 1 | 1 | 1 | 1 | 1 | I10 | |
| 84294167 | rs10868137 | A | G | 0 | 0 | 0 | 1 | 1 | 1 | I9 | |
| 84294635 | rs885004 | G | A | 0 | 0 | 0 | 1 | 1 | 1 | I8 | |
| 84295359 | rs530032784 | C | T | 0 | 2 | 0 | 0 | 0 | 0 | I8 | |

TABLE 6-continued

Identified SLC28A3 SNP genotypes across study samples

| Position | SNP Id | REF | ALT | SLC$^{ref1}$ | SLC$^{ref2}$ | SLC$^{ref3}$ | SLC$^{var1}$ | SLC$^{var2}$ | SLC$^{var3}$ | Location | AA alteration |
|---|---|---|---|---|---|---|---|---|---|---|---|
| 84296355 | NA | C | T | 1 | 1 | 1 | 1 | 1 | 1 | I8 | |
| 84297553 | NA | C | T | 0 | 0 | 0 | 0 | 1 | 0 | I7 | |
| 84298559 | NA | G | A | 0 | 0 | 0 | 1 | 0 | 0 | I6 | |
| 84299856 | rs530032784 | G | A | 0 | 0 | 1 | 0 | 0 | 0 | I5 | |
| 84300626 | rs144419201 | C | T | 0 | 1 | 0 | 0 | 0 | 0 | I5 | |
| 84301200 | rs12379959 | A | T | 1 | 0 | 1 | 0 | 0 | 0 | I5 | |
| 84301258 | rs12377274 | G | A | 1 | 0 | 0 | 0 | 0 | 0 | I5 | |
| 84301936 | rs4877835 | T | G | 0 | 0 | 0 | 1 | 1 | 1 | I5 | |
| 84302092 | rs17087056 | C | A | 0 | 0 | 0 | 1 | 1 | 0 | I5 | |
| 84302173 | rs4877836 | T | C | 0 | 0 | 0 | 1 | 1 | 1 | I5 | |
| 84303804 | rs1021699143 | C | T | 1 | 1 | 1 | 1 | 1 | 1 | I4 | |
| 84305321 | rs7867504 | T | C | 0 | 0 | 0 | 1 | 1 | 1 | E4 | T89T |
| 84305796 | rs4242626 | T | C | 0 | 0 | 0 | 0 | 1 | 0 | I3 | |
| 84306347 | rs989230152 | C | T | 1 | 1 | 1 | 1 | 1 | 1 | I3 | |
| 84307078 | rs12237803 | C | T | 0 | 0 | 0 | 1 | 1 | 1 | I3 | |
| 84307083 | rs1262441955 | G | A | 0 | 1 | 1 | 0 | 0 | 0 | I3 | |
| 84307315 | rs142007597 | C | T | 1 | 0 | 0 | 0 | 0 | 0 | I3 | |
| 84307845 | rs150776148 | T | C | 1 | 0 | 0 | 0 | 0 | 0 | I3 | |
| 84308361 | rs141695271 | C | T | 0 | 0 | 0 | 0 | 1 | 0 | I3 | |
| 84308737 | NA | C | T | 1 | 1 | 1 | 1 | 1 | 1 | I3 | |
| 84313793 | rs13291905 | A | G | 0 | 1 | 0 | 1 | 0 | 1 | I1 | |
| 84313852 | rs7866821 | C | G | 2 | 1 | 1 | 0 | 2 | 0 | I1 | |
| 84314849 | rs4877843 | T | C | 0 | 0 | 0 | 0 | 1 | 0 | I1 | |
| 84319068 | rs1051842387 | T | C | 0 | 0 | 1 | 0 | 0 | 0 | I1 | |
| 84319815 | rs10735568 | T | C | 2 | 2 | 1 | 0 | 2 | 0 | I1 | |
| 84321516 | rs12347278 | G | A | 0 | 0 | 1 | 0 | 0 | 0 | I1 | |
| 84322400 | rs11140525 | G | A | 1 | 0 | 0 | 0 | 1 | 0 | I1 | |
| 84323144 | rs12004882 | C | G | 0 | 0 | 0 | 0 | 1 | 0 | I1 | |
| 84324414 | rs7046305 | T | C | 0 | 2 | 0 | 0 | 2 | 0 | I1 | |
| 84324908 | rs4877845 | A | C | 0 | 2 | 0 | 0 | 2 | 0 | I1 | |
| 84326000 | rs1331168053 | G | A | 1 | 1 | 1 | 1 | 1 | 1 | I1 | |
| 84326705 | rs4588940 | A | G | 0 | 0 | 0 | 0 | 2 | 0 | I1 | |
| 84327052 | rs7019546 | A | G | 0 | 2 | 0 | 0 | 2 | 0 | I1 | |
| 84327889 | rs10868148 | T | G | 0 | 2 | 0 | 0 | 2 | 0 | I1 | |
| 84328654 | rs4877846 | G | A | 0 | 0 | 0 | 0 | 2 | 0 | I1 | |
| 84328682 | rs4877273 | T | C | 0 | 2 | 0 | 0 | 2 | 0 | I1 | |
| 84328768 | rs4877274 | G | A | 0 | 2 | 0 | 0 | 2 | 0 | I1 | |
| 84328814 | rs11789143 | G | A | 1 | 1 | 1 | 1 | 1 | 1 | I1 | |
| 84329641 | NA | C | T | 1 | 1 | 1 | 1 | 1 | 1 | I1 | |
| 84330006 | rs4242627 | C | T | 0 | 0 | 0 | 0 | 2 | 0 | I1 | |
| 84330082 | rs4242628 | G | A | 1 | 0 | 0 | 1 | 2 | 0 | I1 | |
| 84330800 | rs58075154 | C | T | 0 | 0 | 0 | 0 | 2 | 0 | I1 | |
| 84330820 | rs57409783 | A | G | 0 | 0 | 0 | 0 | 2 | 0 | I1 | |
| 84331158 | rs17343066 | G | A | 1 | 1 | 1 | 0 | 2 | 1 | I1 | |
| 84331502 | rs4877847 | A | C | 1 | 1 | 1 | 1 | 2 | 1 | I1 | |
| 84331509 | rs75663843 | T | G | 0 | 1 | 0 | 0 | 0 | 0 | I1 | |
| 84331692 | rs980292 | T | C | 1 | 2 | 1 | 1 | 2 | 1 | I1 | |
| 84332442 | rs1972245 | T | C | 1 | 1 | 1 | 1 | 2 | 1 | I1 | |
| 84332615 | NA | G | A | 0 | 0 | 0 | 0 | 1 | 0 | I1 | |
| 84333013 | rs79257653 | C | T | 0 | 0 | 0 | 0 | 0 | 1 | I1 | |
| 84333038 | rs1248714397 | C | T | 1 | 1 | 1 | 1 | 1 | 1 | I1 | |
| 84333357 | rs118104816 | A | G | 0 | 1 | 1 | 0 | 0 | 0 | I1 | |
| 84333380 | rs4448361 | T | C | 1 | 1 | 1 | 1 | 2 | 1 | I1 | |
| 84333660 | rs76940186 | A | C | 0 | 1 | 1 | 0 | 0 | 0 | I1 | |
| 84333701 | rs4266723 | C | T | 1 | 2 | 2 | 1 | 2 | 1 | I1 | |
| 84335058 | rs10868149 | G | A | 0 | 1 | 1 | 0 | 0 | 0 | I1 | |
| 84335955 | rs4877848 | C | T | 0 | 1 | 1 | 0 | 0 | 0 | I1 | |
| 84336700 | rs4877850 | C | T | 1 | 2 | 2 | 1 | 2 | 1 | I1 | |
| 84337348 | rs6559781 | T | C | 1 | 2 | 2 | 1 | 2 | 1 | I1 | |
| 84337448 | rs149980849 | G | A | 0 | 1 | 0 | 0 | 0 | 0 | I1 | |
| 84338592 | NA | G | A | 0 | 0 | 1 | 0 | 0 | 0 | I1 | |
| 84338706 | rs17428030 | A | G | 0 | 1 | 0 | 0 | 0 | 0 | I1 | |
| 84338759 | rs7043257 | T | C | 1 | 2 | 1 | 1 | 2 | 1 | I1 | |
| 84339395 | rs4877852 | A | G | 1 | 2 | 1 | 1 | 2 | 1 | I1 | |
| 84339551 | rs7027983 | C | T | 1 | 2 | 1 | 1 | 2 | 1 | I1 | |
| 84339776 | rs7031310 | C | G | 1 | 2 | 1 | 1 | 2 | 1 | I1 | |
| 84339802 | rs7031197 | A | G | 2 | 2 | 2 | 1 | 2 | 2 | I1 | |
| 84340111 | NA | T | C | 0 | 0 | 0 | 1 | 0 | 0 | I1 | |
| 84340242 | rs3812509 | C | T | 1 | 2 | 1 | 1 | 2 | 1 | I1 | |
| 84340301 | rs1175981076 | C | T | 1 | 0 | 0 | 0 | 0 | 0 | I1 | |
| 84340767 | rs7035753 | C | T | 1 | 0 | 1 | 1 | 0 | 1 | 5'-UTR | |
| 84340824 | rs562029530 | C | T | 0 | 0 | 1 | 0 | 0 | 0 | 5'-UTR | |
| 84341021 | rs4604528 | T | C | 1 | 1 | 1 | 1 | 1 | 1 | 5'-UTR | |
| 84341181 | NA | G | A | 0 | 0 | 0 | 0 | 1 | 0 | 5'-UTR | |
| 84341186 | NA | T | G | 0 | 0 | 0 | 0 | 1 | 0 | 5'-UTR | |

TABLE 6-continued

Identified SLC28A3 SNP genotypes across study samples

| Position | SNP Id | REF | ALT | SLC$^{ref1}$ | SLC$^{ref2}$ | SLC$^{ref3}$ | SLC$^{var1}$ | SLC$^{var2}$ | SLC$^{var3}$ | Location | AA alteration |
|---|---|---|---|---|---|---|---|---|---|---|---|
| 84341202 | NA | C | T | 0 | 0 | 0 | 0 | 1 | 0 | 5'-UTR | |
| 84341213 | NA | C | T | 0 | 0 | 0 | 0 | 1 | 0 | 5'-UTR | |
| 84341214 | NA | A | G | 0 | 0 | 0 | 0 | 1 | 0 | 5'-UTR | |
| 84341215 | NA | C | T | 0 | 0 | 0 | 0 | 1 | 0 | 5'-UTR | |
| 84341217 | NA | T | C | 0 | 0 | 0 | 0 | 1 | 0 | 5'-UTR | |
| 84341405 | rs57404564 | C | A | 0 | 1 | 0 | 0 | 0 | 0 | 5'-UTR | |
| 84341428 | rs28629238 | A | G | 0 | 1 | 0 | 0 | 0 | 0 | 5'-UTR | |
| 84341697 | rs17343456 | A | G | 0 | 0 | 0 | 0 | 1 | 0 | 5'-UTR | |
| 84342889 | NA | C | T | 1 | 0 | 1 | 0 | 1 | 1 | 5'-UTR | |
| 84343833 | rs12335574 | A | G | 0 | 1 | 0 | 0 | 0 | 0 | 5'-UTR | |
| 84344334 | rs144927764 | G | A | 0 | 0 | 0 | 1 | 0 | 0 | 5'-UTR | |
| 84345145 | rs10780664 | C | A | 0 | 1 | 0 | 0 | 0 | 0 | 5'-UTR | |
| 84345715 | rs11140535 | A | G | 0 | 1 | 0 | 0 | 0 | 0 | 5'-UTR | |
| 84347396 | rs77681349 | C | T | 0 | 1 | 0 | 0 | 0 | 0 | 5'-UTR | |
| 84347715 | NA | C | T | 0 | 0 | 0 | 0 | 1 | 1 | 5'-UTR | |
| 84349384 | NA | C | A | 0 | 0 | 0 | 0 | 1 | 0 | 5'-UTR | |
| 84349394 | rs1298053988 | G | A | 0 | 0 | 0 | 0 | 1 | 0 | 5'-UTR | |
| 84349402 | NA | A | G | 0 | 0 | 0 | 0 | 1 | 0 | 5'-UTR | |
| 84349404 | NA | T | C | 0 | 0 | 0 | 0 | 1 | 0 | 5'-UTR | |
| 84349741 | rs13298157 | G | A | 0 | 1 | 0 | 0 | 0 | 0 | 5'-UTR | |

REF, reference allele; ALT, alternative allele; 0, homozygous reference; 1, heterozygous variant; and 2, homozygous variant; AA, amino acid.
SNPs in bold are SNPs coinherited in cardio protected patients but not in cardiotoxicity patients.
Variants are annotated in relevance to SLC28A3 transcript NM_001199633.1.

TABLE 7

Regulatory properties of SLC28A3 SNPs coinherited only in cardioprotected patients.

| rs Id | No. of altered chromatin feature binding sites |
|---|---|
| rs11140490 | 206 |
| rs4877835 | 204 |
| rs4877836 | 141 |
| rs7867504 | 134 |
| rs4877272 | 107 |
| rs885004 | 105 |
| rs12237803 | 52 |
| rs3750406 | 41 |
| rs12003403 | 40 |
| rs10868135 | 33 |
| rs4877831 | 32 |
| rs4877833 | 31 |
| rs10868137 | 30 |
| rs7853758 | 11 |
| rs7858075 | 6 |
| rs7047315 | 4 |
| rs7853066 | 4 |
| rs7030019 | 3 |
| rs12003423 | 2 |
| rs7047898 | 2 |
| rs11140488 | 1 |
| rs4877834 | 1 |
| rs11140489 | 0 |
| rs10868133 | 0 |

TABLE 8

SLC28A3 SNPs coinherited only in cardio protected patient affecting chromatin feature binding sites (showing only SNPs with Log2 fold change value >=1)

| SNP Id | Cell type| chromatin| treatment | E-value | Log2 fold change |
|---|---|---|---|
| rs4877272 | ECC-1|ERalpha|BPA_100 nM | 0.01 | −1.01 |
| | H1-hESC|TEAD4|None | 0.01 | −1.60 |
| | NT2-D1|DNase|None | 0.03 | −1.22 |
| | NHEK|DNase|None | 0.03 | −1.01 |
| | H7-hESC|DNase|None | 0.03 | −1.22 |
| | H1-hESC|DNase|None | 0.04 | −1.22 |
| | RWPE1|DNase|None | 0.05 | −1.09 |
| rs7867504 | GM12878|JunD|None | 0.00 | −1.11 |
| | PrEC|DNase|None | 0.01 | −1.55 |
| | GM12878|BATF|None | 0.01 | −1.34 |
| | GM12865|DNase|None | 0.01 | −1.04 |
| | GM12864|DNase|None | 0.01 | −1.00 |
| | SAEC|DNase|None | 0.01 | −1.62 |
| | HMEC|DNase|None | 0.01 | −1.12 |
| | HEEpiC|DNase|None | 0.01 | −1.52 |
| | pHTE|DNase|None | 0.01 | −1.06 |
| | NHEK|DNase|None | 0.01 | −1.17 |
| | HRCEpiC|DNase|None | 0.02 | −1.18 |
| | HRE|DNase|None | 0.02 | −1.21 |
| | HPDE6-E6E7|DNase|None | 0.02 | −1.22 |
| | MCF10A-Er-Src|STAT3|4OHTAM_1 uM_12 hr | 0.02 | −1.30 |
| | MCF10A-Er-Src|STAT3|EtOH_0.01 pct_12 hr | 0.02 | −1.25 |
| | MCF10A-Er-Src|c-Fos|4OHTAM_1 uM_12 hr | 0.02 | −1.81 |
| | MCF10A-Er-Src|c-Myc|4OHTAM_1 uM_4 hr | 0.02 | −1.06 |
| | MCF10A-Er-Src|STAT3|EtOH_0.01 pct_4 hr | 0.02 | −1.18 |
| | MCF10A-Er-Src|STAT3|4OHTAM_1 uM_36 hr | 0.02 | −1.21 |
| | MCF10A-Er-Src|STAT3|EtOH_0.01 pct | 0.02 | −1.00 |
| | MCF10A-Er-Src|c-Fos|4OHTAM_1 uM_4 hr | 0.02 | −1.67 |
| | RWPE1|DNase|None | 0.02 | −1.17 |
| | HUVEC|c-Fos|None | 0.03 | −1.09 |
| | MCF10A-Er-Src|c-Fos|EtOH_0.01 pct | 0.03 | −1.66 |
| | MCF10A-Er-Src|c-Fos|4OHTAM_1 uM_36 hr | 0.03 | −1.82 |
| | HMVEC-dBl-Ad|DNase|None | 0.03 | −1.13 |
| | RPTEC|DNase|None | 0.03 | −1.01 |

TABLE 8-continued

SLC28A3 SNPs coinherited only in cardio protected patient affecting chromatin feature binding sites (showing only SNPs with Log2 fold change value >=1)

| SNP Id | Cell type| chromatin| treatment | E-value | Log2 fold change |
|---|---|---|---|
| | HMVEC-dLy-Neo|DNase|None | 0.03 | −1.02 |
| | WI-38|DNase|4OHTAM_20 nM_72 hr | 0.04 | −1.28 |
| | HMVEC-LBl|DNase|None | 0.04 | −1.18 |
| | HUVEC|c-Jun|None | 0.04 | −1.01 |
| | HFF-Myc|DNase|None | 0.05 | −1.03 |
| | NHLF|DNase|None | 0.05 | −1.16 |
| | Melano|DNase|None | 0.00 | 1.05 |
| | HSMM_emb|DNase|None | 0.00 | 1.22 |
| | HSMMtube|DNase|None | 0.00 | 1.42 |
| | NHDF-neo|DNase|None | 0.00 | 1.76 |
| | NHDF-Ad|DNase|None | 0.00 | 1.73 |
| | AG10803|DNase|None | 0.00 | 1.56 |
| | ProgFib|DNase|None | 0.00 | 1.34 |
| | FibroP|DNase|None | 0.00 | 1.25 |
| | HGF|DNase|None | 0.00 | 1.56 |
| | HPdLF|DNase|None | 0.00 | 1.58 |
| | Stellate|DNase|None | 0.00 | 1.36 |
| | HCF|DNase|None | 0.00 | 1.42 |
| | AG09319|DNase|None | 0.00 | 1.46 |
| | HSMM|DNase|None | 0.00 | 1.36 |
| | SK-N-SH|TAF1|None | 0.00 | 1.07 |
| | HFF|DNase|None | 0.00 | 1.35 |
| | BJ|DNase|None | 0.00 | 1.42 |
| | HCM|DNase|None | 0.00 | 1.42 |
| | AG09309|DNase|None | 0.00 | 1.45 |
| | Myometr|DNase|None | 0.00 | 1.16 |
| | AG04449|DNase|None | 0.00 | 1.37 |
| | HPF|DNase|None | 0.00 | 1.51 |
| | AoAF|DNase|None | 0.00 | 1.36 |
| | AoSMC|DNase|None | 0.00 | 1.40 |
| | SKMC|DNase|None | 0.00 | 1.29 |
| | PanIsletD|DNase|None | 0.00 | 1.18 |
| | HMF|DNase|None | 0.00 | 1.42 |
| | HPAF|DNase|None | 0.00 | 1.31 |
| | HConF|DNase|None | 0.00 | 1.37 |
| | HAc|DNase|None | 0.00 | 1.07 |
| | HFF-Myc|DNase|None | 0.00 | 1.08 |
| | HBMEC|DNase|None | 0.00 | 1.29 |
| | WI-38|DNase|4OHTAM_20 nM_72 hr | 0.00 | 1.17 |
| | NH-A|DNase|None | 0.01 | 1.16 |
| | WI-38|DNase|None | 0.01 | 1.25 |
| | NHLF|DNase|None | 0.01 | 1.15 |
| | AG04450|DNase|None | 0.01 | 1.21 |
| | HCFaa|DNase|None | 0.01 | 1.13 |
| | HNPCEpiC|DNase|None | 0.01 | 1.16 |
| | HVMF|DNase|None | 0.01 | 1.26 |
| | HCPEpiC|DNase|None | 0.01 | 1.05 |
| | HIPEpiC|DNase|None | 0.01 | 1.06 |
| | HAEpiC|DNase|None | 0.01 | 1.10 |
| | NHDF-Ad|DNase|None | 0.01 | 1.07 |
| | NHDF-neo|DNase|None | 0.01 | 1.06 |
| | BE2_C|DNase|None | 0.01 | 1.08 |
| | SK-N-SH_RA|DNase|None | 0.01 | 1.08 |
| | H1-hESC|TCF12|None | 0.00 | 1.07 |
| | GM12878|ZEB1|None | 0.00 | 1.06 |

E-value, expect value stands for the significance of each individual chromatin feature predicted score; $\text{Log}^2$ fold change, measure the fold change in the probability of observing a binding site for relevant chromatin feature between reference and alternative allele for a particular SNP1.

TABLE 9

SLC28A3 SNPs coinherited only in cardioprotected patients located at regulatory regions and histone marks in cardiac tissues, and at transcription factor binding sites using ensemble regulatory build

| SNP Id | Position | Histone marks in cardiac tissue | Regulatory region in cardiac tissue | Motifs present at SNP locus |
|---|---|---|---|---|
| rs3750406 | 84277979 | NA | Open chromatin | TEAD4::RFX5, FOXJ3::TBX21, SOX6::TBX21, ELK1::FOXI1, ETV2::FOXI1, MGA, TBX2, TBX4, TBX5, ONECUT1, ONECUT2, ONECUT3, HOXB2::EOMES, HOXB2::TBX21, HOXB2::TBX3, MGA::DLX2, MGA::DLX3, MGA::EVX1, PITX1::HES7, E2F3::ONECUT2, TFAP2C::ONECUT2, ETV2::SREBF2, CUX1::SOX15, HOXB13::EOMES, HOXB13::TBX21, HOXD12::TBX21, TBX20, KLF13, KLF14, SREBF2, GLIS1, EOMES, SNAI2, TCF3, TCF4, THRB (n = 36) |
| rs7858075 | 84278156 | NA | Open chromatin | TEAD4::FOXI1, IRF3, ETV2::SOX15, POU2F1::FOXO6, POU2F1::DLX2, TEAD4::FOXI1 (n = 6) |
| rs11140490 | 84278398 | NA | Open chromatin | CLOCK::FIGLA, TEAD4::EOMES, TEAD4::TBX21, ETV2::DRGX, ZIC1, ZIC3, ZIC4, HOXB2::NHLH1, TEAD4::TCF3, GCM2::SOX15, and TEAD4::FIGLA (n = 11) |

TABLE 9-continued

SLC28A3 SNPs coinherited only in cardioprotected patients located at regulatory regions and histone marks in cardiac tissues, and at transcription factor binding sites using ensemble regulatory build

| SNP Id | Position | Histone marks in cardiac tissue | Regulatory region in cardiac tissue | Motifs present at SNP locus |
|---|---|---|---|---|
| rs4877831 | 84284969 | H3K4me1 | NA | NA |
| rs7047898 | 84291502 | H3K36me3 | NA | NA |
| rs10868137 | 84294167 | NA | | TFAP2C::DLX3, FOXO1::HOXB13, MGA::DLX3, HOXB2::TCF3 (n = 4) |
| rs885004 | 84294635 | NA | CTCF binding site | THRB, TEAD4::CEBPD, ERF::PITX1, ETV2::GSC2, ERF::ONECUT2, ETV2::ONECUT2, FLI1::ONECUT2, POU2F1::DLX2, R, X3::SRF, TEAD4::PAX5, PITX1::HES7, HESX1, LHX9, HOXD12::HOXA3, ZBED1, BARHL2, E2F1, E2F2, E2F3, BARX1, MSX1, MSX2, TBX1, TBX20, HOXB13::EOMES, HOXB13::TBX21, TEAD4::HOXB13, PBX4::HOXA1, PBX4::HOXA10, ONECUT1, ONECUT2, HMX1, HMX2, HMX3, CUX1::SOX15, TFAP2C::ONECUT2 (n = 36) |
| rs4877835 | 84301936 | NA | NA | POU2F1::FOXO6, POU2F1::EOMES, CLOCK::BHLHA15, MAX, TFAP4::MAX, HOXD12::EOMES, FOXO1, FOXO3, FOXO4, FOXO6, CTCF, ZNF238, ASCL2, BHLHA15, BHLHE22, BHLHE23, MESP2, MSC, MYF6, NEUROD2, NEUROG2, NHLH1, OLIG1, OLIG2, OLIG3, TCF15, TFAP4, ESRRA, ESRRG, FOXJ2::HOXB13 (n = 30) |
| rs4877836 | 84302173 | NA | NA | MYBL1, MYBL2, IRF4, IRF5, IRF8, IRF9, ELK1::FOXI1, ERF::FOXI1, ETV2::FOXI1, ETV5::FOXI1, FLI1::FOXI1, FOXO1::ELF1, FOXO1::ELK1, ELK1::HOXA3 (n = 14) |

TABLE 10 eQTL functional annotation of SLC28A3 SNPs coinherited only in cardioprotected patients.

| SNP Id | P-value | NES | Tissue |
|---|---|---|---|
| rs10868133 | 2.10E−07 | −0.22 | Cells - Cultured fibroblasts |
| | 4.50E−07 | 0.21 | Thyroid |
| rs10868135 | 4.10E−07 | −0.22 | Cells - Cultured fibroblasts |
| | 0.0000034 | 0.2 | Thyroid |
| rs10868137 | 3.80E−07 | 0.23 | Thyroid |
| | 6.70E−07 | −0.22 | Cells - Cultured fibroblasts |
| rs11140488 | 1.60E−07 | −0.22 | Cells - Cultured fibroblasts |
| | 2.60E−07 | 0.22 | Thyroid |
| rs11140489 | 1.50E−07 | −0.22 | Cells - Cultured fibroblasts |
| | 4.20E−07 | 0.21 | Thyroid |
| rs11140490 | 1.40E−07 | −0.22 | Cells - Cultured fibroblasts |
| | 6.30E−07 | 0.21 | Thyroid |
| rs12003403 | 1.60E−07 | −0.22 | Cells - Cultured fibroblasts |
| | 2.60E−07 | 0.22 | Thyroid |
| rs12003423 | 1.60E−07 | −0.22 | Cells - Cultured fibroblasts |
| | 7.20E−07 | 0.21 | Thyroid |
| rs12237803 | 4.70E−08 | −0.24 | Cells - Cultured fibroblasts |
| | 7.50E−08 | 0.24 | Thyroid |
| rs3750406 | 1.40E−07 | −0.22 | Cells - Cultured fibroblasts |
| | 6.30E−07 | 0.21 | Thyroid |
| rs4877272 | 6.40E−08 | −0.23 | Cells - Cultured fibroblasts |
| | 5.60E−07 | 0.21 | Thyroid |
| rs4877831 | 6.00E−09 | −0.21 | Cells - Cultured fibroblasts |
| | 0.000021 | 0.16 | Thyroid |
| rs4877833 | 5.30E−07 | −0.21 | Cells - Cultured fibroblasts |
| | 8.90E−07 | 0.21 | Thyroid |
| rs4877834 | 4.70E−08 | 0.24 | Thyroid |
| | 7.40E−07 | −0.21 | Cells - Cultured fibroblasts |
| rs4877835 | 4.20E−07 | 0.23 | Thyroid |
| | 5.20E−07 | −0.22 | Cells - Cultured fibroblasts |
| rs4877836 | 3.10E−07 | −0.23 | Cells - Cultured fibroblasts |
| | 3.30E−07 | 0.23 | Thyroid |
| rs7030019 | 1.70E−08 | 0.25 | Thyroid |
| | 8.70E−08 | −0.23 | Cells - Cultured fibroblasts |
| | 0.000014 | 0.64 | Brain - Amygdala |
| rs7047315 | 3.80E−07 | 0.23 | Thyroid |
| | 6.70E−07 | −0.22 | Cells - Cultured fibroblasts |

TABLE 10-continued eQTL functional annotation of SLC28A3 SNPs coinherited only in cardioprotected patients.

| SNP Id | P-value | NES | Tissue |
|---|---|---|---|
| rs7047898 | 3.80E−07 | 0.23 | Thyroid |
|  | 6.70E−07 | −0.22 | Cells - Cultured fibroblasts |
| rs7853066 | 1.50E−07 | 0.23 | Thyroid |
|  | 7.00E−07 | −0.21 | Cells - Cultured fibroblasts |
| rs7853758 | 3.10E−08 | 0.23 | Thyroid |
|  | 0.0000019 | −0.2 | Cells - Cultured fibroblasts |
|  | 0.000014 | 0.61 | Brain - Amygdala |
| rs7867504 | 0.000003 | −0.16 | Cells - Cultured fibroblasts |
| rs885004 | 1.30E−07 | −0.23 | Cells - Cultured fibroblasts |
|  | 1.90E−07 | 0.23 | Thyroid |

NES, normalized effect size;
This analysis was done using GTEX eQTL database

TABLE 11

Linkage disequilibrium pattern of Nanopore-identified cardioprotective haplotype SNPs (n = 24) in 99 control individuals.

| SNP 1 | SNP 2 | D' | $R^2$ |
|---|---|---|---|
| rs12003403 | rs12003423 | 1.00 | 1.00 |
| rs12003403 | rs11140488 | 1.00 | 1.00 |
| rs12003403 | rs11140489 | 1.00 | 1.00 |
| rs12003403 | rs10868133 | 1.00 | 1.00 |
| rs12003403 | rs4877272 | 1.00 | 1.00 |
| rs12003403 | rs3750406 | 1.00 | 1.00 |
| rs12003403 | rs7858075 | 1.00 | 1.00 |
| rs12003403 | rs11140490 | 1.00 | 1.00 |
| rs12003403 | rs10868135 | 1.00 | 1.00 |
| rs12003403 | rs4877831 | 0.96 | 0.65 |
| rs12003403 | rs4877833 | 1.00 | 0.97 |
| rs12003403 | rs7853066 | 1.00 | 0.85 |
| rs12003403 | rs7853758 | 0.97 | 0.82 |
| rs12003403 | rs7030019 | 1.00 | 0.85 |
| rs12003403 | rs4877834 | 1.00 | 0.88 |
| rs12003403 | rs7047315 | 1.00 | 0.88 |
| rs12003403 | rs7047898 | 1.00 | 0.88 |
| rs12003403 | rs10868137 | 1.00 | 0.88 |
| rs12003403 | rs885004 | 1.00 | 0.85 |
| rs12003403 | rs4877835 | 1.00 | 0.88 |
| rs12003403 | rs4877836 | 1.00 | 0.88 |
| rs12003403 | rs7867504 | 0.95 | 0.37 |
| rs12003403 | rs12237803 | 1.00 | 0.82 |
| rs12003423 | rs11140488 | 1.00 | 1.00 |
| rs12003423 | rs11140489 | 1.00 | 1.00 |
| rs12003423 | rs10868133 | 1.00 | 1.00 |
| rs12003423 | rs4877272 | 1.00 | 1.00 |
| rs12003423 | rs3750406 | 1.00 | 1.00 |
| rs12003423 | rs7858075 | 1.00 | 1.00 |
| rs12003423 | rs11140490 | 1.00 | 1.00 |
| rs12003423 | rs10868135 | 1.00 | 1.00 |
| rs12003423 | rs4877831 | 0.96 | 0.65 |
| rs12003423 | rs4877833 | 1.00 | 0.97 |
| rs12003423 | rs7853066 | 1.00 | 0.85 |
| rs12003423 | rs7853758 | 0.97 | 0.82 |
| rs12003423 | rs7030019 | 1.00 | 0.85 |
| rs12003423 | rs4877834 | 1.00 | 0.88 |
| rs12003423 | rs7047315 | 1.00 | 0.88 |
| rs12003423 | rs7047898 | 1.00 | 0.88 |
| rs12003423 | rs10868137 | 1.00 | 0.88 |
| rs12003423 | rs885004 | 1.00 | 0.85 |
| rs12003423 | rs4877835 | 1.00 | 0.88 |
| rs12003423 | rs4877836 | 1.00 | 0.88 |
| rs12003423 | rs7867504 | 0.95 | 0.37 |
| rs12003423 | rs12237803 | 1.00 | 0.82 |
| rs4877272 | rs3750406 | 1.00 | 1.00 |
| rs4877272 | rs7858075 | 1.00 | 1.00 |
| rs4877272 | rs11140490 | 1.00 | 1.00 |
| rs4877272 | rs10868135 | 1.00 | 1.00 |
| rs4877272 | rs4877831 | 0.96 | 0.65 |
| rs4877272 | rs4877833 | 1.00 | 0.97 |
| rs4877272 | rs7853066 | 1.00 | 0.85 |
| rs4877272 | rs7853758 | 0.97 | 0.82 |
| rs4877272 | rs7030019 | 1.00 | 0.85 |
| rs4877272 | rs4877834 | 1.00 | 0.88 |
| rs4877272 | rs7047315 | 1.00 | 0.88 |
| rs4877272 | rs7047898 | 1.00 | 0.88 |
| rs4877272 | rs10868137 | 1.00 | 0.88 |
| rs4877272 | rs885004 | 1.00 | 0.85 |
| rs4877272 | rs4877835 | 1.00 | 0.88 |
| rs4877272 | rs4877836 | 1.00 | 0.88 |
| rs4877272 | rs7867504 | 0.95 | 0.37 |
| rs4877272 | rs12237803 | 1.00 | 0.82 |
| rs7858075 | rs11140490 | 1.00 | 1.00 |
| rs7858075 | rs10868135 | 1.00 | 1.00 |
| rs7858075 | rs4877831 | 0.96 | 0.65 |
| rs7858075 | rs4877833 | 1.00 | 0.97 |
| rs7858075 | rs7853066 | 1.00 | 0.85 |
| rs7858075 | rs7853758 | 0.97 | 0.82 |
| rs7858075 | rs7030019 | 1.00 | 0.85 |
| rs7858075 | rs4877834 | 1.00 | 0.88 |
| rs7858075 | rs7047315 | 1.00 | 0.88 |
| rs7858075 | rs7047898 | 1.00 | 0.88 |
| rs7858075 | rs10868137 | 1.00 | 0.88 |
| rs7858075 | rs885004 | 1.00 | 0.85 |
| rs7858075 | rs4877835 | 1.00 | 0.88 |
| rs7858075 | rs4877836 | 1.00 | 0.88 |
| rs7858075 | rs7867504 | 0.95 | 0.37 |
| rs7858075 | rs12237803 | 1.00 | 0.82 |
| rs10868135 | rs4877831 | 0.96 | 0.65 |
| rs10868135 | rs4877833 | 1.00 | 0.97 |
| rs10868135 | rs7853066 | 1.00 | 0.85 |
| rs10868135 | rs7853758 | 0.97 | 0.82 |
| rs10868135 | rs7030019 | 1.00 | 0.85 |
| rs10868135 | rs4877834 | 1.00 | 0.88 |
| rs10868135 | rs7047315 | 1.00 | 0.88 |
| rs10868135 | rs7047898 | 1.00 | 0.88 |
| rs10868135 | rs10868137 | 1.00 | 0.88 |
| rs10868135 | rs885004 | 1.00 | 0.85 |
| rs10868135 | rs4877835 | 1.00 | 0.88 |
| rs10868135 | rs4877836 | 1.00 | 0.88 |
| rs10868135 | rs7867504 | 0.95 | 0.37 |
| rs10868135 | rs12237803 | 1.00 | 0.82 |
| rs4877831 | rs4877833 | 1.00 | 0.68 |
| rs4877831 | rs7853066 | 1.00 | 0.59 |
| rs4877831 | rs7853758 | 0.92 | 0.52 |
| rs4877831 | rs7030019 | 0.96 | 0.54 |
| rs4877831 | rs4877834 | 0.96 | 0.56 |
| rs4877831 | rs7047315 | 0.96 | 0.56 |
| rs4877831 | rs7047898 | 0.96 | 0.56 |
| rs4877831 | rs10868137 | 0.96 | 0.56 |
| rs4877831 | rs885004 | 0.96 | 0.54 |
| rs4877831 | rs4877835 | 0.96 | 0.56 |
| rs4877831 | rs4877836 | 0.96 | 0.56 |
| rs4877831 | rs7867504 | 0.97 | 0.55 |
| rs4877831 | rs12237803 | 0.96 | 0.52 |
| rs4877833 | rs7853066 | 1.00 | 0.88 |
| rs4877833 | rs7853758 | 0.93 | 0.79 |
| rs4877833 | rs7030019 | 0.96 | 0.82 |
| rs4877833 | rs4877834 | 0.97 | 0.85 |
| rs4877833 | rs7047315 | 0.97 | 0.85 |
| rs4877833 | rs7047898 | 0.97 | 0.85 |
| rs4877833 | rs10868137 | 0.97 | 0.85 |
| rs4877833 | rs885004 | 0.96 | 0.82 |
| rs4877833 | rs4877835 | 0.97 | 0.85 |
| rs4877833 | rs4877836 | 0.97 | 0.85 |
| rs4877833 | rs7867504 | 0.95 | 0.36 |
| rs4877833 | rs12237803 | 0.96 | 0.79 |
| rs4877834 | rs7047315 | 1.00 | 1.00 |
| rs4877834 | rs7047898 | 1.00 | 1.00 |
| rs4877834 | rs10868137 | 1.00 | 1.00 |
| rs4877834 | rs885004 | 1.00 | 0.97 |
| rs4877834 | rs4877835 | 1.00 | 1.00 |
| rs4877834 | rs4877836 | 1.00 | 1.00 |
| rs4877834 | rs7867504 | 1.00 | 0.36 |
| rs4877834 | rs12237803 | 1.00 | 0.93 |
| rs7047315 | rs7047898 | 1.00 | 1.00 |

TABLE 11-continued

Linkage disequilibrium pattern of Nanopore-identified cardioprotective haplotype SNPs (n = 24) in 99 control individuals.

| SNP 1 | SNP 2 | D' | R² |
|---|---|---|---|
| rs7047315 | rs10868137 | 1.00 | 1.00 |
| rs7047315 | rs885004 | 1.00 | 0.97 |
| rs7047315 | rs4877835 | 1.00 | 1.00 |
| rs7047315 | rs4877836 | 1.00 | 1.00 |
| rs7047315 | rs7867504 | 1.00 | 0.36 |
| rs7047315 | rs12237803 | 1.00 | 0.93 |
| rs885004 | rs4877835 | 1.00 | 0.97 |
| rs885004 | rs4877836 | 1.00 | 0.97 |
| rs885004 | rs7867504 | 1.00 | 0.35 |
| rs885004 | rs12237803 | 1.00 | 0.97 |
| rs7867504 | rs12237803 | 1.00 | 0.34 |
| rs11140488 | rs10868133 | 1.00 | 1.00 |
| rs11140488 | rs4877272 | 1.00 | 1.00 |
| rs11140488 | rs3750406 | 1.00 | 1.00 |
| rs11140488 | rs7858075 | 1.00 | 1.00 |
| rs11140488 | rs11140490 | 1.00 | 1.00 |
| rs11140488 | rs10868135 | 1.00 | 1.00 |
| rs11140488 | rs4877831 | 0.96 | 0.65 |
| rs11140488 | rs4877833 | 1.00 | 0.97 |
| rs11140488 | rs7853066 | 1.00 | 0.85 |
| rs11140488 | rs7853758 | 0.97 | 0.82 |
| rs11140488 | rs7030019 | 1.00 | 0.85 |
| rs11140488 | rs4877834 | 1.00 | 0.88 |
| rs11140488 | rs7047315 | 1.00 | 0.88 |
| rs11140488 | rs7047898 | 1.00 | 0.88 |
| rs11140488 | rs10868137 | 1.00 | 0.88 |
| rs11140488 | rs885004 | 1.00 | 0.85 |
| rs11140488 | rs4877835 | 1.00 | 0.88 |
| rs11140488 | rs4877836 | 1.00 | 0.88 |
| rs11140488 | rs7867504 | 0.95 | 0.37 |
| rs11140488 | rs12237803 | 1.00 | 0.82 |
| rs11140489 | rs10868133 | 1.00 | 1.00 |
| rs11140489 | rs4877272 | 1.00 | 1.00 |
| rs11140489 | rs3750406 | 1.00 | 1.00 |
| rs11140489 | rs7858075 | 1.00 | 1.00 |
| rs11140489 | rs11140490 | 1.00 | 1.00 |
| rs11140489 | rs10868135 | 1.00 | 1.00 |
| rs11140489 | rs4877831 | 0.96 | 0.65 |
| rs11140489 | rs4877833 | 1.00 | 0.97 |
| rs11140489 | rs7853066 | 1.00 | 0.85 |
| rs11140489 | rs7853758 | 0.97 | 0.82 |
| rs11140489 | rs7030019 | 1.00 | 0.85 |
| rs11140489 | rs4877834 | 1.00 | 0.88 |
| rs11140489 | rs7047315 | 1.00 | 0.88 |
| rs11140489 | rs7047898 | 1.00 | 0.88 |
| rs11140489 | rs10868137 | 1.00 | 0.88 |
| rs11140489 | rs885004 | 1.00 | 0.85 |
| rs11140489 | rs4877835 | 1.00 | 0.88 |
| rs11140489 | rs4877836 | 1.00 | 0.88 |
| rs11140489 | rs7867504 | 0.95 | 0.37 |
| rs11140489 | rs12237803 | 1.00 | 0.82 |
| rs10868133 | rs4877272 | 1.00 | 1.00 |
| rs10868133 | rs3750406 | 1.00 | 1.00 |
| rs10868133 | rs7858075 | 1.00 | 1.00 |
| rs10868133 | rs11140490 | 1.00 | 1.00 |
| rs10868133 | rs10868135 | 1.00 | 1.00 |
| rs10868133 | rs4877831 | 0.96 | 0.65 |
| rs10868133 | rs4877833 | 1.00 | 0.97 |
| rs10868133 | rs7853066 | 1.00 | 0.85 |
| rs10868133 | rs7853758 | 0.97 | 0.82 |
| rs10868133 | rs7030019 | 1.00 | 0.85 |
| rs10868133 | rs4877834 | 1.00 | 0.88 |
| rs10868133 | rs7047315 | 1.00 | 0.88 |
| rs10868133 | rs7047898 | 1.00 | 0.88 |
| rs10868133 | rs10868137 | 1.00 | 0.88 |
| rs10868133 | rs885004 | 1.00 | 0.85 |
| rs10868133 | rs4877835 | 1.00 | 0.88 |
| rs10868133 | rs4877836 | 1.00 | 0.88 |
| rs10868133 | rs7867504 | 0.95 | 0.37 |
| rs10868133 | rs12237803 | 1.00 | 0.82 |
| rs3750406 | rs7858075 | 1.00 | 1.00 |
| rs3750406 | rs11140490 | 1.00 | 1.00 |
| rs3750406 | rs10868135 | 1.00 | 1.00 |
| rs3750406 | rs4877831 | 0.96 | 0.65 |
| rs3750406 | rs4877833 | 1.00 | 0.97 |
| rs3750406 | rs7853066 | 1.00 | 0.85 |
| rs3750406 | rs7853758 | 0.97 | 0.82 |
| rs3750406 | rs7030019 | 1.00 | 0.85 |
| rs3750406 | rs4877834 | 1.00 | 0.88 |
| rs3750406 | rs7047315 | 1.00 | 0.88 |
| rs3750406 | rs7047898 | 1.00 | 0.88 |
| rs3750406 | rs10868137 | 1.00 | 0.88 |
| rs3750406 | rs885004 | 1.00 | 0.85 |
| rs3750406 | rs4877835 | 1.00 | 0.88 |
| rs3750406 | rs4877836 | 1.00 | 0.88 |
| rs3750406 | rs7867504 | 0.95 | 0.37 |
| rs3750406 | rs12237803 | 1.00 | 0.82 |
| rs11140490 | rs10868135 | 1.00 | 1.00 |
| rs11140490 | rs4877831 | 0.96 | 0.65 |
| rs11140490 | rs4877833 | 1.00 | 0.97 |
| rs11140490 | rs7853066 | 1.00 | 0.85 |
| rs11140490 | rs7853758 | 0.97 | 0.82 |
| rs11140490 | rs7030019 | 1.00 | 0.85 |
| rs11140490 | rs4877834 | 1.00 | 0.88 |
| rs11140490 | rs7047315 | 1.00 | 0.88 |
| rs11140490 | rs7047898 | 1.00 | 0.88 |
| rs11140490 | rs10868137 | 1.00 | 0.88 |
| rs11140490 | rs885004 | 1.00 | 0.85 |
| rs11140490 | rs4877835 | 1.00 | 0.88 |
| rs11140490 | rs4877836 | 1.00 | 0.88 |
| rs11140490 | rs7867504 | 0.95 | 0.37 |
| rs11140490 | rs12237803 | 1.00 | 0.82 |
| rs7853066 | rs7853758 | 0.97 | 0.90 |
| rs7853066 | rs7030019 | 0.97 | 0.93 |
| rs7853066 | rs4877834 | 0.97 | 0.90 |
| rs7853066 | rs7047315 | 0.97 | 0.90 |
| rs7853066 | rs7047898 | 0.97 | 0.90 |
| rs7853066 | rs10868137 | 0.97 | 0.90 |
| rs7853066 | rs885004 | 0.97 | 0.93 |
| rs7853066 | rs4877835 | 0.97 | 0.90 |
| rs7853066 | rs4877836 | 0.97 | 0.90 |
| rs7853066 | rs7867504 | 0.94 | 0.31 |
| rs7853066 | rs12237803 | 0.97 | 0.90 |
| rs7853758 | rs7030019 | 1.00 | 0.97 |
| rs7853758 | rs4877834 | 0.97 | 0.93 |
| rs7853758 | rs7047315 | 0.97 | 0.93 |
| rs7853758 | rs7047898 | 0.97 | 0.93 |
| rs7853758 | rs10868137 | 0.97 | 0.93 |
| rs7853758 | rs885004 | 1.00 | 0.97 |
| rs7853758 | rs4877835 | 0.97 | 0.93 |
| rs7853758 | rs4877836 | 0.97 | 0.93 |
| rs7853758 | rs7867504 | 0.95 | 0.32 |
| rs7853758 | rs12237803 | 1.00 | 0.93 |
| rs7030019 | rs4877834 | 1.00 | 0.97 |
| rs7030019 | rs7047315 | 1.00 | 0.97 |
| rs7030019 | rs7047898 | 1.00 | 0.97 |
| rs7030019 | rs10868137 | 1.00 | 0.97 |
| rs7030019 | rs885004 | 1.00 | 1.00 |
| rs7030019 | rs4877835 | 1.00 | 0.97 |
| rs7030019 | rs4877836 | 1.00 | 0.97 |
| rs7030019 | rs7867504 | 1.00 | 0.35 |
| rs7030019 | rs12237803 | 1.00 | 0.97 |
| rs7047898 | rs10868137 | 1.00 | 1.00 |
| rs7047898 | rs885004 | 1.00 | 0.97 |
| rs7047898 | rs4877835 | 1.00 | 1.00 |
| rs7047898 | rs4877836 | 1.00 | 1.00 |
| rs7047898 | rs7867504 | 1.00 | 0.36 |
| rs7047898 | rs12237803 | 1.00 | 0.93 |
| rs10868137 | rs885004 | 1.00 | 0.97 |
| rs10868137 | rs4877835 | 1.00 | 1.00 |
| rs10868137 | rs4877836 | 1.00 | 1.00 |
| rs10868137 | rs7867504 | 1.00 | 0.36 |
| rs10868137 | rs12237803 | 1.00 | 0.93 |
| rs4877835 | rs4877836 | 1.00 | 1.00 |
| rs4877835 | rs7867504 | 1.00 | 0.36 |

TABLE 11-continued

Linkage disequilibrium pattern of Nanopore-identified cardioprotective haplotype SNPs (n = 24) in 99 control individuals.

| SNP 1 | SNP 2 | D' | R² |
|---|---|---|---|
| rs4877835 | rs12237803 | 1.00 | 0.93 |
| rs4877836 | rs7867504 | 1.00 | 0.36 |
| rs4877836 | rs12237803 | 1.00 | 0.93 |

D', d prime; $R^2$, r-squared, linkage disequilibrium coefficients.

TABLE 12

List of drugs previously associated with attenuating uptake via SLC transporters.

| Drug | Transporter | References |
|---|---|---|
| Bosutinib | SLC16A2 and SLC29A1 | 4-Feb |
| Cimetidine | SLC22A2 and SLC47A2 | 5, 6 |
| Cyclosporin A | SLCO1B1, SLCO1B3, SLC10A2, SLC10A1, and SLC22A6, | 11-Jul |
| Dasatinib | SLCO1B1, SLCO1B3, SLC29A1, and SLC16A2 | 2, 3, 12 |
| Entecavir | SLC22A6 and SLC22A8 | 13 |
| Indomethacin | SLC22A6, SLCO1A2, SLC10A1, and SLC22A6 | 14, 15 |
| Nilotinib | SLCO1B1 and SLC29A1 | 3, 16 |
| Pazopanib hydrochloride | SLCO1B1 | 16, 17 |
| Phlorizin dihydrate | SLC5A2 and SLC5A2 | 18, 19 |
| Quinidine | SLC22A1, SLC22A2, SLC2A4, SL C22A5, SLCO1A2, and SLC22A8 | 20-26 |
| Rifampicin | SLC21A6, SLC21A8, SLC21A9, SLC21A3, SLCO1B3, SLC22A7, SLCO1B1, SLCO2B1, SLCO1A2, and SLCO1B3 | 27-30 |
| Rifamycin SV sodium salt | SLC21A6, SLC21A8, SLC21A9, SLC21A3, SLCO1A2, SLCO1B1, SLCO1B3, SLCO2A1, SLCO2B1, and SLC47A1 | 27, 28, 31 |
| Sulfobromophthalein sodium | SLC1A1 and SLCO1B2 | 27, 28 |
| Sunitinib | SLC22A1, SLC22A2 and SLC22A3 | 32 |
| Vadentanib | SLC22A2 | 33 |
| verapamil | SLC22A1, SLC22A4, SLC22A5, SLCO1B1, SLCO1A2, SLC47A1 and SLC47A2 | 25, 34-37 |
| Desipramine | SLC22A1, SLC22A2, SLC22A3, SLC22A4 and SLC22A5 | 38-42 |

TABLE 13

Major echocardiography parameters for mice treated with DOX and DOX + DESP at base line and three weeks post treatment.

| | DESP + DOX Mouse ID | | | | | | | | | |
|---|---|---|---|---|---|---|---|---|---|---|
| | 3453 | 3455 | 3456 | 3457 | 3458 | 3459 | 3460 | 3461 | Mean | SD |
| Base line | | | | | | | | | | |
| IVSd (mm) | 0.99 | 0.92 | 0.92 | 0.98 | 0.87 | 0.82 | 0.89 | 0.89 | 0.91 | 0.06 |
| IVSs (mm) | 1.38 | 1.27 | 1.3 | 1.33 | 1.31 | 1.06 | 1.36 | 1.21 | 1.28 | 0.1 |
| LVIDd (mm) | 3.48 | 4.03 | 3.15 | 3.58 | 3.75 | 3.96 | 3.84 | 3.8 | 3.7 | 0.29 |
| LVIDs (mm) | 1.82 | 2.66 | 1.74 | 2.14 | 2.12 | 2.39 | 2.14 | 2.28 | 2.16 | 0.3 |
| LVPWd (mm) | 0.89 | 0.82 | 0.92 | 0.89 | 0.95 | 0.96 | 0.96 | 0.95 | 0.92 | 0.05 |
| LVPWs (mm) | 1.11 | 1.1 | 1.05 | 1.11 | 1.03 | 1.15 | 1.04 | 1.06 | 1.08 | 0.04 |
| FS (%) | 47.33 | 34 | 45 | 40.33 | 43.67 | 39.67 | 44 | 40 | 41.75 | 4.14 |
| Week 3 | | | | | | | | | | |
| IVSd (mm) | 0.83 | 0.74 | 0.83 | 0.78 | 0.92 | 0.92 | 0.84 | 0.96 | 0.85 | 0.08 |
| IVSs (mm) | 1.11 | 1.12 | 1.27 | 1.05 | 1.23 | 1.28 | 1.28 | 1.36 | 1.21*** | 0.11 |
| LVIDd (mm) | 3.97 | 4.22 | 3.31 | 3.88 | 3.9 | 3.53 | 3.76 | 4.09 | 3.83 | 0.3 |
| LVIDs (mm) | 2.7 | 2.73 | 1.75 | 3.24 | 2.36 | 2.45 | 2.34 | 2.41 | 2.5 | 0.42 |
| LVPWd (mm) | 0.75 | 0.83 | 0.89 | 0.89 | 0.83 | 0.81 | 0.77 | 0.89 | 0.83 | 0.05 |

TABLE 13-continued

Major echocardiography parameters for mice treated with DOX
and DOX + DESP at base line and three weeks post treatment.

| | 1 | 2 | 3 | 4 | 5 | 6 | 7 | 8 | 9 | 10 | Mean | SD |
|---|---|---|---|---|---|---|---|---|---|---|---|---|
| LVPWs (mm) | 1 | 1.02 | 1.12 | 1.06 | 0.91 | 0.96 | 1.05 | 1.1 | | | 1.03** | 0.07 |
| FS (%) | 32 | 35 | 47.33 | 25 | 39.33 | 30.67 | 38 | 41 | | | 36.04*** | 6.92 |

DOX
Mouse ID

| | 1 | 2 | 3 | 4 | 5 | 6 | 7 | 8 | 9 | 10 | Mean | SD |
|---|---|---|---|---|---|---|---|---|---|---|---|---|
| Base line | | | | | | | | | | | | |
| IVSd (mm) | 0.89 | 0.89 | 0.78 | 0.74 | 0.85 | 0.71 | 0.74 | 0.71 | 0.74 | 0.78 | 0.78 | 0.07 |
| IVSs (mm) | 1.17 | 1.24 | 1.1 | 1.03 | 1.06 | 1.13 | 1.03 | 0.82 | 0.96 | 0.85 | 1.04 | 0.13 |
| LVIDd (mm) | 3.26 | 3.55 | 3.62 | 3.62 | 3.62 | 3.87 | 3.79 | 3.62 | 3.72 | 3.76 | 3.64 | 0.17 |
| LVIDs (mm) | 2.23 | 2.23 | 2.34 | 2.09 | 2.09 | 2.41 | 2.27 | 2.09 | 2.3 | 2.38 | 2.24 | 0.12 |
| LVPWd (mm) | 0.92 | 0.96 | 1.03 | 0.92 | 1.03 | 0.78 | 0.82 | 0.78 | 0.92 | 0.82 | 0.9 | 0.09 |
| LVPWs (mm) | 1.1 | 0.99 | 1.21 | 1.21 | 1.28 | 1.17 | 0.89 | 1.31 | 1.03 | 0.96 | 1.12 | 0.14 |
| FS (%) | 32.33 | 37.67 | 35.67 | 42 | 42 | 38 | 40.67 | 42.33 | 38.5 | 36 | 38.52 | 3.29 |
| Week 3 | | | | | | | | | | | | |
| IVSd (mm) | 0.78 | 0.74 | 0.92 | 0.82 | 0.78 | 0.85 | 0.74 | 0.78 | 0.78 | 0.82 | 0.8 | 0.05 |
| IVSs (mm) | 0.82 | 1.03 | 1.21 | 0.82 | 1.1 | 0.89 | 0.85 | 0.96 | 1.06 | 0.92 | 0.97 | 0.13 |
| LVIDd (mm) | 3.83 | 3.23 | 4.18 | 4.15 | 3.9 | 2.8 | 3.83 | 3.55 | 3.58 | 3.33 | 3.64 | 0.43 |
| LVIDs (mm) | 2.59 | 2.3 | 3.12 | 3.19 | 2.45 | 1.84 | 2.7 | 2.48 | 2.55 | 2.48 | 2.57 | 0.39 |
| LVPWd (mm) | 0.82 | 0.89 | 0.89 | 0.71 | 0.82 | 1.06 | 0.82 | 0.78 | 0.82 | 1.03 | 0.86 | 0.11 |
| LVPWs (mm) | 0.82 | 0.82 | 0.78 | 0.74 | 0.99 | 1.03 | 0.89 | 0.92 | 0.96 | 0.96 | 0.89 | 0.1 |
| FS (%) | 32 | 28 | 25 | 23.5 | 36.5 | 34.5 | 30.25 | 29.5 | 28.33 | 26.67 | 29.43 | 4.06 |

IVSd, LV interventricular septum thicknesses at diastole; IVSs, LV interventricular septum thicknesses at systole; LVIDd, LV internal dimensions at diastole; LVIDs, LV internal dimensions at systole; LVPWd, LV posterior wall thicknesses at diastole; LVPWs, LV posterior wall thicknesses at systole; and FS, fractional shortening; and
*, significant difference between groups (DESP + DOX versus DOX) by t-test,
*$P < 0.05$,
**$P \leq 0.01$,
***$P \leq 0.001$.

---

We claim:

1. A method of treating a subject having a cell proliferative disease or disorder that can be treated by administering an anthracycline, the method comprising administering to the subject: (i) an effective amount of the anthracycline for treating the cell proliferative disease or disorder; and (ii) an effective amount of a therapeutic agent that inhibits the activity or expression of the SLC28A3 transporter for inhibiting cardiotoxicity induced by the anthracycline, wherein the therapeutic agent is an SLC28A3 inhibitor selected from the group consisting of butoconazole, tetracaine, propofol, and desipramine.

2. The method of claim 1, wherein the cell proliferative disease or disorder is cancer, wherein the cancer is adenocarcinoma, leukemia, lymphoma, melanoma, myeloma, sarcoma, or teratocarcinoma, or wherein the cancer is a cancer of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, or uterus.

3. The method of claim 1, wherein the cell proliferative disease or disorder is leukemia.

4. The method of claim 1, wherein the anthracycline is selected from doxorubicin, daunorubicin, epirubicin, or idarubicin.

5. The method of claim 4, wherein the anthracycline is doxorubicin.

6. The method of claim 1, wherein an effective amount comprises a dose of the anthracycline that exceeds a recommended cumulative dose for the subject.

7. The method of claim 1, wherein the SLC28A3 inhibitor is desipramine.

8. The method of claim 1, wherein the subject has the polymorphic allele $SLC^{ref}$.

9. A method for treating a subject having a cell proliferative disorder that can be treated by administering an anthracycline, wherein the subject has a polymorphic allele $SLC^{ref}$, the method comprising:

(a) administering to the subject a cumulative dose of an anthracycline as follows:
doxorubicin, wherein the cumulative dose is greater than about 400 mg/m$^2$;
daunorubicin, wherein the cumulative dose is greater than about 600 mg/m$^2$;
epirubicin, wherein the cumulative dose is greater than about 900 mg/m$^2$;
idarubicin administered intravenously, wherein the cumulative dose is greater than about 150 mg/m$^2$; or
idarubicin administered orally, wherein the cumulative dose is greater than about 150 mg/m$^2$; and (b) administering a therapeutic agent that inhibits the activity or expression of the SLC28A3 transporter, wherein the therapeutic agent is an SLC28A3 inhibitor selected from the group consisting of butoconazole, tetracaine, propofol, and desipramine.

10. The method of claim 9, wherein the subject has at least one copy of the SLCref allele.

11. The method of claim 9, wherein the cell proliferative disease or disorder is cancer, wherein the cancer is adenocarcinoma, leukemia, lymphoma, melanoma, myeloma, sarcoma, or teratocarcinoma, or wherein the cancer is a cancer of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, or uterus.

12. The method of claim 11, wherein the cell proliferative disease or disorder is leukemia.

13. The method of claim 9, wherein the SLC28A3 inhibitor is desipramine.

14. A kit or treatment system comprising as components: (i) an anthracycline chemotherapeutic agent; and (ii) a therapeutic agent that inhibits the activity or expression of the SLC28A3 transporter, wherein the therapeutic agent is an SLC28A3 inhibitor selected from the group consisting of butoconazole, tetracaine, propofol, and desipramine.

* * * * *

SEQUENCE LISTING

```
Sequence total quantity: 24
SEQ ID NO: 1              moltype = AA    length = 691
FEATURE                   Location/Qualifiers
source                    1..691
                          mol_type = protein
                          organism = Homo sapiens
SEQUENCE: 1
MELRSTAAPR AEGYSNVGFQ NEENFLENEN TSGNNSIRSR AVQSREHTNT KQDEEQVTVE    60
QDSPRNREHM EDDDEEMQQK GCLERRYDTV CGFCRKHKTT LRHIIWGILL AGYLVMVISA   120
CVLNFHRALP LFVITVAAIF FVVWDHLMAK YEHRIDEMLS PGRRLLNSHW FWLKWVIWSS   180
LVLAVIFWLA FDTAKLGQQQ LVSFGGLIMY IVLLFLFSKY PTRVYWRPVL WGIGLQFLLG   240
LLILRTDPGF IAFDWLGRQV QTFLEYTDAG ASFVFGEKYK DHFFAFKVLP IVVFFSTVMS   300
MLYYLGLMQW IIRKVGWIML VTTGSSPIES VVASGNIFVG QTESPLLVRP YLPYITKSEL   360
HAIMTAGFST IAGSVLGAYI SFGVPSSHLL TASVMSAPAS LAAAKLFWPE TEKPKITLKN   420
AMKMESGDSG NLLEAATQGA SSSISLVANI AVNLIAFLAL LSFMNSALSW FGNMFDYPQL   480
SFELICSYIF MPFSFMMGVE WQDSFMVARL IGYKTFFNEF VAYEHLSKWI HLRKEGGPKF   540
VNGVQQYISI RSEIIATYAL CGFANIGSLG IVIGGLTSMA PSRKRDIASG AVRALIAGTV   600
ACFMTACIAG ILSSTPVDIN CHHVLENAFN STFPGNTTKV IACCQSLLSS TVAKGPGEVI   660
PGGNHSLYSL KGCCTLLNPS TFNCNGISNT F                                 691

SEQ ID NO: 2              moltype = DNA    length = 19
FEATURE                   Location/Qualifiers
source                    1..19
```

```
                            mol_type = other DNA
                            organism = synthetic construct
SEQUENCE: 2
gactatcata tgcttaccg                                                    19

SEQ ID NO: 3               moltype = DNA   length = 20
FEATURE                    Location/Qualifiers
source                     1..20
                           mol_type = other DNA
                           organism = synthetic construct
SEQUENCE: 3
aaactgaagc aagctgtgcc                                                   20

SEQ ID NO: 4               moltype = DNA   length = 20
FEATURE                    Location/Qualifiers
source                     1..20
                           mol_type = other DNA
                           organism = synthetic construct
SEQUENCE: 4
ggcgccggca ggaaggaaat                                                   20

SEQ ID NO: 5               moltype = DNA   length = 20
FEATURE                    Location/Qualifiers
source                     1..20
                           mol_type = other DNA
                           organism = synthetic construct
SEQUENCE: 5
agccagggca ttggccacac                                                   20

SEQ ID NO: 6               moltype = DNA   length = 20
FEATURE                    Location/Qualifiers
source                     1..20
                           mol_type = other DNA
                           organism = synthetic construct
SEQUENCE: 6
agttgcatgt tgccattctg                                                   20

SEQ ID NO: 7               moltype = DNA   length = 20
FEATURE                    Location/Qualifiers
source                     1..20
                           mol_type = other DNA
                           organism = synthetic construct
SEQUENCE: 7
gttgctgtag ccctcagctc                                                   20

SEQ ID NO: 8               moltype = DNA   length = 20
FEATURE                    Location/Qualifiers
source                     1..20
                           mol_type = other DNA
                           organism = synthetic construct
SEQUENCE: 8
ctccccagga gtgcaaatag                                                   20

SEQ ID NO: 9               moltype = DNA   length = 20
FEATURE                    Location/Qualifiers
source                     1..20
                           mol_type = other DNA
                           organism = synthetic construct
SEQUENCE: 9
tcaaggggaa tcacttcagg                                                   20

SEQ ID NO: 10              moltype = DNA   length = 21
FEATURE                    Location/Qualifiers
source                     1..21
                           mol_type = other DNA
                           organism = synthetic construct
SEQUENCE: 10
tcaagtttgc atgatcacac c                                                 21

SEQ ID NO: 11              moltype = DNA   length = 21
FEATURE                    Location/Qualifiers
source                     1..21
                           mol_type = other DNA
                           organism = synthetic construct
SEQUENCE: 11
caggaaatat ggcttcagct c                                                 21

SEQ ID NO: 12              moltype = DNA   length = 20
FEATURE                    Location/Qualifiers
```

```
source                1..20
                      mol_type = other DNA
                      organism = synthetic construct
SEQUENCE: 12
aaggaagatc ccacgttgtg                                                   20

SEQ ID NO: 13         moltype = DNA   length = 20
FEATURE               Location/Qualifiers
source                1..20
                      mol_type = other DNA
                      organism = synthetic construct
SEQUENCE: 13
aagtgatgct tcccatcagg                                                   20

SEQ ID NO: 14         moltype = DNA   length = 20
FEATURE               Location/Qualifiers
source                1..20
                      mol_type = other DNA
                      organism = synthetic construct
SEQUENCE: 14
gctgtttgtt gaatcggatg                                                   20

SEQ ID NO: 15         moltype = DNA   length = 20
FEATURE               Location/Qualifiers
source                1..20
                      mol_type = other DNA
                      organism = synthetic construct
SEQUENCE: 15
tccaactgtc tgagcaccag                                                   20

SEQ ID NO: 16         moltype = DNA   length = 20
FEATURE               Location/Qualifiers
source                1..20
                      mol_type = other DNA
                      organism = synthetic construct
SEQUENCE: 16
tgttgcaggt gtttggaaag                                                   20

SEQ ID NO: 17         moltype = DNA   length = 20
FEATURE               Location/Qualifiers
source                1..20
                      mol_type = other DNA
                      organism = synthetic construct
SEQUENCE: 17
acattatgag cccaccgaag                                                   20

SEQ ID NO: 18         moltype = DNA   length = 23
FEATURE               Location/Qualifiers
source                1..23
                      mol_type = other DNA
                      organism = synthetic construct
SEQUENCE: 18
cggccgctgg tgaggtcccc caa                                               23

SEQ ID NO: 19         moltype = DNA   length = 23
FEATURE               Location/Qualifiers
source                1..23
                      mol_type = other DNA
                      organism = synthetic construct
SEQUENCE: 19
tgggcagtgg tgctggcaag cgt                                               23

SEQ ID NO: 20         moltype = DNA   length = 18
FEATURE               Location/Qualifiers
source                1..18
                      mol_type = other DNA
                      organism = synthetic construct
SEQUENCE: 20
ttggcaatgt ccggattc                                                     18

SEQ ID NO: 21         moltype = DNA   length = 20
FEATURE               Location/Qualifiers
source                1..20
                      mol_type = other DNA
                      organism = synthetic construct
SEQUENCE: 21
ttccccttte cagggataac                                                   20

SEQ ID NO: 22         moltype = DNA   length = 20
```

```
FEATURE              Location/Qualifiers
source               1..20
                     mol_type = other DNA
                     organism = synthetic construct
SEQUENCE: 22
ggacctcttc tccctggaac                                                        20

SEQ ID NO: 23        moltype = DNA  length = 20
FEATURE              Location/Qualifiers
source               1..20
                     mol_type = other DNA
                     organism = synthetic construct
SEQUENCE: 23
agaccctaag gcctctccag                                                        20

SEQ ID NO: 24        moltype = DNA  length = 21
FEATURE              Location/Qualifiers
source               1..21
                     mol_type = other DNA
                     organism = synthetic construct
SEQUENCE: 24
tttgtcaacc cagaagagcc c                                                      21
```